United States Patent
Vos et al.

(10) Patent No.: US 6,613,962 B1
(45) Date of Patent: Sep. 2, 2003

(54) TOMATO NUCLEIC ACID ENCODING PROTEIN THAT CONFERS RESISTANCE TO APHIDS AND NEMATODES AND PLANTS TRANSFORMED THEREWITH

(75) Inventors: Pieter Vos, Renswoulde (NL); Marc Zabeau, Ghent (BE); Guus Simons, Ede (NL); Jelle Wijbrandi, Wageningen (NL)

(73) Assignee: Keygene N.V., Wageningen (NL)

( * ) Notice: Subject to any disclaimer, the term of this patent is extended or adjusted under 35 U.S.C. 154(b) by 0 days.

(21) Appl. No.: 09/245,928

(22) Filed: Feb. 8, 1999

Related U.S. Application Data

(63) Continuation of application No. PCT/EP97/04340, filed on Aug. 8, 1997.

(30) Foreign Application Priority Data

Aug. 9, 1996 (EP) .......................................... 96401764
May 16, 1997 (EP) .......................................... 97401101

(51) Int. Cl.⁷ ..................... C12N 15/09; C12N 15/29; C12N 15/82; A01H 5/00; C07H 21/04
(52) U.S. Cl. ..................... 800/301; 800/278; 800/287; 800/295; 800/298; 800/317.4; 800/279; 435/69.1; 435/468; 435/410; 435/419; 435/320.1; 435/252.3; 536/23.1; 536/23.2; 536/23.6
(58) Field of Search ................. 435/69.1, 468, 435/410, 419, 320.1; 536/23.1, 23.2, 23.6; 800/278, 279, 290, 295, 298, 287, 317.4

(56) References Cited

U.S. PATENT DOCUMENTS 5,494,813 A 2/1996 Hepher et al. .......... 435/172.3

FOREIGN PATENT DOCUMENTS

WO WO 93 18170 A 9/1993
WO WO 95/18230 6/1995

OTHER PUBLICATIONS

Broun et al. Science, vol. 282, pp. 131–133, 1998.
Lazar et al. Molecular and Cellular Biology, vol. 8, No. 3, pp. 1247–1252, 1988.
Ryals et al. The Plant Cell, vol. 8, pp. 1809–1819, 1996.
Kondo et al. Gene. 1989. vol. 81: 259–265.*
Urwin et al. The Plant Journal. Jul. 1995. vol. 8: 121–131.*
H. Kondo et al.: "Cloning and sequence analysis of the genomic DNA fragment encoding oryzacystatin" Gene, vol. 81, 1989, pp. 259–265, XP000652087 see Figure 3.
V.M. Williamson et al.: Molecular transfer of nematode resistance genes: J. Nematol., vol. 24, 1992, pp. 234–241, XP000653134 see the whole document.
J.–Y. Ho et al.: The root–knot nematode resistance gene (Mi) in tomato: construction of a molecular linkage map and identification of dominant cDNA markers in resistant genotypes: Plant J., vol. 2, pp. 971–982, XP000653162 see the whole document.
I. Kaloshian et al.: "An aphid–resistance locus is tightly linked to the nematode–resistance gene, Mi, in tomato" Proc. Natl. Acad. Sci. USA, vol. 92, 1995, pp. 622–625, XP002057306 cited in the application see the whole document.

* cited by examiner

Primary Examiner—Amy J. Nelson
Assistant Examiner—Medina A. Ibrahim
(74) Attorney, Agent, or Firm—Nixon & Vanderhye, P.C.

(57) ABSTRACT

The invention relates to tomato nucleic acid sequences encoding protein that confers resistance to nematodes and/or aphids, vectors, plant cells, plants and seeds comprising said nucleic acid sequences. The invention further relates to a process of transforming plants for increased resistance against nematodes and/or aphids.

23 Claims, 15 Drawing Sheets

```
5'-TTTTCCTCTTCATATAACTTTTTCCTTAACCCCTCTCATGAATAATATAATTGATGTGGA      60
   TAAAGTATTATCCTTTATGATAAATAACGAAATTTAATAATTTAAAGGGTGCAAATCTAT     120
   AAAATGGAGACGCACATTGATAATGTCCTCTTGATTATTATTAAAGAATTACTCTAGCTT     180
   CACAAATTTAAATTCATTAATGCTTAATTACATGATAAAAACTTTAGTTGTTCTTTTTAC     240
   ATGGTTTGCTAACTTTAATTTTTTTTCTTCATATTCTTCATTTGTTTATTATTATTTTCT     300
   AATTACTTATTTAACTTTTATACTCTTAATATTCATAACTCTCATCTTTTCATATTCATA     360
   ACCTCCAAATATTTAAACTAAAACTTTAAGATATCTTTTGATATTGTTCAATAATAAAT     420
   TCAACTTCTTTATCTTATGAAACCCCTACCAAGATTATTAGGCTATTATTTTTATTCTA     480
   TAGTAAAAACAAATGATGAAGATTCTTGAATTTTATAGGATATGAAAGAAGTCGATAAAA     540
   TCTCAGAGAGTTATGTACTAATTTTGTACTTATTTTTTCATCTATATACATAAATCTT     600
   ATAAGAATAATGTCTATATTGTATTTTTTTCTTAAATATTATGTTTCTTTTTAATTTTTT     660
   TTCACTCTGTTAGACTTCTTAATTTAGTTTTCTATGAATGTTTTATTGCCGTAAGTCTTT     720
   GAATTTTGTAATTGTTACATTTTATTATTCATTACGATTTACATATATATTTCCATGAGA     780
   TTTGGTCATTCTAACGTATCTATAAAAATTCACATGAAACACACGTGTGAAGCGCATCCT     840
   CAGAAAAACTAGTGTATATATATATATATATATATATATATATATATATATATATATATA     900
   TATATATATATATATATATATATATTATTCTTATTAAAAAGAATGTCCTTATTTCAT     960
   TTTTAATCTGGTTAAAAAGAATAATCTCTTTCCTTTTTTGACAATATTTTAACTTTAAC    1020
   TTTCCACGTAACATGTTTAAGACAACAAAATTAAATGACATTTTAATCTTGTAACATAGA    1080
   AAAGTAACATATGATAATTGTCGTTGTCCCTAAACATGATAGATGTATAATTCAAAAGTC    1140
   AATGAATTGTATTTTAGTATTATATTATGAATGAACAAACTGTCAAGATGTGTATATATA    1200
   TATATATTTTATTCTTGTTAATTTGGCCTTTCAAGTAATTAATTCATTGTTAGGCAGTTG    1260
   AATTAATAATCTCTTTTAGGAATCTTCCCATGTGAATAACAAGACTTATAATAATAATAA    1320
   TAAAGTCCAGATCTTGTTTCAATTGGATCATTTGGCAAACAATTACTCTGTTTCTGAAAC    1380
   AAGGAATAGGGCTTCTAATATTGTAGGGGATTTTTTTTTCTTCATTAATTTATACTTATG    1440
   ATATTAATTATTGTTTTGAGTACATATTTAAACTCTGTTGTTTATTTTCTGCAAAGT    1500
   TTCTCCGGTTATATTGAACATATACACATATAGTACATATATTTATTGTAAAAAAATAA    1560
   TTATTATACTCCATTTCAAGAAATTATGTTTTGATATTATATATTAAATTCTATAATGTG    1620
   GAAATTGTCAATGTCTACAATGTGTTTGATGAAATGACAACCACTTGTTTTATCTGCAA    1680
   CAGTATAAAAATTGGCTTTGCTTCTTTTAGATTAATATAATATTTTACAGGTCACATATT    1740
   ATATTTATATTGTGAAAGACAAGAGATATTGATTAAAAAAAGACTTATGGGTTTGTATTT    1800
   TAATATTTCATTCTTCTTCATTACTAAAAGACTTGTATCGTATATTTCAACTACTACACT    1860
   TGTTTTCTTATCCAATAGCTTCAACATTATTTCTCAAACAAAGGGTTCTCTAGCTAAACT    1920
   TCAGCCTGTGTAAAGGTAACATCTTCTTTATTCACAGCATAATAACAATGAATTTGGTCG    1980
   ATGTTTGAAGTAAGCTTGAAATTTTCTCTTTCTAAGTTTGTTTGATCCATTTAGATTCTT    2040
   TTAAATACTTTTTGGTATTTAAAGGACTTGTGAAGTCAATGAATTGTATTTTAGTAATCTT    2100
   GCAATTCTAGATCTAGCTATTTGTTGTTCTCCTTTCAACCAAACTACTTCTTCAATTTGT    2160
   CTAACAAAAATATGTCAAAAAGGTATGAACATGCTTAATCGGAGATCTTTATTGATTCTA    2220
   CTTCAGCTACTCTAAAAAAAAATCTTTTTTCCATTAAGCCCAAGTCGAGATAGGAGAAAA    2280
   ATATTATTAGAGAGATTATTAATTTAATGACATTTTACTCTAGTTTTTTTATCAAAATAAG    2340
   GGAATAATATCCTGTTATTTAACTACCTTTTAAGCATTATGGGTGGAAAGTAGAAAGAAG    2400
   AAACATAACAGAACAGACAGTAAGTTATGCTTTAATGAGTAGATCTGTATAGGATTACAT    2460
   ATTTGTTTGACTTTTCGGTGTTTCGATTAGAAAACTTACAAGTTTTTAATACATGTATCA    2520
   TTTGTTGATTTGTCCGTTTGGCACGTCATCTGTGGTTACAAGTCACATATGAAGTATGTC    2580
   CACGAGACACACCGAATGTCAAGTATAGATTTCTACTTGATCATACACAACTTTATCTGA    2640
   GGTTGATGCCAAATTTAAATGACTACCTAAAGCTGATATTTAAACATTAATCTTGTACA    2700
   CGAAAACATTATTCCTATTACTGTTTTCTTTACCTTTACCTTATAGACTTTTTTGGCAGA    2760
   AAAAAGTTAGACAGATACATTTGATGATGTTTACCATTCTCATTCTCTCTTTATTTTATT    2820
   TTCTTTACATTCACACGCACAATAATTTTCTTGTAGGTTCCTTATATGCCATATGCACAT    2880
   AGACGAATCTAGGATTTGATATTTACAAGTTTCTATGTCGACGTCATATTAATATCAATA    2940
   ATAATTAGATTGACAATCACATATTTATAATATTAAGTCGATAACTTTCTTCTTTGTATA    3000
   GGTTGGAAAAGTAATGGTAAACGAGCAGGACTCCTTTTTCTTTTTTTTGTAAATAATTAA    3060
   CAGTTGTGAGATTTTATGTTTGTGACTTCATGTCATAAACATTTTGATGTGTGATTAAGA    3120
```

FIGURE 5a

```
TTGACATTTCCAATTGTGCGAGTCTAAAATTACTATATGTGAAAATAGTGATATTATTGA  3180
TTATTCGTATTTTTTCATCTTCTTTCTCCTGTTAAAGTTTTATCTACTTTTTATTCATCA  3240
GGTCTTGAGAAAAAGTAGAATCATGGAAAAACGAAAAGATATTGAAGAAGCAAACAACTC  3300
                      M  E  K  R  K  D  I  E  E  A  N  N  S    13
ATTGGTATGTTATTTTATAGAGTAAACTGTAAAGTATTGAATTATAGATATGTGGCTTTA  3360
   L                                                              14
AAATGTATTATTTTGGCAGGTGTTATTTTCTGCTCTTAGCAAGGACATTGCCAATGTTCT  3420
                    V  L  F  S  A  L  S  K  D  I  A  N  V  L    28
AATTTTCCTAGAGAATGAGGAAAATCAAAAAGCTCTTGACAAAGATCAAGTTGAAAAGCT  3480
 I  F  L  E  N  E  E  N  Q  K  A  L  D  K  D  Q  V  E  K  L     48
AAAATTGAAAATGGCATTTATTTGTACATATGTTCAGCTTTCTTATTCCGATTTTGAGCA  3540
 K  L  K  M  A  F  I  C  T  Y  V  Q  L  S  Y  S  D  F  E  Q     68
GTTTGAAGATATAATGACTAGAAATAGACAAGAGGTTGAGAATCTGCTTCAATCACTTTT  3600
 F  E  D  I  M  T  R  N  R  Q  E  V  E  N  L  L  Q  S  L  L     88
GGATGATGATGTCCTTACTAGCCTCACCAGTAATATGGATGACTGTATCAGCTTGTATCA  3660
 D  D  D  V  L  T  S  L  T  S  N  M  D  D  C  I  S  L  Y  H    108
TCGTTCTTATAAATCAGATGCCATCATGATGGATGAGCAATTGGACTTCCTCCTCTTGAA  3720
 R  S  Y  K  S  D  A  I  M  M  D  E  Q  L  D  F  L  L  L  N    128
TCTGTATCATCTATCCAAGCATCACGCTGAAAAGATATTTCCTGGAGTGACTCAATATGA  3780
 L  Y  H  L  S  K  H  H  A  E  K  I  F  P  G  V  T  Q  Y  E    148
AGTTCTTCAGAATGTATGTGGCAACATAAGAGATTTCCATGGGTTGATACTGAATGGTTG  3840
 V  L  Q  N  V  C  G  N  I  R  D  F  H  G  L  I  L  N  G  C    168
CATTAAGCATGAGATGGTTGAGAATGTCTTACCTCTGTTTCAACTCATGGCTGAAAGAGT  3900
 I  K  H  E  M  V  E  N  V  L  P  L  F  Q  L  M  A  E  R  V    188
AGGACACTTCCTTTGGGAGGATCAGACTGATGAAGACTCTCGGCTCTCCGAGCTAGATGA  3960
 G  H  F  L  W  E  D  Q  T  D  E  D  S  R  L  S  E  L  D  E    208
GGATGAACACAATGATAGAGACTCTCGACTCTTCCAGCTAACACATCTACTCTTGAAGAT  4020
 D  E  H  N  D  R  D  S  R  L  F  Q  L  T  H  L  L  L  K  I    228
TGTTCCAACTGAACTGGAGGTTATGCACATATGTTATACAAATTTGAAAGCTTCAACTTC  4080
 V  P  T  E  L  E  V  M  H  I  C  Y  T  N  L  K  A  S  T  S    248
AGCAGAAGTTGGACGCTTCATTAAGAAGCTCCTGGAAACCTCACCGGATATTCTCAGAGA  4140
 A  E  V  G  R  F  I  K  K  L  L  E  T  S  P  D  I  L  R  E    268
ATATATCATTCAACTACAAGAGCATATGTTAACTGTTATTCCCCCTAGCACTTTAGGGGC  4200
 Y  I  I  Q  L  Q  E  H  M  L  T  V  I  P  P  S  T  L  G  A    288
TCGAAACATTCATGTCATGATGGAATTCCTATTACTTATTCTTTCTGATATGCCCAAGGA  4260
 R  N  I  H  V  M  M  E  F  L  L  L  I  L  S  D  M  P  K  D    308
CTTTATTCATCATGACAAACTTTTTGATCTCTTGGCTCATGTTGGAACACTTACCAGGGA  4320
 F  I  H  H  D  K  L  F  D  L  L  A  H  V  G  T  L  T  R  E    328
GGTATCGACTCTTGTACGTGACTTGGAAGAGAAATTAAGGAATAAAGAGGGTAATAACCA  4380
 V  S  T  L  V  R  D  L  E  E  K  L  R  N  K  E  G  N  N  Q    348
AACAAATTGTGCAACCCTAGACTTGCTGGAAAATATTGAACTCCTCAAGAAAGATCTCAA  4440
 T  N  C  A  T  L  D  L  L  E  N  I  E  L  L  K  K  D  L  K    368
ACATGTTTATCTGAAAGCCCCAAATTCATCTCAATGTTGCTTCCCCATGAGTGATGGACC  4500
 H  V  Y  L  K  A  P  N  S  S  Q  C  C  F  P  M  S  D  G  P    388
ACTCTTCATGCATCTTCTACACATGCACTTAAATGATTTGCTAGATTCTAATGCTTATTC  4560
 L  F  M  H  L  L  H  M  H  L  N  D  L  L  D  S  N  A  Y  S    408
AATTTCTTTGATAAAGGAAGAAATCGAGTTGGTGAGTCAAGAACTGGAATTCATAAGATC  4620
 I  S  L  I  K  E  E  I  E  L  V  S  Q  E  L  E  F  I  R  S    428
ATTCTTTGGGGATGCTGCTGAGCAAGGATTGTATAAAGATATCTGGGCACGTGTTCTAGA  4680
 F  F  G  D  A  A  E  Q  G  L  Y  K  D  I  W  A  R  V  L  D    448
TGTGGCTTATGAGGCAAAAGATGTCATAGATTCAATTATTGTTCGAGATAATGGTCTCTT  4740
 V  A  Y  E  A  K  D  V  I  D  S  I  I  V  R  D  N  G  L  L    468
ACATCTTATTTTCTCACTTCCCATTACCATAAAGAAGATCAAACTTATCAAAGAAGAGAT  4800
 H  L  I  F  S  L  P  I  T  I  K  K  I  K  L  I  K  E  E  I    488
```

FIGURE 5b

```
CTCTGCTTTAGATGAGAACATTCCCAAGGACAGAGGTCTAATCGTTGTGAACTCTCCCAA   4860
   S  A  L  D  E  N  I  P  K  D  R  G  L  I  V  V  N  S  P  K    508
GAAACCAGTTGAGAGAAAGTCATTGACAACTGATAAATAATTGTAGGTTTTGAGGAGGA   4920
   K  P  V  E  R  K  S  L  T  T  D  K  I  I  V  G  F  E  E      528
GACAAACTTGATACTTAGAAAGCTCACCAGTGGACCCGCAGATTTAGATGTCATTTCGAT   4980
   T  N  L  I  L  R  K  L  T  S  G  P  A  D  L  D  V  I  S  I   548
CACCGGTATGCCGGGTTCAGGTAAAACTACTTTGGCATACAAAGTATACAATGATAAGTC   5040
   T  G  M  P  G  S  G  K  T  T  L  A  Y  K  V  Y  N  D  K  S   568
AGTTTCTAGACATTTTGACCTTCGTGCATGGTGCACGGTCGATCAAGGATATGACGACAA   5100
   V  S  R  H  F  D  L  R  A  W  C  T  V  D  Q  G  Y  D  D  K   588
GAAGTTGTTGGATACAATTTTCAGTCAAGTTAGTGGCTCAGATTCAAATTTGAGTGAGAA   5160
   K  L  L  D  T  I  F  S  Q  V  S  G  S  D  S  N  L  S  E  N   608
TATTGATGTTGCTGATAAATTGCGGAAACAACTGTTTGGAAAGAGGTATCTTATTGTCTT   5220
   I  D  V  A  D  K  L  R  K  Q  L  F  G  K  R  Y  L  I  V  L   628
AGATGATGTGTGGGATACTACTACATTGGATGAGTTGACAAGACCTTTTCCTGAAGCTAA   5280
   D  D  V  W  D  T  T  T  L  D  E  L  T  R  P  F  P  E  A  K   648
GAAAGGAAGTAGGATTATTTTGACAACTCGAGAAAAGGAAGTGGCTTTGCATGGAAAGCT   5340
   K  G  S  R  I  I  L  T  T  R  E  K  E  V  A  L  H  G  K  L   668
GAACACTGATCCTCTTGACCTTCGATTGCTAAGACCAGATGAAAGTTGGGAACTTTTAGA   5400
   N  T  D  P  L  D  L  R  L  L  R  P  D  E  S  W  E  L  L  E   688
GAAAAGGACATTTGGTAATGAGAGTTGCCCTGATGAACTATTAGATGTCGGTAAAGAAAT   5460
   K  R  T  F  G  N  E  S  C  P  D  E  L  L  D  V  G  K  E  I   708
AGCCGAAAATTGTAAAGGGCTTCCTTTGGTGGCTGATCTGATTGCTGGAGTCATTGCTGG   5520
   A  E  N  C  K  G  L  P  L  V  A  D  L  I  A  G  V  I  A  G   728
GAGGGAAAAGAAAAGGAGTGTGTGGCTTGAAGTTCAAAGTAGTTTGAGTTCTTTTATTTT   5580
   R  E  K  K  R  S  V  W  L  E  V  Q  S  S  L  S  S  F  I  L   748
GAACAGTGAAGTGGAAGTGATGAAAGTTATAGAATTAAGTTATGACCATTTACCACATCA   5640
   N  S  E  V  E  V  M  K  V  I  E  L  S  Y  D  H  L  P  H  H   768
CCTCAAGCCATGCTTGCTTCACTTTGCAAGTTGGCCGAAGGACACTCCTTTGACAATCTA   5700
   L  K  P  C  L  L  H  F  A  S  W  P  K  D  T  P  L  T  I  Y   788
TTTGTTGACTGTTTATTTGGGTGCTGAAGGATTTGTGGAAAAGACGGAGATGAAGGGTAT   5760
   L  L  T  V  Y  L  G  A  E  G  F  V  E  K  T  E  M  K  G  I   808
AGAAGAAGTGGTGAAGATTTATATGGATGATTTAATTTCCAGTAGCTTGGTAATTTGTTT   5820
   E  E  V  V  K  I  Y  M  D  D  L  I  S  S  S  L  V  I  C  F   828
CAATGAGATAGGTGATATACTGAATTTCCAAATTCATGATCTTGTGCATGACTTTTGTTT   5880
   N  E  I  G  D  I  L  N  F  Q  I  H  D  L  V  H  D  F  C  L   848
GATAAAAGCAAGAAAGGAAAATTTGTTTGATCGGATAAGATCAAGTGCTCCATCAGATTT   5940
   I  K  A  R  K  E  N  L  F  D  R  I  R  S  S  A  P  S  D  L   868
GTTGCCTCGTCAAATTACCATTGATTATGATGAGGAGGAGGAGCACTTTGGGCTTAATTT   6000
   L  P  R  Q  I  T  I  D  Y  D  E  E  E  E  H  F  G  L  N  F   888
TGTCATGTTCGATTCAAATAAGAAAAGGCATTCTGGTAAACACCTCTATTCTTTGAGGAT   6060
   V  M  F  D  S  N  K  K  R  H  S  G  K  H  L  Y  S  L  R  I   908
AAATGGAGACCAGCTGGATGACAGTGTTTCTGATGCATTTCACCTAAGACACTTGAGGCT   6120
   N  G  D  Q  L  D  D  S  V  S  D  A  F  H  L  R  H  L  R  L   928
TATTAGAGTGTTGGACCTGGAACCCTCTTTAATCATGGTGAATGATTCTTTGCTGAATGA   6180
   I  R  V  L  D  L  E  P  S  L  I  M  V  N  D  S  L  L  N  E   948
AATATGCATGTTGAATCATTTGAGGTACTTAAGAATTCGGACACAAGTTAAATATCTGCC   6240
   I  C  M  L  N  H  L  R  Y  L  R  I  R  T  Q  V  K  Y  L  P   968
TTTCTCTTTCTCAAACCTCTGGAATCTAGAAAGTCTGTTTGTGTCTAACAAAGGATCAAT   6300
   F  S  F  S  N  L  W  N  L  E  S  L  F  V  S  N  K  G  S  I   988
CTTGGTACTATTACCGAGAATTTTGGATCTTGTAAAGTTGCGAGTGCTGTCCGTGGGTGC   6360
   L  V  L  L  P  R  I  L  D  L  V  K  L  R  V  L  S  V  G  A  1008
```

FIGURE 5c

```
TTGTTCTTTCTTTGATATGGATGCAGATGAATCAATATTGATAGCAAAGGACACAAAGTT    6420
  C  S  F  F  D  M  D  A  D  E  S  I  L  I  A  K  D  T  K  L   1028
AGAGAACTTGAGAATATTAGGGGAACTGTTGATTTCCTATTCGAAAGATACAATGAATAT    6480
  E  N  L  R  I  L  G  E  L  L  I  S  Y  S  K  D  T  M  N  I   1048
TTTCAAAAGGTTTCCCAATCTTCAGGTGCTTCAGTTTGAACTCAAGGAGTCATGGGATTA    6540
  F  K  R  F  P  N  L  Q  V  L  Q  F  E  L  K  E  S  W  D  Y   1068
TTCAACAGAGCAACATTGGTTCCCGAAATTGGATTGCCTAACTGAACTAGAAACACTCTG    6600
  S  T  E  Q  H  W  F  P  K  L  D  C  L  T  E  L  E  T  L  C   1088
TGTAGGTTTTAAAAGTTCAAACACAAACCACTGTGGGTCCTCTGTTGCGACAAATCGGCC    6660
  V  G  F  K  S  S  N  T  N  H  C  G  S  S  V  A  T  N  R  P   1108
GTGGGATTTTCACTTCCCTTCAAATTTGAAAGAACTGTTGTTGTATGACTTTCCTCTGAC    6720
  W  D  F  H  F  P  S  N  L  K  E  L  L  L  Y  D  F  P  L  T   1128
ATCCGATTCACTATCAACAATAGCGAGACTGCCCAACCTTGAAAATTTGTCCCTTTATGA    6780
  S  D  S  L  S  T  I  A  R  L  P  N  L  E  N  L  S  L  Y  D   1148
TACAATCATCCAGGGAGAAGAATGGAACATGGGGGAGGAAGACACTTTTGAGAATCTCAA    6840
  T  I  I  Q  G  E  E  W  N  M  G  E  E  D  T  F  E  N  L  K   1168
ATTTTTGAACTTGCGTCTACTGACTCTTTCCAAGTGGGAGGTTGGAGAGGAATCCTTCCC    6900
  F  L  N  L  R  L  L  T  L  S  K  W  E  V  G  E  E  S  F  P   1188
CAATCTTGAGAAATTAAAACTGCAGGAATGTGGTAAGCTTGAGGAGATTCCACCTAGTTT    6960
  N  L  E  K  L  K  L  Q  E  C  G  K  L  E  E  I  P  P  S  F   1208
TGGAGATATTTATTCATTGAAATTTATCAAAATTGTAAAGAGTCCTCAACTTGAAGATTC    7020
  G  D  I  Y  S  L  K  F  I  K  I  V  K  S  P  Q  L  E  D  S   1228
TGCTCTCAAGATTAAGAAATACGCTGAAGATATGAGAGGAGGGAACGAGCTTCAGATCCT    7080
  A  L  K  I  K  K  Y  A  E  D  M  R  G  G  N  E  L  Q  I  L   1248
TGGCCAGAAGAATATCCCCTTATTTAAGTAGCATTTTGGTTGAACTTTGCTTGGTGATAT    7140
  G  Q  K  N  I  P  L  F  K  ---                                1257
TGTATATGATTAAAATATCCTGTGATGAGATTCCTCTTAGTTTCTTTTAACAAAAAATAT    7200
AATTTTTATAAGTACACATATCGTTTGTTAATTTGTCCATTTGTGATTGCAAGTCACACA    7260
TGAGGTATGTTCGTATTATGGGTTTCAACTTGATCAGACGTAATTTTAAGATAAGTGCTT    7320
ATATGATGTTGCATGCCAGATGGAAGTGACTATGTGAAGTTTATATTTTAAACATTAATC    7380
TTGTATACCAAACTACTATTCCTATGCTATGTTGTTTGCCATTGTCGTTCTCTCTTTATT    7440
TTTTTTCTTTCCATTCACACACACATTAATTTTCTAGTAGACCGCATATTACTACATCTG    7500
TATTGTCCGTATACAAGACGAATCCAGGATTTGATGTTTACAAGTATTTGTGAAGAATCC    7560
AGGATTTGATGTTTACAAGACAATTAGATTCATATATGTATAGGATTTTGACAGAAACTG    7620
AGGGATTCACATGACAATTACTCTGTGGATTTGCCTTTGGCTGTCCAAACCTCCTTTGTG    7680
TCTAACTTCGTCTGAAGTCCCATTTATATGCTCAAAGCTCAGTCAAGGTACTGATTCAAA    7740
AGCTAGGCTGTGAAGTAAACTTTAAAATGATATTGCTGCAAAGTCGCTCAACAAAGGGTC    7800
ATAACCATCACTACAACTACACAAGCTCAAGCAAGTAAACGCGGGTGAAAGATTAACATA    7860
GATCGCTATCCCCTGCAAAAGCTAAGGAAAGCATCTCTAACTTCTTAGCATGTACTCAAA    7920
CACACGATCTGTAAGGATGCCAGAAAGAGAAAGTTACGTTGCCGCAATTCCTTACAGTGT    7980
TGCACAATGTCCCCAAAACCAACATCACACTACAAAAAAAGGCTCAAATTCTGGGGGTTA    8040
TAATTAGACGGTCAATAACCCCTGCAATTTAGTGTTGTGGAGGTTGAATAAACTCCTCCA    8100
ATTAGGAGTGTCACAATTAAGTCGCGTGGGATTCTTGGCACATCCCGGTAAGGTTAACTA    8160
GCGGGGGTTTTGAACCCCAACCGCATTTCAAACTAGGAGTCGAAACCCCAACGATTTGTG    8220
AACTCGGGGGAGTCAAAAACCCCCGCAATAAATGATTTTTACATTAAAATTAATAGGAGC    8280
TTGGACCCCTGTGATTTATGAAATATAACTTTTTGTAGCATTTGCCAGAAATATTCAATT    8340
TTAGATACTAATAATAAATTAATTAACTAACATGTGCATCATTATTCAAAGGACATATTA    8400
GTATTAAGAAATAATACAATATTCAACACAAAAGTACCCAAACTCAAGATAGGATCAGTT    8460
TATGGAACTTCAACTAGTTTCACTATAATTATTGTCACTAACATCAGCTGGCTGCAAAGG    8520
AGAATACATAATAAGTGACTTTATCCAAACTCAAAATCATGGCTGAATGTAGTAAAACAC    8580
CAAAGATTATAATAATTTCCATTAATTATCATATACTACACAACAACAAACTTAAAACAA    8640
TATAGAAAGGATTAAACCATTTACACAAGCAATGATTCTATACCATTTCAAAACGACAA    8700
CATACTGTACTACTAAACAAGACACCATCAAACTGATTTGGACAAATATTAACAATAGTT    8760
```

FIGURE 5d

```
AAAACATGAACAAAGAATCTCAGGTTTCTTGTCAGTAGAAAAGAGACAGACTAGGAACTG    8820
GAGTGCTATTTTTCTTATAAGAGACAATTAATGTTTACTTCTTTATATTTTGACTATAAG    8880
TTGATTGGTTATAATGTTTACGAGGTTGTATATAATCCGATGTTCAATGATATGACTTTC    8940
CTATTGACTGAAATGCTTGAACGCAAACAGTATATCTAGATTAAGAATGAGGACGAATTA    9000
CCTCTAGAGGCATGGGTAATGGAAGCATAACTCCTTGATAATGGTTGTTAGCCCACTGCA    9060
AGTCACAAAACAAAACATCCGTAATATTAACATACTAAGGTTGTAAGCACTAAACGACAA    9120
CAACTATGCCTCAATCCCAACTAAGTTGGAATCGACTATATGAATACTCACAATTTCGAT    9180
TTATAGACAAAGATACTAGTAGAAATGACGTCTTTCCTTTCTATGTTAACACTTGGACAG    9240
AGAATGTTAAAGACTTACAACAACAGAAAAGAGTTAAAATCATTTAATTGAGCAAGGATT    9300
TCAAAACGACAACACAATATACTCAATTTTTCGACGGAAACAACTGGTTGGACAACAGTG    9360
CTATTTGTAACTCCAATGAACAACACTGCAACGTACATGTATCTCATTGCACTAAATAAA    9420
TCCCGTTGAGAGTAACATATCAATAGTTACGAACAATATGATCACGACAAAGGATTGTAA    9480
GTACCACAGGACAAGTCATGCTTGCATGAAAAACGGATATGTAAAGAACCAAAATCCTGC    9540
TGCTGAAATAAGCAGTTATGATTATCCAAAAATCATGAATACACATGCACTTGAGTTTGT    9600
TCCAAGAAAAACACAACCAACTACTGTCGCAAGTGAAGATTCAAAAGTGACTATTGATGT    9660
TAATTCTTCCACAAGGTTGAATAATTTTGTCACTATAGGATTTAAGACGAAGAAGAAACA    9720
GGCGACAATTTTGTAAGCATAGACCTTCTTATGCAACTATGAGCTGGTATGCTATTCATT    9780
TTCTTTACTCGTAAAAATCGTTGATACTAAAGAATGCCAATCCAGTCCTGCTGAATAGGC    9840
GCCAGGTGACTGGTTGCTGTTAATAATTTT-3'                               9870
```

FIGURE 5e

```
MEKRKDIEEA NNSLVLFSAL SKDIANVLIF LENEENQKAL DKDQVEKLKL KMAFICTYVQ
LSYSDFEQFE DIMTRNRQEV ENLLQSLLDD DVLTSLTSNM DDCISLYHRS YKSDAIMMDE
QLDFLLLNLY HLSKHHAEKI FPGVTQYEVL QNVCGNIRDF HGLILNGCIK HEMVENVLPL
FQLMAERVGH FLWEDQTDED SRLSELDEDE HNDRDSRLFQ LTHLLLKIVP TELEVMHICY
TNLKASTSAE VGRFIKKLLE TSPDILREYI IQLQEHMLTV IPPSTLGARN IHVMMEFLLL
ILSDMPKDFI HHDKLFDLLA HVGTLTREVS TLVRDLEEKL RNKEGNNQTN CATLDLLENI
ELLKKDLKHV YLKAPNSSQC CFPMSDGPLF MHLLHMHLND LLDSNAYSIS LIKEEIELVS
QELEFIRSFF GDAAEQGLYK DIWARVLDVA YEAKDVIDSI IVRDNGLLHL IFSLPITIKK
IKLIKEEISA LDENIPKDRG LIVVNSPKKP VERKSLTTDK IIVGFEEETN LILRKLTSGP
ADLDVISITG MPGSGKTTLA YKVYNDKSVS RHFDLRAWCT VDQGYDDKKL LDTIFSQVSG
SDSNLSENID VADKLRKQLF GKRYLIVLDD VWDTTTLDEL TRPFPEAKKG SRIILTTREK
EVALHGKLNT DPLDLRLLRP DESWELLEKR TFGNESCPDE LLDVGKEIAE NCKGLPLVAD
LIAGVIAGRE KKRSVWLEVQ SSLSSFILNS EVEVMKVIEL SYDHLPHHLK PCLLHFASWP
KDTPLTIYLL TVYLGAEGFV EKTEMKGIEE VVKIYMDDLI SSSLVICFNE IGDILNFQIH
DLVHDFCLIK ARKENLFDRI RSSAPSDLLP RQITIDYDEE EEHFGLNFVM FDSNKKRHSG
KHLYSLRING DQLDDSVSDA FHLRHLRLIR VLDLEPSLIM VNDSLLNEIC MLNHLRYLRI
RTQVKYLPFS FSNLWNLESL FVSNKGSILV LLPRILDLVK LRVLSVGACS FFDMDADESI
LIAKDTKLEN LRILGELLIS YSKDTMNIFK RFPNLQVLQF ELKESWDYST EQHWFPKLDC
LTELETLCVG FKSSNTNHCG SSVATNRPWD FHFPSNLKEL LLYDFPLTSD SLSTIARLPN
LENLSLYDTI IQGEEWNMGE EDTFENLKFL NLRLLTLSKW EVGEESFPNL EKLKLQECGK
LEEIPPSFGD IYSLKFIKIV KSPQLEDSAL KIKKYAEDMR GGNELQILGQ KNIPLFK
//
```

FIGURE 7A

```
MAFICTYVQL SYSDFEQFED IMTRNRQEVE NLLQSLLDDD VLTSLTSNMD DCISLYHRSY
KSDAIMMDEQ LDFLLLNLYH LSKHHAEKIF PGVTQYEVLQ NVCGNIRDFH GLILNGCIKH
EMVENVLPLF QLMAERVGHF LWEDQTDEDS RLSELDEDEH NDRDSRLFQL THLLLKIVPT
ELEVMHICYT NLKASTSAEV GRFIKKLLET SPDILREYII QLQEHMLTVI PPSTLGARNI
HVMMEFLLLI LSDMPKDFIH HDKLFDLLAH VGTLTREVST LVRDLEEKLR NKEGNNQTNC
ATLDLLENIE LLKKDLKHVY LKAPNSSQCC FPMSDGPLFM HLLHMHLNDL LDSNAYSISL
IKEEIELVSQ ELEFIRSFFG DAAEQGLYKD IWARVLDVAY EAKDVIDSII VRDNGLLHLI
FSLPITIKKI KLIKEEISAL DENIPKDRGL IVVNSPKKPV ERKSLTTDKI IVGFEEETNL
ILRKLTSGPA DLDVISITGM PGSGKTTLAY KVYNDKSVSR HFDLRAWCTV DQGYDDKKLL
DTIFSQVSGS DSNLSENIDV ADKLRKQLFG KRYLIVLDDV WDTTTLDELT RPFPEAKKGS
RIILTTREKE VALHGKLNTD PLDLRLLRPD ESWELLEKRT FGNESCPDEL LDVGKEIAEN
CKGLPLVADL IAGVIAGREK KRSVWLEVQS SLSSFILNSE VEVMKVIELS YDHLPHHLKP
CLLHFASWPK DTPLTIYLLT VYLGAEGFVE KTEMKGIEEV VKIYMDDLIS SSLVICFNEI
GDILNFQIHD LVHDFCLIKA RKENLFDRIR SSAPSDLLPR QITIDYDEEE EHFGLNFVMF
DSNKKRHSGK HLYSLRINGD QLDDSVSDAF HLRHLRLIRV LDLEPSLIMV NDSLLNEICM
LNHLRYLRIR TQVKYLPFSF SNLWNLESLF VSNKGSILVL LPRILDLVKL RVLSVGACSF
FDMDADESIL IAKDTKLENL RILGELLISY SKDTMNIFKR FPNLQVLQFE LKESWDYSTE
QHWFPKLDCL TELETLCVGF KSSNTNHCGS SVATNRPWDF HFPSNLKELL LYDFPLTSDS
LSTIARLPNL ENLSLYDTII QGEEWNMGEE DTFENLKFLN LRLLTLSKWE VGEESFPNLE
KLKLQECGKL EEIPPSFGDI YSLKFIKIVK SPQLEDSALK IKKYAEDMRG GNELQILGQK
NIPLFK
//
```

FIGURE 7B

SEQUENCE LISTING

<160> NUMBER OF SEQ ID NOS: 19

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: PST1-PRIMER

```
<220> FEATURE:
<221> NAME/KEY: variation
<222> LOCATION: (17)
<223> OTHER INFORMATION: A, T, G or C
<220> FEATURE:
<221> NAME/KEY: variation
<222> LOCATION: (18)
<223> OTHER INFORMATION: A, T, G or C

<400> SEQUENCE: 1
gactgcgtac atgcagnn                                                      18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Mse1 primer
<220> FEATURE:
<221> NAME/KEY: variation
<222> LOCATION: (17)
<223> OTHER INFORMATION: A, T, G or C
<220> FEATURE:
<221> NAME/KEY: variation
<222> LOCATION: (18)
<223> OTHER INFORMATION: A, T, G or C
<220> FEATURE:
<221> NAME/KEY: variation
<222> LOCATION: (19)
<223> OTHER INFORMATION: A, T, G or C

<400> SEQUENCE: 2
gatgagtcct gagtaannn                                                     19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Pst1
      adapter

<400> SEQUENCE: 3
ctcgtagact gcgtacatgc a                                                  21

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Pst1
      adapter

<400> SEQUENCE: 4
tgtacgcagt ctac                                                          14

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Mse1
      adapter

<400> SEQUENCE: 5
gacgatgagt cctgag                                                        16

<210> SEQ ID NO 6
<211> LENGTH: 14
```

```
<212> TYPE: DNA
<213> ORGANISM: Artificial Sequence
<220> FEATURE:
<223> OTHER INFORMATION: Description of Artificial Sequence: Mse1
      adapter

<400> SEQUENCE: 6
tactcaggac tcat                                                      14

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Pst1
      primer

<400> SEQUENCE: 7
gactgcgtac atgcag                                                    16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Mse1 primer

<400> SEQUENCE: 8
gatgagtcct gagtaa                                                    16

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Pst1 primer

<400> SEQUENCE: 9
gactgcgtac atgcagga                                                  18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Mse1 primer

<400> SEQUENCE: 10
gatgagtcct gagtaatct                                                 19

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: EcoR1
      primer

<400> SEQUENCE: 11
gactgcgtac caattc                                                    16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Mse1 primer
```

<400> SEQUENCE: 12
gatgagtcct gagtaa                                                     16

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: primer S21

<400> SEQUENCE: 13
ccaaggacag aggtctaatc g                                               21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: primer S22

<400> SEQUENCE: 14
ttgaggtgat gtggtaaatg g                                               21

<210> SEQ ID NO 15
<211> LENGTH: 9870
<212> TYPE: DNA
<213> ORGANISM: Mi resistance gene

<400> SEQUENCE: 15
ttttcctctt catataactt tttccttaac ccctctcatg aataatataa ttgatgtgga       60
taaagtatta tcctttatga taaataacga aatttaataa tttaaagggt gcaaatctat      120
aaaatggaga cgcacattga taatgtcctc ttgattatta ttaaagaatt actctagctt      180
cacaaattta aattcattaa tgcttaatta catgataaaa actttagttg ttcttttac       240 atggtttgct aactttaatt tttttcttc atattcttca tttgtttatt attatttct        300 aattacttat ttaacttta tactcttaat attcataact ctcatcttt catattcata        360 acctccaaat atttaaacta aactttaag atatcttttg atatttgttc aataatataaat     420 tcaacttctt tatcttatga aaccccttacc aagattatta ggctattatt ttttattcta    480
tagtaaaaac aaatgatgaa gattcttgaa ttttatagga tatgaaagaa gtcgataaaa      540
tctcagagag ttatgtacta attttgtact tatttttca tctatatata cataaatctt      600
ataagaataa tgtctatatt gtattttttt cttaaatatt atgtttcttt ttaattttt      660 ttcactctgt tagacttctt aatttagttt tctatgaatg ttttattgcc gtaagtcttt     720
gaattttgta attgttacat tttattattc attacgattt acatatatat ttccatgaga     780
tttggtcatt ctaacgtatc tataaaaatt cacatgaaac acacgtgtga agcgcatcct     840
cagaaaaact agtgtatata tatatatata tatatatata tatatatata tatatatata     900
tatatatata tatatatata tatatattat tcttattaaa aaagaatgtc cttatttcat     960
ttttaatctg gttaaaaaag aataatctct ttccttttttt gacaatatt  taactttaac   1020 tttccacgta acatgttaa gacaacaaaa ttaaatgaca ttttaatctt gtaacataga    1080
aaagtaacat atgataattg tcgttgtccc taaacatgat agatgtataa ttcaaaagtc     1140
aatgaattgt attttagtat tatattatga atgaacaaac tgtcaagatg tgtatatata    1200
tatatttttt attcttgtta atttggcctt tcaagtaatt aattcattgt taggcagttg    1260

-continued

| | | | | |
|---|---|---|---|---|
| aattaataat | ctcttttagg | aatcttccca | tgtgaataac | aagacttata ataataataa 1320 |
| taaagtccag | atcttgtttc | aattggatca | tttggcaaac | aattactctg tttctgaaac 1380 |
| aaggaatagg | gcttctaata | ttgtagggga | tttttttttc | ttcattaatt tatacttatg 1440 |
| atattaatta | ttgtttttga | gtacatattt | taaactctgt | tgtttatttt tctgcaaagt 1500 |
| ttctccggtt | atattgaaca | tatacacata | tagtacacat | atttattgta aaaaaaataa 1560 |
| ttattatact | ccatttcaag | aaattatgtt | ttgatattat | atattaaatt ctataatgtg 1620 |
| gaaattgtca | atgtctacaa | tgtgtttgat | gaaatgacaa | ccacttgttt ttatctgcaa 1680 |
| cagtataaaa | attggctttg | cttcttttag | attaatataa | tatttacag gtcacatatt 1740 |
| atatttatat | tgtgaaagac | aagagatatt | gattaaaaaa | agacttatgg gtttgtatt 1800 |
| taatatttca | ttcttcttca | ttactaaaag | acttgtatcg | tatatttcaa ctactacact 1860 |
| tgttttctta | tccaatagct | tcaacattat | ttctcaaaca | aagggttctc tagctaaact 1920 |
| tcagcctgtg | taaaggtaac | atcttcttta | ttcacagcat | aataacaatg aatttggtcg 1980 |
| atgtttgaag | taagcttgaa | attttctctt | tctaagtttg | tttgatccat ttagattctt 2040 |
| ttaaatactt | ttggtattta | aaggacttgt | gaagtcaatg | aattgtattt tagtaatctt 2100 |
| gcaattctag | atctagctat | ttgttgttct | cctttcaacc | aaactacttc ttcaatttgt 2160 |
| ctaacaaaaa | tatgtcaaaa | aggtatgaac | atgcttaatc | ggagatcttt attgattcta 2220 |
| cttcagctac | tctaaaaaaa | aatcttttt | ccattaagcc | caagtcgaga taggagaaaa 2280 |
| atattattag | agagattatt | aatttaatga | cattttactc | tagttttta tcaaaataag 2340 |
| ggaataatat | cctgttattt | aactacctt | taagcattat | gggtggaaag tagaaagaag 2400 |
| aaacataaca | gaacagacag | taagttatgc | tttaatgagt | agatctgtat aggattacat 2460 |
| atttgtttga | cttttcggtg | tttcgattag | aaaacttaca | agttttaat acatgtatca 2520 |
| tttgttgatt | tgtccgtttg | gcacgtcatc | tgtggttaca | agtcacatat gaagtatgtc 2580 |
| cacgagacac | accgaatgtc | aagtatagat | ttctacttga | tcatacacaa ctttatctga 2640 |
| ggttgatgcc | aaatttaaat | gactacctaa | agctgatatt | ttaaacatta atcttgtaca 2700 |
| cgaaaacatt | attcctatta | ctgttttctt | tacctttacc | ttatagactt ttttggcaga 2760 |
| aaaaagttag | acagatacat | ttgatgatgt | ttaccattct | cattctctct ttattttatt 2820 |
| ttctttacat | tcacacgcac | aataattttc | ttgtaggttc | cttatatgcc atatgcacat 2880 |
| agacgaatct | aggatttgat | atttacaagt | ttctatgtcg | acgtcatatt aatatcaata 2940 |
| ataattagat | tgacaatcac | atatttataa | tattaagtcg | ataactttct tctttgtata 3000 |
| ggttggaaaa | gtaatggtaa | acgagcagga | ctccttttc | ttttttttgt aaataattaa 3060 |
| cagttgtgag | attttatgtt | tgtgacttca | tgtcataaac | attttgatgt gtgattaaga 3120 |
| ttgacatttc | caattgtgcg | agtctaaaat | tactatatgt | gaaaatagtg atattattga 3180 |
| ttattcgtat | tttttcatct | tctttctcct | gttaaagttt | tatctacttt ttattcatca 3240 |
| ggtcttgaga | aaaagtagaa | tcatggaaaa | acgaaaagat | attgaagaag caaacaactc 3300 |
| attggtatgt | tattttatag | agtaaactgt | aaagtattga | attatagata tgtggcttta 3360 |
| aaatgtatta | ttttggcagg | tgttattttc | tgctcttagc | aaggacattg ccaatgttct 3420 |
| aattttccta | gagaatgagg | aaaatcaaaa | agctcttgac | aaagatcaag ttgaaaagct 3480 |
| aaaattgaaa | atggcattta | tttgtacata | tgttcagctt | tcttattccg attttgagca 3540 |
| gtttgaagat | ataatgacta | gaaatagaca | agaggttgag | aatctgcttc aatcacttt 3600 |
| ggatgatgat | gtccttacta | gcctcaccag | taatatggat | gactgtatca gcttgtatca 3660 |

-continued

```
tcgttcttat aaatcagatg ccatcatgat ggatgagcaa ttggacttcc tcctcttgaa    3720
tctgtatcat ctatccaagc atcacgctga aaagatattt cctggagtga ctcaatatga    3780
agttcttcag aatgtatgtg caacataag  agatttccat gggttgatac tgaatggttg    3840
cattaagcat gagatggttg agaatgtctt acctctgttt caactcatgg ctgaaagagt    3900
aggacacttc ctttgggagg atcagactga tgaagactct cggctctccg agctagatga    3960
ggatgaacac aatgatagag actctcgact cttccagcta acacatctac tcttgaagat    4020
tgttccaact gaactggagg ttatgcacat atgttataca aatttgaaag cttcaacttc    4080
agcagaagtt ggacgcttca ttaagaagct cctggaaacc tcaccggata ttctcagaga    4140
atatatcatt caactacaag agcatatgtt aactgttatt cccctagca ctttaggggc     4200 tcgaaacatt catgtcatga tggaattcct attacttatt ctttctgata tgcccaagga    4260
ctttattcat catgacaaac tttttgatct cttggctcat gttggaacac ttaccaggga    4320
ggtatcgact cttgtacgtg acttggaaga gaaattaagg aataaagagg gtaataacca    4380
aacaaattgt gcaaccctag acttgctgga aaatattgaa ctcctcaaga agatctcaa     4440 acatgtttat ctgaaagccc caaattcatc tcaatgttgc ttccccatga gtgatggacc    4500
actcttcatg catcttctac acatgcactt aaatgatttg ctagattcta atgcttattc    4560
aatttctttg ataaaggaag aaatcgagtt ggtgagtcaa gaactggaat tcataagatc    4620
attctttggg gatgctgctg agcaaggatt gtataaagat atctgggcac gtgttctaga    4680
tgtggcttat gaggcaaaag atgtcataga ttcaattatt gttcgagata tggtctctt     4740 acatcttatt ttctcacttc ccattaccat aaagaagatc aaacttatca agaagagat     4800 ctctgcttta gatgagaaca ttcccaagga cagaggtcta atcgttgtga actctcccaa    4860
gaaaccagtt gagagaaagt cattgacaac tgataaaata attgtaggtt ttgaggagga    4920
gacaaacttg atacttagaa agctcaccag tggacccgca gatttagatg tcatttcgat    4980
caccggtatg ccgggttcag gtaaaactac tttggcatac aaagtataca atgataagtc    5040
agtttctaga cattttgacc ttcgtgcatg gtgcacggtc gatcaaggat atgacgacaa    5100
gaagttgttg gatacaattt tcagtcaagt tagtggctca gattcaaatt tgagtgagaa    5160
tattgatgtt gctgataaat tgcggaaaca actgtttgga aagaggtatc ttattgtctt    5220
agatgatgtg tgggatacta ctacattgga tgagttgaca agacctttt  ctgaagctaa    5280 gaaaggaagt aggattattt tgacaactcg agaaaaggaa gtggctttgc atggaaagct    5340
gaacactgat cctcttgacc ttcgattgct aagaccagat gaaagttggg aacttttaga    5400
gaaaaggaca tttggtaatg agagttgccc tgatgaacta ttagatgtcg gtaaagaaat    5460
agccgaaaat tgtaaagggc ttcctttggt ggctgatctg attgctggag tcattgctgg    5520
gagggaaaag aaaaggagtg tgtggcttga agttcaaagt agtttgagtt cttttatttt    5580
gaacagtgaa gtggaagtga tgaaagttat agaattaagt tatgaccatt taccacatca    5640
cctcaagcca tgcttgcttc actttgcaag ttggccgaag acactccttt tgacaatcta    5700
tttgttgact gtttatttgg gtgctgaagg atttgtggaa aagacggaga tgaagggtat    5760
agaagaagtg gtgaagattt atatggatga tttaatttcc agtagcttgg taatttgttt    5820
caatgagata ggtgatatac tgaatttcca aattcatgat cttgtgcatg acttttgttt    5880
gataaaagca agaaaggaaa atttgtttga tcggataaga tcaagtgctc catcagattt    5940
gttgcctcgt caaattacca ttgattatga tgaggaggag gagcactttg ggcttaattt    6000
```

-continued

```
tgtcatgttc gattcaaata agaaaaggca ttctggtaaa cacctctatt ctttgaggat      6060
aaatggagac cagctggatg acagtgtttc tgatgcattt cacctaagac acttgaggct      6120
tattagagtg ttggacctgg aaccctcttt aatcatggtg aatgattctt tgctgaatga      6180
aatatgcatg ttgaatcatt tgaggtactt aagaattcgg acacaagtta aatatctgcc      6240
tttctctttc tcaaacctct ggaatctaga aagtctgttt gtgtctaaca aaggatcaat      6300
cttggtacta ttaccgagaa ttttggatct tgtaaagttg cgagtgctgt ccgtgggtgc      6360
ttgttctttc tttgatatgg atgcagatga atcaatattg atagcaaagg cacaaagtt       6420 agagaacttg agaatattag gggaactgtt gatttcctat tcgaaagata caatgaatat      6480
tttcaaaagg tttcccaatc ttcaggtgct tcagtttgaa ctcaaggagt catgggatta      6540
ttcaacagag caacattggt tcccgaaatt ggattgccta actgaactag aaacactctg      6600
tgtaggtttt aaaagttcaa acacaaacca ctgtgggtcc tctgttgcga caaatcggcc      6660
gtgggatttt cacttccctt caaatttgaa agaactgttg ttgtatgact ttcctctgac      6720
atccgattca ctatcaacaa tagcgagact gcccaacctt gaaaatttgt ccctttatga      6780
tacaatcatc cagggagaag aatggaacat gggggaggaa gacacttttg agaatctcaa      6840 attttttgaac ttgcgtctac tgactctttc caagtgggag gttggagagg aatccttccc      6900
caatcttgag aaattaaaac tgcaggaatg tggtaagctt gaggagattc cacctagttt      6960
tggagatatt tattcattga aatttatcaa aattgtaaag agtcctcaac ttgaagattc      7020
tgctctcaag attaagaaat acgctgaaga tatgagagga gggaacgagc ttcagatcct      7080
tggccagaag aatatcccct tatttaagta gcatttttggt tgaactttgc ttggtgatat      7140
tgtatatgat taaaatatcc tgtgatgaga ttcctcttag tttcttttaa caaaaaatat      7200 aattttttata agtacacata tcgtttgtta atttgtccat tgtgattgc aagtcacaca      7260 tgaggtatgt tcgtattatg ggtttcaact tgatcagacg taattttaag ataagtgctt      7320
atatgatgtt gcatgccaga tggaagtgac tatgtgaagt ttatatttta aacattaatc      7380
ttgtatacca aactactatt cctatgctat gttgtttgcc attgtcgttc tctctttatt      7440
ttttttcttt ccattcacac acacattaat tttctagtag accgcatatt actacatctg      7500
tattgtccgt atacaagacg aatccaggat ttgatgttta caagtatttg tgaagaatcc      7560
aggatttgat gtttacaaga caattagatt catatatgta taggattttg acagaaactg      7620
agggattcac atgacaatta ctctgtggat ttgccttttgg ctgtccaaac ctcctttgtg      7680
tctaacttcg tctgaagtcc catttatatg ctcaaagctc agtcaaggta ctgattcaaa      7740
agctaggctg tgaagtaaac tttaaaatga tattgctgca aagtcgctca acaaagggtc      7800
ataaccatca ctacaactac acaagctcaa gcaagtaaac gcgggtgaaa gattaacata      7860
gatcgctatc ccctgcaaaa gctaaggaaa gcatctctaa cttcttagca tgtactcaaa      7920
cacacgatct gtaaggatgc cagaaagaga aagttacgtt gccgcaattc cttacagtgt      7980
tgcacaatgt ccccaaaacc aacatcacac tacaaaaaaa ggctcaaatt ctggggggtta      8040 taattagacg gtcaataacc cctgcaattt agtgttgtgg aggttgaata aactcctcca      8100
attaggagtg tcacaattaa gtcgcgtggg attcttggca catcccggta aggttaacta      8160
gcgggggttt tgaaccccaa ccgcatttca aactaggagt cgaaacccca acgatttgtg      8220
aactcggggg agtcaaaaac ccccgcaata atgatttttt acattaaaat taataggagc      8280
ttggacccct gtgattatg aaatataact ttttgtagca tttgccagaa atattcaatt       8340
ttagatacta ataataaatt aattaactaa catgtgcatc attattcaaa ggacatatta      8400
```

-continued

```
gtattaagaa ataatacaat attcaacaca aaagtaccca aactcaagat aggatcagtt    8460
tatggaactt caactagttt cactataatt attgtcacta acatcagctg gctgcaaagg    8520
agaatacata ataagtgact ttatccaaac tcaaaatcat ggctgaatgt agtaaaacac    8580
caaagattat aataatttcc attaattatc atatactaca caacaacaaa cttaaaacaa    8640
tatagaaaag gattaaacca tttacacaag caatgattct ataccatttc aaaacgacaa    8700
catactgtac tactaaacaa gacaccatca aactgatttg dacaaatatt aacaatagtt    8760
aaaacatgaa caaagaatct caggtttctt gtcagtagaa aagagacaga ctaggaactg    8820
gagtgctatt tttcttataa gagacaatta atgtttactt ctttatattt tgactataag    8880
ttgattggtt ataatgttta cgaggttgta tataatccga tgttcaatga tatgactttc    8940
ctattgactg aaatgcttga acgcaaacag tatatctaga ttaagaatga ggacgaatta    9000
cctctagagg catgggtaat ggaagcataa ctccttgata atggttgtta gcccactgca    9060
agtcacaaaa caaacatccc gtaatattaa catactaagg ttgtaagcac taaacgacaa    9120
caactatgcc tcaatcccaa ctaagttgga atcgactata tgaatactca caatttcgat    9180
ttatagacaa agatactagt agaaatgacg tctttccttt ctatgttaac acttggacag    9240
agaatgttaa agacttacaa caacagaaaa gagttaaaat catttaattg agcaaggatt    9300
tcaaaacgac aacacaatat actcaatttt tcgacggaaa caactggttg dacaacagtg    9360
ctatttgtaa ctccaatgaa caacactgca acgtacatgt atctcattgc actaaataaa    9420
tcccgttgag agtaacatat caatagttac gaacaatatg atcacgacaa aggattgtaa    9480
gtaccacagg acaagtcatg cttgcatgaa aaacggatat gtaaagaacc aaaatcctgc    9540
tgctgaaata agcagttatg attatccaaa aatcatgaat acacatgcac ttgagtttgt    9600
tccaagaaaa acacaaccaa ctactgtcgc aagtgaagat tcaaaagtga ctattgatgt    9660
taattcttcc acaaggttga ataattttgt cactatagga tttaagacga agaagaaaca    9720
ggcgacaatt ttgtaagcat agaccttctt atgcaactat gagctggtat gctattcatt    9780
ttctttactc gtaaaaatcg ttgatactaa agaatgccaa tccagtcctg ctgaataggc    9840
gccaggtgac tggttgctgt taataatttt                                     9870
```

<210> SEQ ID NO 16
<211> LENGTH: 14
<212> TYPE: PRT
<213> ORGANISM: Mi resistance gene deduced amino acid

<400> SEQUENCE: 16

Met Glu Lys Arg Lys Asp Ile Glu Glu Ala Asn Asn Ser Leu
 1               5                  10

<210> SEQ ID NO 17
<211> LENGTH: 1243
<212> TYPE: PRT
<213> ORGANISM: Mi resistance gene deduced amino acid

<400> SEQUENCE: 17

Val Leu Phe Ser Ala Leu Ser Lys Asp Ile Ala Asn Val Leu Ile Phe
 1               5                  10                  15

Leu Glu Asn Glu Glu Asn Gln Lys Ala Leu Asp Lys Asp Gln Val Glu
            20                  25                  30

Lys Leu Lys Leu Lys Met Ala Phe Ile Cys Thr Tyr Val Gln Leu Ser
        35                  40                  45

-continued

```
Tyr Ser Asp Phe Glu Gln Phe Glu Asp Ile Met Thr Arg Asn Arg Gln
     50                  55                  60

Glu Val Glu Asn Leu Leu Gln Ser Leu Leu Asp Asp Val Leu Thr
 65                  70                  75                  80

Ser Leu Thr Ser Asn Met Asp Asp Cys Ile Ser Leu Tyr His Arg Ser
                 85                  90                  95

Tyr Lys Ser Asp Ala Ile Met Met Asp Glu Gln Leu Asp Phe Leu Leu
             100                 105                 110

Leu Asn Leu Tyr His Leu Ser Lys His His Ala Glu Lys Ile Phe Pro
             115                 120                 125

Gly Val Thr Gln Tyr Glu Val Leu Gln Asn Val Cys Gly Asn Ile Arg
     130                 135                 140

Asp Phe His Gly Leu Ile Leu Asn Gly Cys Ile Lys His Glu Met Val
145                 150                 155                 160

Glu Asn Val Leu Pro Leu Phe Gln Leu Met Ala Glu Arg Val Gly His
                 165                 170                 175

Phe Leu Trp Glu Asp Gln Thr Asp Glu Asp Ser Arg Leu Ser Glu Leu
             180                 185                 190

Asp Glu Asp Glu His Asn Asp Arg Asp Ser Arg Leu Phe Gln Leu Thr
         195                 200                 205

His Leu Leu Leu Lys Ile Val Pro Thr Glu Leu Glu Val Met His Ile
     210                 215                 220

Cys Tyr Thr Asn Leu Lys Ala Ser Thr Ser Ala Glu Val Gly Arg Phe
225                 230                 235                 240

Ile Lys Lys Leu Leu Glu Thr Ser Pro Asp Ile Leu Arg Glu Tyr Ile
                 245                 250                 255

Ile Gln Leu Gln Glu His Met Leu Thr Val Ile Pro Pro Ser Thr Leu
             260                 265                 270

Gly Ala Arg Asn Ile His Val Met Met Glu Phe Leu Leu Leu Ile Leu
         275                 280                 285

Ser Asp Met Pro Lys Asp Phe Ile His His Asp Lys Leu Phe Asp Leu
     290                 295                 300

Leu Ala His Val Gly Thr Leu Thr Arg Glu Val Ser Thr Leu Val Arg
305                 310                 315                 320

Asp Leu Glu Glu Lys Leu Arg Asn Lys Glu Gly Asn Asn Gln Thr Asn
                 325                 330                 335

Cys Ala Thr Leu Asp Leu Leu Glu Asn Ile Glu Leu Leu Lys Lys Asp
             340                 345                 350

Leu Lys His Val Tyr Leu Lys Ala Pro Asn Ser Ser Gln Cys Cys Phe
         355                 360                 365

Pro Met Ser Asp Gly Pro Leu Phe Met His Leu Leu His Met His Leu
     370                 375                 380

Asn Asp Leu Leu Asp Ser Asn Ala Tyr Ser Ile Ser Leu Ile Lys Glu
385                 390                 395                 400

Glu Ile Glu Leu Val Ser Gln Glu Leu Glu Phe Ile Arg Ser Phe Phe
                 405                 410                 415

Gly Asp Ala Ala Glu Gln Gly Leu Tyr Lys Asp Ile Trp Ala Arg Val
             420                 425                 430

Leu Asp Val Ala Tyr Glu Ala Lys Asp Val Ile Asp Ser Ile Ile Val
         435                 440                 445

Arg Asp Asn Gly Leu Leu His Leu Ile Phe Ser Leu Pro Ile Thr Ile
     450                 455                 460

Lys Lys Ile Lys Leu Ile Lys Glu Glu Ile Ser Ala Leu Asp Glu Asn
```

-continued

```
465                 470                 475                 480
Ile Pro Lys Asp Arg Gly Leu Ile Val Val Asn Ser Pro Lys Lys Pro
                    485                 490                 495
Val Glu Arg Lys Ser Leu Thr Thr Asp Lys Ile Ile Val Gly Phe Glu
                500                 505                 510
Glu Glu Thr Asn Leu Ile Leu Arg Lys Leu Thr Ser Gly Pro Ala Asp
            515                 520                 525
Leu Asp Val Ile Ser Ile Thr Gly Met Pro Gly Ser Gly Lys Thr Thr
    530                 535                 540
Leu Ala Tyr Lys Val Tyr Asn Asp Lys Ser Val Ser Arg His Phe Asp
545                 550                 555                 560
Leu Arg Ala Trp Cys Thr Val Asp Gln Gly Tyr Asp Asp Lys Lys Leu
                565                 570                 575
Leu Asp Thr Ile Phe Ser Gln Val Ser Gly Ser Asp Ser Asn Leu Ser
                580                 585                 590
Glu Asn Ile Asp Val Ala Asp Lys Leu Arg Lys Gln Leu Phe Gly Lys
            595                 600                 605
Arg Tyr Leu Ile Val Leu Asp Asp Val Trp Asp Thr Thr Thr Leu Asp
    610                 615                 620
Glu Leu Thr Arg Pro Phe Pro Glu Ala Lys Lys Gly Ser Arg Ile Ile
625                 630                 635                 640
Leu Thr Thr Arg Glu Lys Glu Val Ala Leu His Gly Lys Leu Asn Thr
                645                 650                 655
Asp Pro Leu Asp Leu Arg Leu Leu Arg Pro Asp Glu Ser Trp Glu Leu
                660                 665                 670
Leu Glu Lys Arg Thr Phe Gly Asn Glu Ser Cys Pro Asp Glu Leu Leu
            675                 680                 685
Asp Val Gly Lys Glu Ile Ala Glu Asn Cys Lys Gly Leu Pro Leu Val
    690                 695                 700
Ala Asp Leu Ile Ala Gly Val Ile Ala Gly Arg Glu Lys Lys Arg Ser
705                 710                 715                 720
Val Trp Leu Glu Val Gln Ser Ser Leu Ser Ser Phe Ile Leu Asn Ser
                725                 730                 735
Glu Val Glu Val Met Lys Val Ile Glu Leu Ser Tyr Asp His Leu Pro
                740                 745                 750
His His Leu Lys Pro Cys Leu Leu His Phe Ala Ser Trp Pro Lys Asp
            755                 760                 765
Thr Pro Leu Thr Ile Tyr Leu Leu Thr Val Tyr Leu Gly Ala Glu Gly
    770                 775                 780
Phe Val Glu Lys Thr Glu Met Lys Gly Ile Glu Glu Val Lys Ile
785                 790                 795                 800
Tyr Met Asp Asp Leu Ile Ser Ser Ser Leu Val Ile Cys Phe Asn Glu
                805                 810                 815
Ile Gly Asp Ile Leu Asn Phe Gln Ile His Asp Leu Val His Asp Phe
            820                 825                 830
Cys Leu Ile Lys Ala Arg Lys Glu Asn Leu Phe Asp Arg Ile Arg Ser
        835                 840                 845
Ser Ala Pro Ser Asp Leu Leu Pro Arg Gln Ile Thr Ile Asp Tyr Asp
    850                 855                 860
Glu Glu Glu His Phe Gly Leu Asn Phe Val Met Phe Asp Ser Asn
865                 870                 875                 880
Lys Lys Arg His Ser Gly Lys His Leu Tyr Ser Leu Arg Ile Asn Gly
                885                 890                 895
```

Asp Gln Leu Asp Asp Ser Val Ser Asp Ala Phe His Leu Arg His Leu
                900                 905                 910

Arg Leu Ile Arg Val Leu Asp Leu Glu Pro Ser Leu Ile Met Val Asn
            915                 920                 925

Asp Ser Leu Leu Asn Glu Ile Cys Met Leu Asn His Leu Arg Tyr Leu
        930                 935                 940

Arg Ile Arg Thr Gln Val Lys Tyr Leu Pro Phe Ser Phe Ser Asn Leu
945                 950                 955                 960

Trp Asn Leu Glu Ser Leu Phe Val Ser Asn Lys Gly Ser Ile Leu Val
                965                 970                 975

Leu Leu Pro Arg Ile Leu Asp Leu Val Lys Leu Arg Val Leu Ser Val
            980                 985                 990

Gly Ala Cys Ser Phe Phe Asp Met Asp Ala Asp Glu Ser Ile Leu Ile
        995                 1000                1005

Ala Lys Asp Thr Lys Leu Glu Asn Leu Arg Ile Leu Gly Glu Leu Leu
    1010                1015                1020

Ile Ser Tyr Ser Lys Asp Thr Met Asn Ile Phe Lys Arg Phe Pro Asn
1025                1030                1035                1040

Leu Gln Val Leu Gln Phe Glu Leu Lys Glu Ser Trp Asp Tyr Ser Thr
                1045                1050                1055

Glu Gln His Trp Phe Pro Lys Leu Asp Cys Leu Thr Glu Leu Glu Thr
            1060                1065                1070

Leu Cys Val Gly Phe Lys Ser Ser Asn Thr Asn His Cys Gly Ser Ser
        1075                1080                1085

Val Ala Thr Asn Arg Pro Trp Asp Phe His Phe Pro Ser Asn Leu Lys
    1090                1095                1100

Glu Leu Leu Tyr Asp Phe Pro Leu Thr Ser Asp Ser Leu Ser Thr
1105                1110                1115                1120

Ile Ala Arg Leu Pro Asn Leu Glu Asn Leu Ser Leu Tyr Asp Thr Ile
                1125                1130                1135

Ile Gln Gly Glu Glu Trp Asn Met Gly Glu Glu Asp Thr Phe Glu Asn
            1140                1145                1150

Leu Lys Phe Leu Asn Leu Arg Leu Leu Thr Leu Ser Lys Trp Glu Val
        1155                1160                1165

Gly Glu Glu Ser Phe Pro Asn Leu Glu Lys Leu Lys Leu Gln Glu Cys
    1170                1175                1180

Gly Lys Leu Glu Glu Ile Pro Pro Ser Phe Gly Asp Ile Tyr Ser Leu
1185                1190                1195                1200

Lys Phe Ile Lys Ile Val Lys Ser Pro Gln Leu Glu Asp Ser Ala Leu
                1205                1210                1215

Lys Ile Lys Lys Tyr Ala Glu Asp Met Arg Gly Gly Asn Glu Leu Gln
            1220                1225                1230

Ile Leu Gly Gln Lys Asn Ile Pro Leu Phe Lys
        1235                1240

<210> SEQ ID NO 18
<211> LENGTH: 1257
<212> TYPE: PRT
<213> ORGANISM: Artificial Sequence
<220> FEATURE:
<223> OTHER INFORMATION: Description of Artificial Sequence: ORF1
      encoded polypeptide

<400> SEQUENCE: 18

Met Glu Lys Arg Lys Asp Ile Glu Glu Ala Asn Asn Ser Leu Val Leu

-continued

```
  1                   5                      10                       15

Phe Ser Ala Leu Ser Lys Asp Ile Ala Asn Val Leu Ile Phe Leu Glu
            20                  25                  30

Asn Glu Asn Gln Lys Ala Leu Asp Lys Asp Gln Val Glu Lys Leu
        35                  40                  45

Lys Leu Lys Met Ala Phe Ile Cys Thr Tyr Val Gln Leu Ser Tyr Ser
    50                  55                  60

Asp Phe Glu Gln Phe Glu Asp Ile Met Thr Arg Asn Arg Gln Glu Val
65                  70                  75                      80

Glu Asn Leu Leu Gln Ser Leu Leu Asp Asp Val Leu Thr Ser Leu
                85                  90                  95

Thr Ser Asn Met Asp Asp Cys Ile Ser Leu Tyr His Arg Ser Tyr Lys
            100                 105                 110

Ser Asp Ala Ile Met Met Asp Glu Gln Leu Asp Phe Leu Leu Leu Asn
        115                 120                 125

Leu Tyr His Leu Ser Lys His His Ala Glu Lys Ile Phe Pro Gly Val
    130                 135                 140

Thr Gln Tyr Glu Val Leu Gln Asn Val Cys Gly Asn Ile Arg Asp Phe
145                 150                 155                 160

His Gly Leu Ile Leu Asn Gly Cys Ile Lys His Glu Met Val Glu Asn
                165                 170                 175

Val Leu Pro Leu Phe Gln Leu Met Ala Glu Arg Val Gly His Phe Leu
            180                 185                 190

Trp Glu Asp Gln Thr Asp Glu Asp Ser Arg Leu Ser Glu Leu Asp Glu
        195                 200                 205

Asp Glu His Asn Asp Arg Asp Ser Arg Leu Phe Gln Leu Thr His Leu
    210                 215                 220

Leu Leu Lys Ile Val Pro Thr Glu Leu Glu Val Met His Ile Cys Tyr
225                 230                 235                 240

Thr Asn Leu Lys Ala Ser Thr Ser Ala Glu Val Gly Arg Phe Ile Lys
                245                 250                 255

Lys Leu Leu Glu Thr Ser Pro Asp Ile Leu Arg Glu Tyr Ile Ile Gln
            260                 265                 270

Leu Gln Glu His Met Leu Thr Val Ile Pro Pro Ser Thr Leu Gly Ala
        275                 280                 285

Arg Asn Ile His Val Met Met Glu Phe Leu Leu Ile Leu Ser Asp
    290                 295                 300

Met Pro Lys Asp Phe Ile His His Asp Lys Leu Phe Asp Leu Leu Ala
305                 310                 315                 320

His Val Gly Thr Leu Thr Arg Glu Val Ser Thr Leu Val Arg Asp Leu
                325                 330                 335

Glu Glu Lys Leu Arg Asn Lys Glu Gly Asn Asn Gln Thr Asn Cys Ala
            340                 345                 350

Thr Leu Asp Leu Leu Glu Asn Ile Glu Leu Leu Lys Lys Asp Leu Lys
        355                 360                 365

His Val Tyr Leu Lys Ala Pro Asn Ser Ser Gln Cys Cys Phe Pro Met
    370                 375                 380

Ser Asp Gly Pro Leu Phe Met His Leu Leu His Met His Leu Asn Asp
385                 390                 395                 400

Leu Leu Asp Ser Asn Ala Tyr Ser Ile Ser Leu Ile Lys Glu Glu Ile
                405                 410                 415

Glu Leu Val Ser Gln Glu Leu Glu Phe Ile Arg Ser Phe Phe Gly Asp
            420                 425                 430
```

-continued

```
Ala Ala Glu Gln Gly Leu Tyr Lys Asp Ile Trp Ala Arg Val Leu Asp
            435                 440                 445
Val Ala Tyr Glu Ala Lys Asp Val Ile Asp Ser Ile Ile Val Arg Asp
        450                 455                 460
Asn Gly Leu Leu His Leu Ile Phe Ser Leu Pro Ile Thr Ile Lys Lys
465                 470                 475                 480
Ile Lys Leu Ile Lys Glu Glu Ile Ser Ala Leu Asp Glu Asn Ile Pro
                485                 490                 495
Lys Asp Arg Gly Leu Ile Val Val Asn Ser Pro Lys Lys Pro Val Glu
            500                 505                 510
Arg Lys Ser Leu Thr Thr Asp Lys Ile Ile Val Gly Phe Glu Glu Glu
        515                 520                 525
Thr Asn Leu Ile Leu Arg Lys Leu Thr Ser Gly Pro Ala Asp Leu Asp
        530                 535                 540
Val Ile Ser Ile Thr Gly Met Pro Gly Ser Gly Lys Thr Thr Leu Ala
545                 550                 555                 560
Tyr Lys Val Tyr Asn Asp Lys Ser Val Ser Arg His Phe Asp Leu Arg
                565                 570                 575
Ala Trp Cys Thr Val Asp Gln Gly Tyr Asp Asp Lys Lys Leu Leu Asp
            580                 585                 590
Thr Ile Phe Ser Gln Val Ser Gly Ser Asp Ser Asn Leu Ser Glu Asn
        595                 600                 605
Ile Asp Val Ala Asp Lys Leu Arg Lys Gln Leu Phe Gly Lys Arg Tyr
        610                 615                 620
Leu Ile Val Leu Asp Asp Val Trp Asp Thr Thr Thr Leu Asp Glu Leu
625                 630                 635                 640
Thr Arg Pro Phe Pro Glu Ala Lys Lys Gly Ser Arg Ile Ile Leu Thr
                645                 650                 655
Thr Arg Glu Lys Glu Val Ala Leu His Gly Lys Leu Asn Thr Asp Pro
            660                 665                 670
Leu Asp Leu Arg Leu Leu Arg Pro Asp Glu Ser Trp Glu Leu Leu Glu
        675                 680                 685
Lys Arg Thr Phe Gly Asn Glu Ser Cys Pro Asp Glu Leu Leu Asp Val
        690                 695                 700
Gly Lys Glu Ile Ala Glu Asn Cys Lys Gly Leu Pro Leu Val Ala Asp
705                 710                 715                 720
Leu Ile Ala Gly Val Ile Ala Gly Arg Glu Lys Lys Arg Ser Val Trp
                725                 730                 735
Leu Glu Val Gln Ser Ser Leu Ser Ser Phe Ile Leu Asn Ser Glu Val
            740                 745                 750
Glu Val Met Lys Val Ile Glu Leu Ser Tyr Asp His Leu Pro His His
        755                 760                 765
Leu Lys Pro Cys Leu Leu His Phe Ala Ser Trp Pro Lys Asp Thr Pro
        770                 775                 780
Leu Thr Ile Tyr Leu Leu Thr Val Tyr Leu Gly Ala Glu Gly Phe Val
785                 790                 795                 800
Glu Lys Thr Glu Met Lys Gly Ile Glu Val Val Lys Ile Tyr Met
                805                 810                 815
Asp Asp Leu Ile Ser Ser Ser Leu Val Ile Cys Phe Asn Glu Ile Gly
            820                 825                 830
Asp Ile Leu Asn Phe Gln Ile His Asp Leu Val His Asp Phe Cys Leu
        835                 840                 845
```

-continued

```
Ile Lys Ala Arg Lys Glu Asn Leu Phe Asp Arg Ile Arg Ser Ser Ala
    850                 855                 860

Pro Ser Asp Leu Leu Pro Arg Gln Ile Thr Ile Asp Tyr Asp Glu Glu
865                 870                 875                 880

Glu Glu His Phe Gly Leu Asn Phe Val Met Phe Asp Ser Asn Lys Lys
                885                 890                 895

Arg His Ser Gly Lys His Leu Tyr Ser Leu Arg Ile Asn Gly Asp Gln
            900                 905                 910

Leu Asp Asp Ser Val Ser Asp Ala Phe His Leu Arg His Leu Arg Leu
        915                 920                 925

Ile Arg Val Leu Asp Leu Glu Pro Ser Leu Ile Met Val Asn Asp Ser
    930                 935                 940

Leu Leu Asn Glu Ile Cys Met Leu Asn His Leu Arg Tyr Leu Arg Ile
945                 950                 955                 960

Arg Thr Gln Val Lys Tyr Leu Pro Phe Ser Phe Ser Asn Leu Trp Asn
                965                 970                 975

Leu Glu Ser Leu Phe Val Ser Asn Lys Gly Ser Ile Leu Val Leu Leu
            980                 985                 990

Pro Arg Ile Leu Asp Leu Val Lys Leu Arg Val Leu Ser Val Gly Ala
        995                 1000                1005

Cys Ser Phe Phe Asp Met Asp Ala Asp Glu Ser Ile Leu Ile Ala Lys
    1010                1015                1020

Asp Thr Lys Leu Glu Asn Leu Arg Ile Leu Gly Glu Leu Leu Ile Ser
1025                1030                1035                1040

Tyr Ser Lys Asp Thr Met Asn Ile Phe Lys Arg Phe Pro Asn Leu Gln
                1045                1050                1055

Val Leu Gln Phe Glu Leu Lys Glu Ser Trp Asp Tyr Ser Thr Glu Gln
            1060                1065                1070

His Trp Phe Pro Lys Leu Asp Cys Leu Thr Glu Leu Glu Thr Leu Cys
        1075                1080                1085

Val Gly Phe Lys Ser Ser Asn Thr Asn His Cys Gly Ser Ser Val Ala
    1090                1095                1100

Thr Asn Arg Pro Trp Asp Phe His Phe Pro Ser Asn Leu Lys Glu Leu
1105                1110                1115                1120

Leu Leu Tyr Asp Phe Pro Leu Thr Ser Asp Ser Leu Ser Thr Ile Ala
                1125                1130                1135

Arg Leu Pro Asn Leu Glu Asn Leu Ser Leu Tyr Asp Thr Ile Ile Gln
            1140                1145                1150

Gly Glu Glu Trp Asn Met Gly Glu Glu Asp Thr Phe Glu Asn Leu Lys
        1155                1160                1165

Phe Leu Asn Leu Arg Leu Leu Thr Leu Ser Lys Trp Glu Val Gly Glu
    1170                1175                1180

Glu Ser Phe Pro Asn Leu Glu Lys Leu Lys Leu Gln Glu Cys Gly Lys
1185                1190                1195                1200

Leu Glu Glu Ile Pro Pro Ser Phe Gly Asp Ile Tyr Ser Leu Lys Phe
                1205                1210                1215

Ile Lys Ile Val Lys Ser Pro Gln Leu Glu Asp Ser Ala Leu Lys Ile
            1220                1225                1230

Lys Lys Tyr Ala Glu Asp Met Arg Gly Gly Asn Glu Leu Gln Ile Leu
        1235                1240                1245

Gly Gln Lys Asn Ile Pro Leu Phe Lys
    1250                1255
```

```
<210> SEQ ID NO 19
<211> LENGTH: 1206
<212> TYPE: PRT
<213> ORGANISM: Artificial Sequence
<220> FEATURE:
<223> OTHER INFORMATION: Description of Artificial Sequence: ORF2
      encoded polypeptide

<400> SEQUENCE: 19
```

| Met | Ala | Phe | Ile | Cys | Thr | Tyr | Val | Gln | Leu | Ser | Tyr | Ser | Asp | Phe | Glu |
|---|---|---|---|---|---|---|---|---|---|---|---|---|---|---|---|
| 1 | | | | 5 | | | | | 10 | | | | | 15 | |

| Gln | Phe | Glu | Asp | Ile | Met | Thr | Arg | Asn | Arg | Gln | Glu | Val | Glu | Asn | Leu |
| | | | 20 | | | | | 25 | | | | | 30 | | |

| Leu | Gln | Ser | Leu | Leu | Asp | Asp | Val | Leu | Thr | Ser | Leu | Thr | Ser | Asn |
| | 35 | | | | | 40 | | | | | 45 | | | |

| Met | Asp | Asp | Cys | Ile | Ser | Leu | Tyr | His | Arg | Ser | Tyr | Lys | Ser | Asp | Ala |
| | 50 | | | | | 55 | | | | | 60 | | | | |

| Ile | Met | Met | Asp | Glu | Gln | Leu | Asp | Phe | Leu | Leu | Asn | Leu | Tyr | His |
| 65 | | | | | 70 | | | | 75 | | | | | 80 |

| Leu | Ser | Lys | His | His | Ala | Glu | Lys | Ile | Phe | Pro | Gly | Val | Thr | Gln | Tyr |
| | | | | 85 | | | | | 90 | | | | | 95 | |

| Glu | Val | Leu | Gln | Asn | Val | Cys | Gly | Asn | Ile | Arg | Asp | Phe | His | Gly | Leu |
| | | | | 100 | | | | 105 | | | | | 110 | | |

| Ile | Leu | Asn | Gly | Cys | Ile | Lys | His | Glu | Met | Val | Glu | Asn | Val | Leu | Pro |
| | | | 115 | | | | | 120 | | | | | 125 | | |

| Leu | Phe | Gln | Leu | Met | Ala | Glu | Arg | Val | Gly | His | Phe | Leu | Trp | Glu | Asp |
| | 130 | | | | | 135 | | | | | 140 | | | | |

| Gln | Thr | Asp | Glu | Asp | Ser | Arg | Leu | Ser | Glu | Leu | Asp | Glu | Asp | Glu | His |
| 145 | | | | | 150 | | | | 155 | | | | | 160 | |

| Asn | Asp | Arg | Asp | Ser | Arg | Leu | Phe | Gln | Leu | Thr | His | Leu | Leu | Leu | Lys |
| | | | | 165 | | | | | 170 | | | | | 175 | |

| Ile | Val | Pro | Thr | Glu | Leu | Glu | Val | Met | His | Ile | Cys | Tyr | Thr | Asn | Leu |
| | | | 180 | | | | | 185 | | | | | 190 | | |

| Lys | Ala | Ser | Thr | Ser | Ala | Glu | Val | Gly | Arg | Phe | Ile | Lys | Lys | Leu | Leu |
| | | | 195 | | | | | 200 | | | | | 205 | | |

| Glu | Thr | Ser | Pro | Asp | Ile | Leu | Arg | Glu | Tyr | Ile | Ile | Gln | Leu | Gln | Glu |
| | 210 | | | | | 215 | | | | | 220 | | | | |

| His | Met | Leu | Thr | Val | Ile | Pro | Pro | Ser | Thr | Leu | Gly | Ala | Arg | Asn | Ile |
| 225 | | | | | 230 | | | | 235 | | | | | 240 | |

| His | Val | Met | Met | Glu | Phe | Leu | Leu | Leu | Ile | Leu | Ser | Asp | Met | Pro | Lys |
| | | | | 245 | | | | | 250 | | | | | 255 | |

| Asp | Phe | Ile | His | His | Asp | Lys | Leu | Phe | Asp | Leu | Leu | Ala | His | Val | Gly |
| | | | 260 | | | | | 265 | | | | | 270 | | |

| Thr | Leu | Thr | Arg | Glu | Val | Ser | Thr | Leu | Val | Arg | Asp | Leu | Glu | Glu | Lys |
| | | | 275 | | | | | 280 | | | | | 285 | | |

| Leu | Arg | Asn | Lys | Glu | Gly | Asn | Asn | Gln | Thr | Asn | Cys | Ala | Thr | Leu | Asp |
| | 290 | | | | | 295 | | | | | 300 | | | | |

| Leu | Leu | Glu | Asn | Ile | Glu | Leu | Lys | Lys | Asp | Leu | Lys | His | Val | Tyr |
| 305 | | | | | 310 | | | | 315 | | | | | 320 |

| Leu | Lys | Ala | Pro | Asn | Ser | Ser | Gln | Cys | Cys | Phe | Pro | Met | Ser | Asp | Gly |
| | | | | 325 | | | | | 330 | | | | | 335 | |

| Pro | Leu | Phe | Met | His | Leu | Leu | His | Met | His | Leu | Asn | Asp | Leu | Leu | Asp |
| | | | 340 | | | | | 345 | | | | | 350 | | |

| Ser | Asn | Ala | Tyr | Ser | Ile | Ser | Leu | Ile | Lys | Glu | Glu | Ile | Glu | Leu | Val |
| | | | 355 | | | | | 360 | | | | | 365 | | |

```
Ser Gln Glu Leu Glu Phe Ile Arg Ser Phe Gly Asp Ala Ala Glu
    370                 375                 380

Gln Gly Leu Tyr Lys Asp Ile Trp Ala Arg Val Leu Asp Val Ala Tyr
385                 390                 395                 400

Glu Ala Lys Asp Val Ile Asp Ser Ile Ile Val Arg Asp Asn Gly Leu
                405                 410                 415

Leu His Leu Ile Phe Ser Leu Pro Ile Thr Ile Lys Lys Ile Lys Leu
            420                 425                 430

Ile Lys Glu Glu Ile Ser Ala Leu Asp Glu Asn Ile Pro Lys Asp Arg
        435                 440                 445

Gly Leu Ile Val Val Asn Ser Pro Lys Pro Val Glu Arg Lys Ser
    450                 455                 460

Leu Thr Thr Asp Lys Ile Ile Val Gly Phe Glu Glu Thr Asn Leu
465                 470                 475                 480

Ile Leu Arg Lys Leu Thr Ser Gly Pro Ala Asp Leu Asp Val Ile Ser
                485                 490                 495

Ile Thr Gly Met Pro Gly Ser Gly Lys Thr Thr Leu Ala Tyr Lys Val
            500                 505                 510

Tyr Asn Asp Lys Ser Val Ser Arg His Phe Asp Leu Arg Ala Trp Cys
            515                 520                 525

Thr Val Asp Gln Gly Tyr Asp Asp Lys Lys Leu Leu Asp Thr Ile Phe
    530                 535                 540

Ser Gln Val Ser Gly Ser Asp Ser Asn Leu Ser Glu Asn Ile Asp Val
545                 550                 555                 560

Ala Asp Lys Leu Arg Lys Gln Leu Phe Gly Lys Arg Tyr Leu Ile Val
                565                 570                 575

Leu Asp Asp Val Trp Asp Thr Thr Leu Asp Glu Leu Thr Arg Pro
            580                 585                 590

Phe Pro Glu Ala Lys Lys Gly Ser Arg Ile Ile Leu Thr Thr Arg Glu
        595                 600                 605

Lys Glu Val Ala Leu His Gly Lys Leu Asn Thr Asp Pro Leu Asp Leu
    610                 615                 620

Arg Leu Leu Arg Pro Asp Glu Ser Trp Glu Leu Leu Glu Lys Arg Thr
625                 630                 635                 640

Phe Gly Asn Glu Ser Cys Pro Asp Glu Leu Leu Asp Val Gly Lys Glu
                645                 650                 655

Ile Ala Glu Asn Cys Lys Gly Leu Pro Leu Val Ala Asp Leu Ile Ala
            660                 665                 670

Gly Val Ile Ala Gly Arg Glu Lys Lys Arg Ser Val Trp Leu Glu Val
        675                 680                 685

Gln Ser Ser Leu Ser Ser Phe Ile Leu Asn Ser Glu Val Glu Val Met
    690                 695                 700

Lys Val Ile Glu Leu Ser Tyr Asp His Leu Pro His His Leu Lys Pro
705                 710                 715                 720

Cys Leu Leu His Phe Ala Ser Trp Pro Lys Asp Thr Pro Leu Thr Ile
                725                 730                 735

Tyr Leu Leu Thr Val Tyr Leu Gly Ala Glu Gly Phe Val Glu Lys Thr
            740                 745                 750

Glu Met Lys Gly Ile Glu Val Val Lys Ile Tyr Met Asp Asp Leu
        755                 760                 765

Ile Ser Ser Ser Leu Val Ile Cys Phe Asn Glu Ile Gly Asp Ile Leu
    770                 775                 780

Asn Phe Gln Ile His Asp Leu Val His Asp Phe Cys Leu Ile Lys Ala
```

-continued

```
                785               790               795               800
Arg Lys Glu Asn Leu Phe Asp Arg Ile Arg Ser Ser Ala Pro Ser Asp
                805               810               815
Leu Leu Pro Arg Gln Ile Thr Ile Asp Tyr Asp Glu Glu Glu His
                820               825               830
Phe Gly Leu Asn Phe Val Met Phe Asp Ser Asn Lys Lys Arg His Ser
                835               840               845
Gly Lys His Leu Tyr Ser Leu Arg Ile Asn Gly Asp Gln Leu Asp Asp
                850               855               860
Ser Val Ser Asp Ala Phe His Leu Arg His Leu Arg Leu Ile Arg Val
865               870               875               880
Leu Asp Leu Glu Pro Ser Leu Ile Met Val Asn Asp Ser Leu Leu Asn
                885               890               895
Glu Ile Cys Met Leu Asn His Leu Arg Tyr Leu Arg Ile Arg Thr Gln
                900               905               910
Val Lys Tyr Leu Pro Phe Ser Phe Ser Asn Leu Trp Asn Leu Glu Ser
                915               920               925
Leu Phe Val Ser Asn Lys Gly Ser Ile Leu Val Leu Pro Arg Ile
                930               935               940
Leu Asp Leu Val Lys Leu Arg Val Leu Ser Val Gly Ala Cys Ser Phe
945               950               955               960
Phe Asp Met Asp Ala Asp Glu Ser Ile Leu Ile Ala Lys Asp Thr Lys
                965               970               975
Leu Glu Asn Leu Arg Ile Leu Gly Glu Leu Ile Ser Tyr Ser Lys
                980               985               990
Asp Thr Met Asn Ile Phe Lys Arg Phe Pro Asn Leu Gln Val Leu Gln
                995               1000              1005
Phe Glu Leu Lys Glu Ser Trp Asp Tyr Ser Thr Glu Gln His Trp Phe
                1010              1015              1020
Pro Lys Leu Asp Cys Leu Thr Glu Leu Glu Thr Leu Cys Val Gly Phe
1025              1030              1035              1040
Lys Ser Ser Asn Thr Asn His Cys Gly Ser Ser Val Ala Thr Asn Arg
                1045              1050              1055
Pro Trp Asp Phe His Phe Pro Ser Asn Leu Lys Glu Leu Leu Leu Tyr
                1060              1065              1070
Asp Phe Pro Leu Thr Ser Asp Ser Leu Ser Thr Ile Ala Arg Leu Pro
                1075              1080              1085
Asn Leu Glu Asn Leu Ser Leu Tyr Asp Thr Ile Ile Gln Gly Glu Glu
                1090              1095              1100
Trp Asn Met Gly Glu Glu Asp Thr Phe Glu Asn Leu Lys Phe Leu Asn
1105              1110              1115              1120
Leu Arg Leu Leu Thr Leu Ser Lys Trp Glu Val Gly Glu Glu Ser Phe
                1125              1130              1135
Pro Asn Leu Glu Lys Leu Lys Leu Gln Glu Cys Gly Lys Leu Glu Glu
                1140              1145              1150
Ile Pro Pro Ser Phe Gly Asp Ile Tyr Ser Leu Lys Phe Ile Lys Ile
                1155              1160              1165
Val Lys Ser Pro Gln Leu Glu Asp Ser Ala Leu Lys Ile Lys Lys Tyr
                1170              1175              1180
```

```
Ala Glu Asp Met Arg Gly Gly Asn Glu Leu Gln Ile Leu Gly Gln Lys
1185                1190                1195                1200

Asn Ile Pro Leu Phe Lys
                1205
```

TOMATO NUCLEIC ACID ENCODING PROTEIN THAT CONFERS RESISTANCE TO APHIDS AND NEMATODES AND PLANTS TRANSFORMED THEREWITH

This application is a continuation of application No. PCT/EP97/04340 filed Aug. 8, 1997.

FIELD OF THE INVENTION

The present invention relates to resistance genes, DNA constructs, micro organisms, plant cells and plants comprising said resistance genes. Furthermore the invention relates to genetically transformed plants which are resistant against nematodes and/or aphids. In addition, the invention relates to probes, and primers for the identification of the resistance genes and diagnostic kits comprising said probes and/or primers. Finally, the invention relates to polypeptides encoded by said resistance genes and the use of said polypeptides.

BACKGROUND OF THE INVENTION

Plant pathogens are responsible for substantially losses of plants and plant products due to infection of the plant. Plant diseases, as a result of infection by plant pathogens or pests, cause damage to the plants and/or plant products, reduce production and yield, limit the Kind of plants that can grow in certain geographic areas and as a result cause severe (financial) losses to the grower.

Plant parasitic nematodes occur worldwide and most of them live most of their life in the topsoil layer. Although losses caused by direct feeding of nematodes on plant roots is considered to be of minor importance, several species, among them the root-knot nematodes belonging to the Meloidogyne species, the cyst nematodes belonging to the Heterodera species and Globodera species and other nematodes such as the Nacobbus species, cause severe damage and economic crop losses. Root-knot nematodes also occur throughout the world but are found more frequently and in greater numbers in areas with warmer climates and in greenhouses. The most important Meloidogyne species are *M. incognita, M. arenaria, M. hapla* and *M. javanica*, of which *M. hapla* also occurs in more temperate climatic zones.

Different means for control of the plant pathogens exist, such as mechanical cultivation of the soil, chemical treatment with pesticides, including nematicides and insecticides, or crop rotation. However, for certain plant pathogens, especially nematodes, these means of control are insufficient to protect the plants from infection and resulting diseases. The only effective means of control involves plant host resistance (Russell, 1978, Plant Breeding for pest and disease resistance, Butterworths edit., 485 pp). The development of cultivars resistant to common plant pathogens is one of the major goals of plant breeders today, in order to reduce or ultimately eliminate the extensive need for pesticides. The burden for the environment of the large amounts of pesticides injected into the soil or sprayed on crops, trees etc. worldwide each year becomes too severe. Moreover, governmental regulations in Western countries restrict the use or even forbid the use of certain pesticides. Therefore, the need for plants which are resistant to one or more of their pathogens, or which have a reduced susceptibility to their attackers becomes more and more pressing. The development of resistant plants is one of the important objectives of current plant breeding programs. Plant genotypes susceptible for particular pathogens are crossed with resistant plant genotypes in order to introduce the resistant phenotype into the breeding line.

Damage by root-knot nematodes results primarily from the invasion of the plant roots by larvae which in a compatible relationship with the plant develop into a reproducing female. After invasion the larvae cause root cells to develop into giant cells on which they feed. Upon infection galls or knots are formed on the roots and the plant roots become otherwise disturbed, thickened and stunted. The root system thus disfunctions in the uptake of water and nutritional elements which damages the plant growth and development. Frequently damage to infected plants is increased by parasitic fungi attacking the weakened root tissue. Infected plants show reduced growth and smaller pale coloured leaves, with dwarf poor quality fruits or even without fruits, and tend to wilt in warmer climates (Agrios, 1988 in: Plant Pathology, Academic Press, Inc.). The damage and/or yield reduction caused by root-knot nematodes is substantial on the total agricultural production worldwide. In individual stand yield losses can be as high as 25–50%, or even a crop may be killed.

In greenhouses root-not nematodes can be controlled with steam sterilization of the soil or soil fumigation with nematicides. Under field conditions control can be achieved by the use of nematicides. However, the use of such, in some cases very persistent, chemicals is increasingly debated and in some countries the use of certain nematicides is even forbidden.

Breeding genetically resistant genotypes is the most reliable and effective way of controlling root-knot disease. For a number of crop species the availability of resistance within the related germplasm has been reported, e.g. potato, cotton, tobacco, wheat, soybean, tomato, eggplant, common bean and alfalfa. Resistance breeding is hampered by firstly the limited occurrence of (known) resistance genes in the available germplasm, secondly, in some plant species the existence of crossing barriers between the cultivated crop species and the resistance bearing related species, and thirdly, screening tests for resistance versus susceptibility to nematodes are laborious and often not reliable. Therefore, resistance breeding is very difficult or not to achieve, or if possible time consuming.

Successful introduction of resistance genes has been realized in tomato. The resistance gene *Mi* (*Meloidogyne incognita*) has been introduced into cultivated tomato, *Lycopersicon esculentum*, after crossing with the related wild species *L. peruvianum* (PI 128657), using embryo culture. The *Mi* gene confers resistance to various Meloidogyne spp. (Fassuliotis, 1991, in: Genetic Improvement of Tomato, Springer Verlag edit.). The *Mi* resistance gene is reported to be a monogenic dominant gene (Gilbert and McGuire, 1956, Proc. Am. Soc. Hortic. Sci. 68, 437–442) and is located on tomato chromosome 6. It is also postulated that the introgressed region comprising the *Mi* locus is involved in conferring resistance to potato aphid (*Macrosiphum euphorbia*) (Kaloshian et al, 1995, Proc. Natl. Acad. Sci. USA, 92, 622–625).

Plants have developed a complex defense mechanism against attack and infection by pathogens. To date, the exact mechanism of their defense system is not yet elucidated.

Nematode resistance in tomato is expressed after penetration. After the juvenile larva enters the root and establishes itself at a feeding site, a hypersensitive reaction (HR) adjacent to the head of the nematode is triggered that results in local death of the host cells. The nematode is also adversely affected by this HR and dies (Fassuliotis, 1991, in:

Genetic Improvement of Tomato, Springer Verlag edit.). Wether or not there exists a gene-for-gene relationship sensu Flor (1956, Adv.Gen. 8, 29–54) as is frequently the case in other plant-pathogen relationships where resistance is based on HR-incompatibility is unknown.

The isolation of plant genes without knowing their gene products is very laborious and difficult, because of the enormous genome sizes of plant species: e.g. tomato has a genome size of 1000 Mb ($10^9$ base pairs of nuclear DNA), maize has a genome size of 3000 Mb and wheat has even more than $16 \times 10^9$ base pairs. Searching for a specific gene among these billions of base pairs is only feasible when (i) there are enough molecular markers tightly linked to the gene of interest and (ii) there is good genetic material available (Tanksley et al., 1995, Trends in Genetics, 11, p. 63–68).

Although, the isolation of a few resistance genes has been reported, none of these resistance genes are able to confer the host plant resistant to nematodes or to aphids. Examples of such isolated resistance genes are: RPS2 from Arabidopsis (resistance to *Pseudomonas syringae* expressing avrRpt2), N from tobacco (resistance to tobacco mosaic virus), Cf-9 from tomato (resistance to the leaf fungal pathogen *Cladosponrum fulvum* carrying avr9) and $L^6$ from flax (resistance to the corresponding leaf rust fungal race) (Dangl, 1995, Cell 80, 363–366).

The present invention provides the first isolated nematode resistance gene, and furthermore, provides the first isolated aphid resistance gene. Moreover, the present invention relates to a dual function resistance gene conferring reduced susceptibility to nematodes as well as aphids, and preferably to *Meloidogyne incognita* and *Macrosiphum euphorbiae* respectively.

SUMMARY OF THE INVENTION

The present invention relates to a nucleic acid comprising the *Mi* resistance gene which when present and expressed in a plant is capable of conferring to said plant resistance against nematodes and/or aphids. Furthermore, the invention relates to the *Mi* resistance gene of which the DNA sequence is disclosed herein. The invention also relates to a gene product encoded by the *Mi* resistance gene. In addition, the present invention relates to DNA constructs, cosmids, vectors, bacterial strains, yeast cells and plant cells comprising the *Mi* resistance gene. In another aspect, the present invention relates to a genetically transformed plant, which is resistant to a nematode, said nematode being capable of infecting the untransformed plant. Furthermore, the invention relates to resistance genes which are homologous to the *Mi* resistance gene, and which, when present in a plant, are able of conferring said plant resistance to infection by pathogens.

Moreover, the present invention relates to a nucleic acid comprising the *Meu-1* resistance gene which when present in a plant is capable of conferring to said plant reduced susceptibility to aphids. In particular the *Meu-1* resistance gene corresponds to the *Mi* resistance gene. Especially the *Meu-1* resistance gene has the same nucleotide sequence as the *Mi* resistance gene. Thus, the present invention also relates to genetically transformed plants, which are reduced susceptible, and preferably resistant to aphids, in particular to potato aphids.

Finally, the invention relates to oligonucleotides corresponding to the sequence of the said resistance gene or part thereof, and detection kits comprising said oligonucleotides.

DESCRIPTION OF THE FIGURES

FIG. 5 shows the nucleotide sequence of a DNA segment of approximately 9.9 kb around the AFLP marker PM 14, and a deduced amino acid sequence of the *Mi* resistance gene (SEQ ID NO: 15 and SEQ ID NOs: 16 and 17). The initiation codon (ATG position 3263–3265) is underlined and the termination codon (TAG position 7109–7111) is double underlined, showing an open reading frame (ORF 1) encoding a polypeptide of 1257 amino acids (FIG. 7A). The *Mi* resistance gene comprises two intron sequences (shown in italics): one intron of 1306 nucleotides from position 1936 to position 3241 and one intron of 75 nucleotides from position 3305 to position 3379.

A second initiation codon (ATG position 3491–3493) which is in frame with the first initiation codon, results into a second open reading frame (ORF2) encoding a truncated polypeptide of 1206 amino acids (FIG. 7B).

The position of the AFLP marker PM14 is from nucleotide position 6921 (5'-TGCAGGA-3') to nucleotide position 7034 (5'-AGATTA-3').

Figure 6:
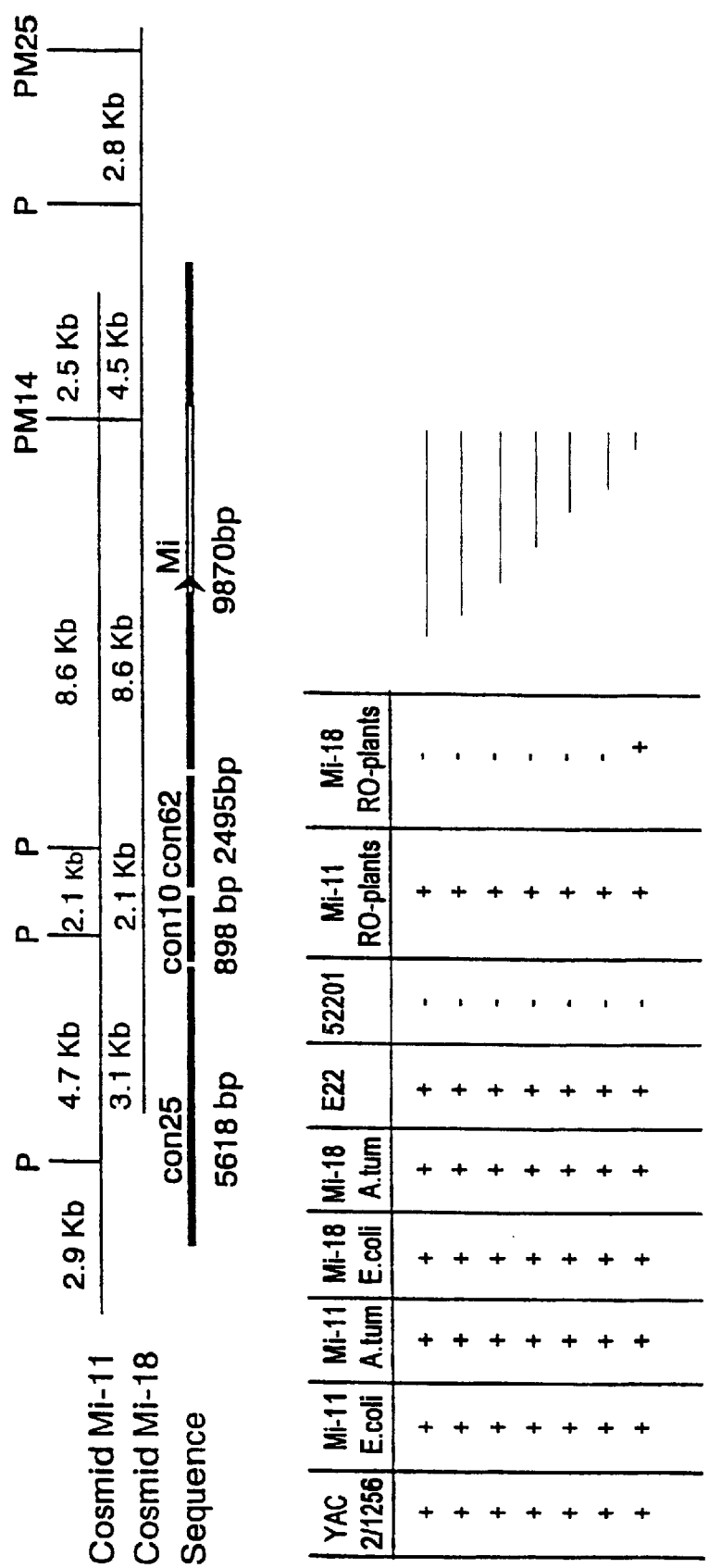

FIG. 6 shows a physical map of cosmids *Mi*-11 and *Mi*-18 and the determined nucleotide sequence of cosmid *Mi*-11. The sequence is divided in four contigs: con25 (5618 bp), con10 (898 kb), con62 (2495 bp) and *Mi* (9870 bp). The lower part of the figure depicts the presence ("+") or absence ("−") of several PCR fragments, corresponding to parts of the DNA segment of FIG. 5, which are represented as horizontal lines of different lengths at the right hand side of the table, in the various genetic backgrounds (YAC clone 2/1256, *E. coli* containing cosmid *Mi*-11, *A. tumefaciens* containing cosmid *Mi*-11, *E. coli* containing cosmid *Mi*-18, *A. tumefaciens* containing cosmid *Mi*-18, resistant tomato line E22, susceptible tomato line 52201, $R_0$ plants transformed with cosmid Mi-11 and R₀ plants transformed with cosmid Mi-18).

Nucleotide sequence of cosmid Mi-11 and cosmid Mi-18. Analysis of different contigs.

FIG. 7A: shows the deduced amino acid sequence of the polypeptide encoded by ORF1 (SEQ ID NO: 18).

B shows the educed amino acid sequence of the truncated polypeptide encoded by ORF2 (SEQ ID NO: 19).

Figure 8:
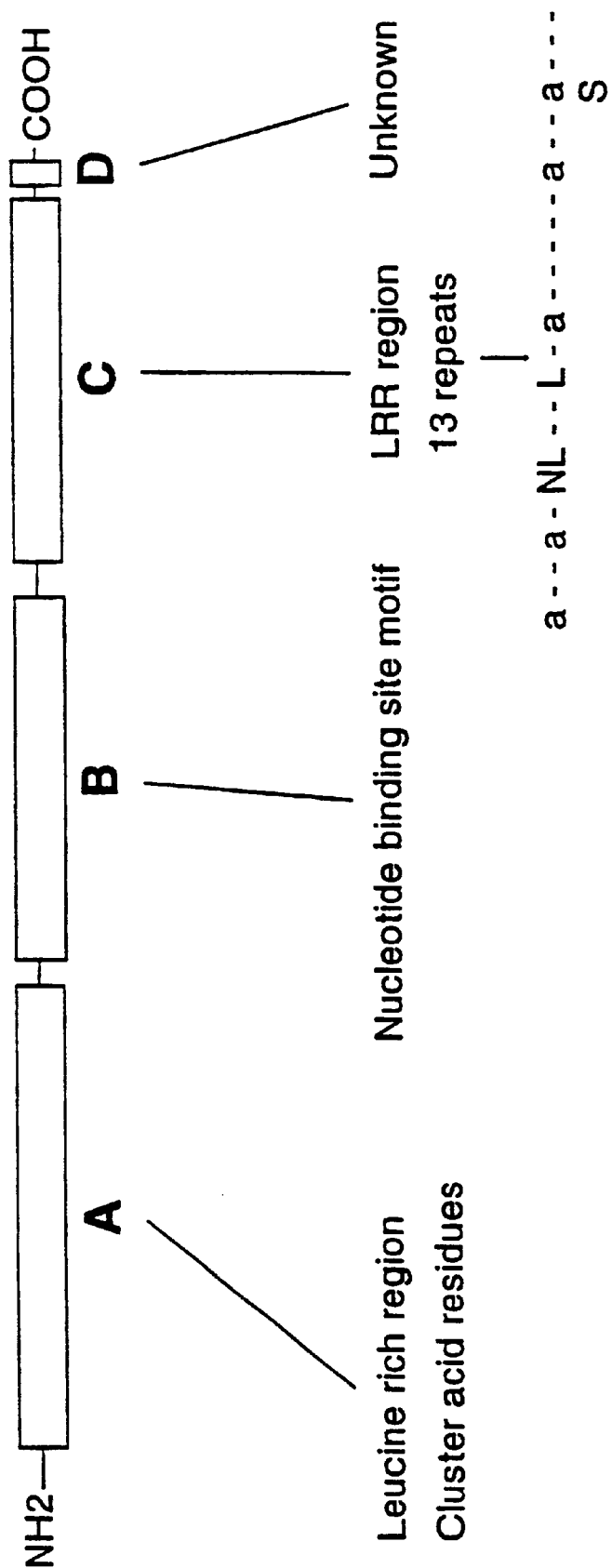

FIG. 8 depicts a schematic representation of the structure of the Mi-resistance gene.

Figure 9:
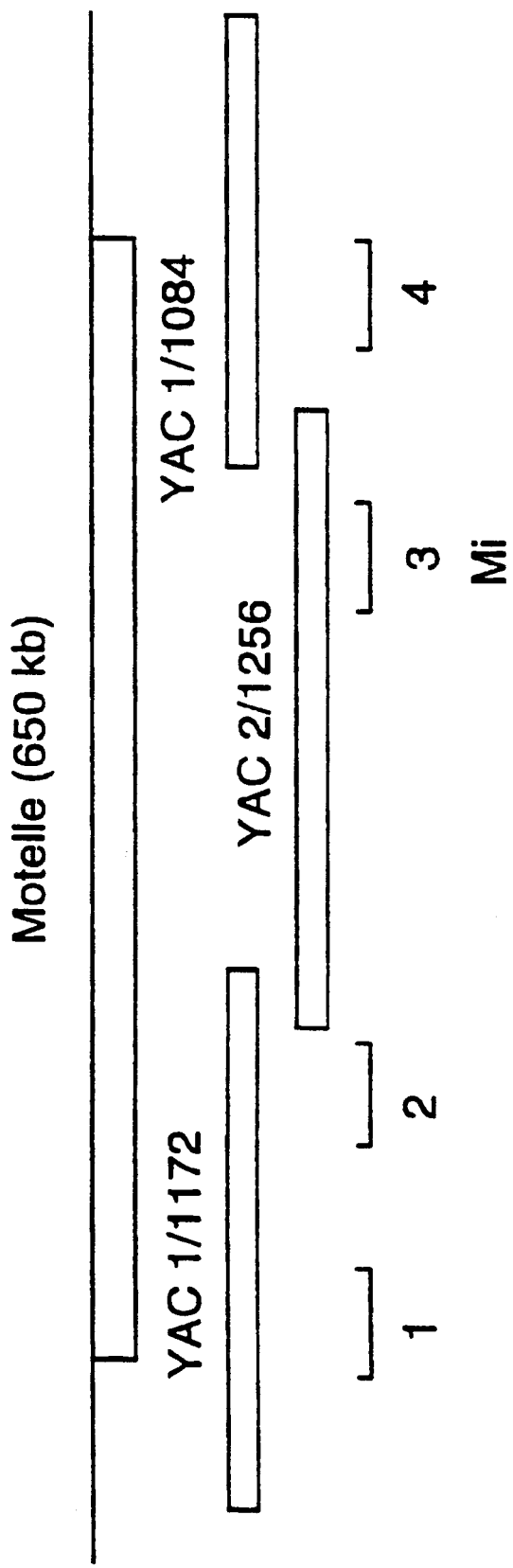

FIG. 9 depicts a schematic representation of the Mi-resistance gene family.

DETAILED DESCRIPTION OF THE INVENTION

In the description and examples that follow, a number of terms are used herein. In order to provide a clear and consistent understanding of the specification and claims, including the scope to be given such terms, the following definitions are provided.

nucleic acid: a double-stranded DNA molecule. The nucleic acid can be genomic DNA, cDNA, synthetic DNA or any other DNA;

oligonucleotide: a short single-stranded DNA molecule;

primers: in general, the term primer refers to a single-stranded DNA molecule which can prime the synthesis of DNA;

nucleic acid hybridization: a method for detecting related DNA sequences by hybridization of single-stranded DNA on supports such as nylon membrane or nitrocellulose filter papers. Nucleic acid molecules that have complementary base sequences will reform the double-stranded structure if mixed in solution under the proper conditions. The double-stranded structure will be formed between two complementary single-stranded nucleic acids even if one is immobilized on a support. In a Southern hybridization procedure, the latter situation occurs;

hybridization probe: to detect a particular DNA sequence in the Southern hybridization procedure, a labelled DNA molecule or hybridization probe is reacted to the fractionated DNA bound to a support such as nylon membrane or nitrocellulose filter paper. The areas on the filter that carry DNA sequences complementary to the labelled DNA probe become labelled themselves as a consequence of the reannealing reaction. The areas of the filter that exhibit such labelling can then be detected according to the type of label used. The hybridization probe is generally produced by molecular cloning of a specific DNA sequence or by synthesizing a synthetic oligonucleotide;

homologous sequence: a sequence which has at least 50%, preferably 60%, more preferably 70%, most preferably 80% or even 90% sequence identity with the particular sequence, whereby the length of sequences to be compared for nucleic acids is generally at least 120 nucleotides, preferably 200 nucleotides and more preferably 300 nucleotides and the length of sequences to be compared for polypeptides is generally at least 40 amino acid residues, preferably 65 amino acid residues and more preferably 100 amino acid residues. Alternatively, a homologous sequence refers to a sequence which can hybridize under stringent conditions to a particular sequence, and/or a DNA sequence coding for a polypeptide which has substantially the same properties as the polypeptide encoded by the particular DNA sequence, and/or a DNA sequence coding for a polypeptide having the same amino acid sequence as the polypeptide encoded by the particular DNA sequence and/or an amino acid sequence in which some amino acid residues have been changed with respect to the amino acid sequence of the particular polypeptide without substantially affecting the major properties of said polypeptide;

stringent conditions refer to hybridization conditions which allow a nucleic acid sequence to hybridize to a particular sequence. In general, high stringent conditions refer to the hybridization conditions which allow a nucleic acid sequence of at least 50 nucleotides and preferably about 200 or more nucleotides to hybridize to a particular sequence at about 65° C. in a solution comprising about 1 M salt, preferably 6×SSC or any other solution having a comparable ionic strength, and washing at 65° C. in a solution comprising about 0,1 M salt, or less, preferably 0,2×SSC or any other solution having a comparable ionic strength. These conditions allow the detection of sequences having about 90% or more sequence identity. In general, lower stringent conditions refer to the hybridization conditions which allow a nucleic acid sequence of at least 50 nucleotides and preferably about 200 or more nucleotides to hybridize to a particular sequence at about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. These conditions allow the detection of sequences having up to 50% sequence identity. The person skilled in the art will be able to modify these hybridization conditions in order to identify sequences varying in identity between 50% and 90%;

promoter: a transcription regulation region upstream from the coding sequence containing the regulatory sequences required for the transcription of the adjacent coding sequence and includes the 5' non-translated region or so called leader sequence of mRNA;

terminator a region downstream of the coding sequence which directs the termination of the transcription, also called the 3' non-translated region, which includes the poly-adenylation signal;

resistance gene: a nucleic acid comprising a coding sequence as depicted in FIG. 5, or part thereof, or any corresponding or homologous sequence;

nematode(s): Meloidogyne spp. such as Meloidogyne incognita, M. arenalia or M. javanica, or any other genotype which is not able to infect a host having a resistance gene according to the invention, such as but not limited to other root-knot nematodes, such as M. hapla, cyst nematodes such as Heterodera spp. or Globodera spp., or other nematodes such as Nacobbus spp., insects, such as potato aphid or any other plant pathogen or pest;

resistance gene product: a polypeptide having an amino acid sequence as depicted in FIG. 5, or part thereof, or any homologous amino acid sequence;

R₀ plant: primary regenerant from a transformation experiment, also denoted as transformed plant or transgenic plant;

R₁ line: the progeny of a selfed R₀ plant.

R₂ line: the progeny of a selfed R₁ plant.

R₁BC line: the progeny of a backcross between a R₁ plant and a plant of the genotype which was originally used for the transformation experiment.

In the present invention we have been able to identify and isolate the *Meloidogyne incognita* (*Mi*) resistance gene. The gene was cloned from a tomato genotype which is resistant to *Meloidogyne incognita*. The isolated *Mi* resistance gene according to the invention can be transferred to a susceptible host plant using Agrobacterium mediated transformation or any other known transformation method, and is involved in conferring to the host plant resistance against plant pathogens, especially to nematodes. The host plant can be tomato or any other genotype that is infected by said plant pathogen.

The present invention provides also a nucleic acid sequence comprising the *Mi* resistance gene, which is depicted in FIG. 5.

With the *Mi* resistance gene according to the invention, one has an effective means of control against plant pathogens and/or pests, since the gene can be used for transforming susceptible plant genotypes thereby producing genetically transformed plants having a reduced susceptibility or being preferably resistant to a plant pathogen or pest. In particular, a plant which is genetically transformed with the *Mi* resistance gene according to the invention has a reduced susceptibility to root-knot nematodes.

In a preferred embodiment the *Mi* resistance gene comprises the coding sequence provided in FIG. 5 or any corresponding or homologous sequence or cDNA sequence, preceded by a promoter region and followed by a terminator region. The promoter region should be functional in plant cells and, preferably, corresponds to the native promoter region of the *Mi* resistance gene. However, it should be recognized that any heterologous promoter region can be used in conjunction with the coding sequences, as long as it is functional in plant cells. Preferably, a constitutive promoter is used, such as the CaMV 35 S promoter or T-DNA promoters, all well known to those skilled in the art. Furthermore, a suitable terminator region should be functional in plant cells all well known to those skilled in the art.

In addition the invention relates to the *Mi* resistance gene product which is i encoded by the *Mi* resistance gene according to the invention and which has a deduced amino acid sequence provided in FIG. 5 and FIG. 7A, or which is homologous to the deduced amino acid sequence or part thereof. Furthermore, the *Mi* resistance gene product or a truncated polypeptide as provided in FIG. 7B can be used for raising antibodies against it, which antibodies can be used for the detection of the presence of the *Mi* resistance gene product.

In another aspect of the invention, the *Mi* resistance gene can be used for the design of oligonucleotides which are complementary to one strand of the DNA sequence as described in FIG. 5, or part thereof, which can be used as hybridization probes, being accordingly labelled to allow detection, for the screening of genomic DNA or cDNA libraries for homologous genes. Homologous sequences which can hybridize to the probe under stringent hybridization conditions, and which encode for a gene product that is involved in conferring reduced susceptibility or resistance to a plant against a plant pathogen which normally infects said plant, are comprised within the scope of the present invention.

In another aspect of the invention oligonucleotides are designed based on the *Mi* resistance gene sequence, such that they can be used as hybridization probes in Southern analysis. These probes can be used as molecular markers to distinguish plant genotypes having the resistance gene and plant genotypes lacking the resistance gene. Such a probe can be used as an additional tool in selection. In a preferred embodiment of the invention, oligonucleotides are designed based on the *Mi* resistance gene sequence, such that they can be used as primers in an amplification reaction, such as polymerase chain reaction (PCR), whereby the formation of an amplification product indicates the presence of the *Mi* resistance gene in a certain plant genotype. In a particular embodiment of the invention said primers direct the amplification of polymorphic fragments, so called molecular markers, which are closely linked to the *Mi* resistance gene. In a preferred embodiment said primers are used in selective restriction fragment amplification to identify AFLP markers, which are closely linked to the *Mi* resistance gene. The invention also relates to diagnostic kits, comprising oligonucleotides according to the invention, for the detection of the presence or absence of the *Mi* resistance gene within a genotype under study. Such a diagnostic kit circumvents the use of a laborious disease assay to screen for genotypes having the resistance gene or not.

Furthermore the invention relates to DNA constructs comprising a DNA sequence corresponding to the coding sequence of the *Mi* resistance gene and regulatory sequences functional in plant cells, said DNA sequence can be genomic DNA, cDNA, synthetic DNA or DNA of any other origin. Said regulatory sequences are either homologous or heterologous to the coding sequences of the *Mi* resistance gene. Preferably, said DNA construct comprises a nucleic acid whose sequence is provided in FIG. 5, or part thereof.

The invention relates also to DNA constructs comprising the regulatory sequences, and more preferably the promoter region of the *Mi* resistance gene in conjunction with a structural gene sequence heterologous to said regulatory sequences.

The invention relates also to a DNA vector comprising a DNA construct according to the invention. Suitable vectors can be cloning vectors, transformation vectors, expression vectors, etc. . . . , which are well known to those skilled in the art.

Furthermore, cells harbouring a vector comprising a DNA sequence corresponding to the sequence as described in FIG. 5 or part thereof, or homologous thereto, are within the scope of the invention. Moreover, cells carrying a DNA construct according to the invention, are within the scope of this invention.

In one preferred embodiment of the invention, a genetically transformed plant is obtained by introducing the *Mi* resistance gene within the genome of said plant, being susceptible to nematodes, using standard transformation techniques, wherein said genetically transformed plant is resistant to nematodes.

In another embodiment of the invention, the *Mi* resistance gene can be transferred, using generally known transformation techniques, to a heterologous systems, such as but not limited to melon, tobacco, *Arabidopsis thaliana*, potato, sugarbeet, rapeseed, cucumber, pepper, eggplant. A heterologous system refers to a plant species which is different from the plant species from which the resistance gene was isolated.

In yet another embodiment of the invention, the *Mi* resistance gene corresponds to the *Macrosiphum euphorbiae* (*Meu*-1) resistance gene, and is involved in conferring to plants, transformed with the gene according to the invention, resistance to insects and in particular to aphids.

The DNA sequence comprising the *Mi* resistance gene as provided in the present invention has numerous applications of which some are described herein but which are not limiting the scope of the invention.

The present invention will be further described in detail in view of the isolation of the Mi resistance gene present in tomato lines which are resistant to root-knot nematodes. For the isolation of the Mi resistance gene we have used a map-based cloning (positional cloning) strategy, comprising the following steps:

(1) identification of molecular markers linked to the Mi resistance gene, (2) construction of a high molecular weight genomic YAC library, (3) physical mapping of the molecular markers on the YAC clones and YAC contig building, (4) construction of a cosmid library of the YAC clones harbouring the linked molecular markers, (5) physical fine mapping and cosmid contig building, (6) genetic characterization of tomato mutants susceptible to root-knot nematodes, (7) transformation of susceptible plants with the cosmids forming the contig, (8) complementation analysis.

For the identification of molecular markers, we have used the selective restriction fragment amplification technology, hereinafter also denoted as AFLP™ technology, which randomly amplifies a subset of DNA fragments out of a complex mixture of many DNA fragments and said amplified fragments generate fingerprints that can be analyzed. In general, total DNA of different genotypes of the same plant species are subjected to the AFLP technology and the different AFLP fingerprints obtained from the different genotypes are compared. Fragments that are present in one genotype and absent in another genotype are polymorphic fragments and are denoted as AFLP markers. The selectivity in AFLP reactions is obtained by using randomly chosen selective nucleotides at the 3' end of the PCR primers immediately adjacent to the nucleotides of the restriction enzyme site. In an AFLP screening the DNA to be studied is subjected to different primer combinations. The total amount of different primers that can be used is determined by the number of selective nucleotides that are added to the 3' end (4 primers with 1 selective nucleotides, 16 primers with 2 selective nucleotides, 64 primers with 3 selective nucleotides). If two different restriction enzymes are used than there are twice the amount of primers. Those primers can be used in different combination. If all possible combinations are used in an AFLP screening, than all the fragments present should have been amplified with one of the primer combinations (Zabeau and Vos, EP 0534858).

For the identification of AFLP markers linked to the Mi resistance gene different tomato lines were subjected to an AFLP screening. In a first step, two sets of nearly isogenic lines for nematode resistance versus susceptibility were analyzed by AFLP fingerprinting using the following primers:

PstI-primers 5'-GACTGCGTACATGCAGNN-3' (SEQ ID NO: 1)

MseI-primers 5'-GATGAGTCCTGAGTAANNN-3' (SEQ ID NO:2).

The N's indicate the variable selective nucleotides. In the AFLP screening all 16 primers possible for the PstI-primer and all 64 primers possible for the MseI-primer were used on the two sets of nearly isogenic lines, giving a total of 16×64=1024 tested primer combinations. Upon analysis of all the AFLP fingerprints a total of 30 candidate AFLP markers linked to the Mi resistance gene were identified. These candidate markers were subsequently tested on a panel of nematode resistant and nematode susceptible tomato lines for confirmation and distance of linkage to the Mi locus. The Mi resistance gene was introgressed in the cultivated tomato in 1944 from Lycopersicon peruvianum. Modem nematode resistant tomato lines have been subjected to numerous cycles of crossing expected to result in a small introgressed region from Lycopersicon peruvianum with the Mi resistance gene. Testing of the candidate AFLP markers on these modern tomato genotypes is expected to be a good test for assessing close linkage to the Mi locus. A panel of 7 resistant and 11 susceptible tomato genotypes was tested with the candidate AFLP markers. A total of 20 AFLP markers appeared to be present in all resistant lines and absent in all susceptible lines and are referred to as Mi linked AFLP markers.

Next, four of the AFLP markers were screened on a high molecular weight genomic library. The cloning of very large segments of DNA as large artificial chromosomes in yeast has become an essential step in isolating genes via positional cloning. The cloning capacity of the YAC vector allows the isolation of DNA fragments up to one million base pairs in length. The tomato line Lycopersicon esculentum E22, homozygous for the Mi locus, was used as source DNA to construct a YAC library. We obtained a YAC library containing 3840 clones with an average insert size of 520 Kb, representing approximately 2.2 genome equivalents of the tomato genome. Three positive YAC clones were obtained after the AFLP screening with the Mi linked AFLP markers: 1/1084, 1/1172 and 2/1256. Subsequently, the presence of all Mi linked AFLP markers was determined in the 3 YAC clones. All markers appeared present in one or more of the 3 YAC clones, which allowed a first positioning of the various Mi linked AFLP markers. The AFLP data indicated that the 3 YAC clones constituted an overlapping contig of approximately 1.4 Mb (see FIG. 1).

To determine the physical size of the Mi locus comprising the Mi linked AFLP markers and comprised in YAC clones 1/1084, 1/1172 and/or 2/1256 a long-range restriction map of the YAC contig was constructed. This defined a DNA segment comprising the Mi locus of about 700 kb on which all the Mi linked AFLP markers were located (see FIG. 1).

A size of 700 kb is still too large for direct localization of the Mi resistance gene. Such large inserts cannot be transformed into plant cells directly. Therefore, a cosmid library was constructed of the yeast strain containing YAC 1/1172 and a cosmid library was constructed of the yeast strain containing YAC 2/1256 using cosmid vectors which are suitable for Agrobacterium mediated transformation. The size of this binary cosmid vector amounts 29 kb and is shown schematically in FIG. 2. The cloning capacity of this binary cosmid vector, using phage lambda packaging extract is within the range of 9 to 24 kb. Two banks of approximately 250,000 cosmid clones each were obtained from size fractionated yeast DNA. The cosmid banks were screened by colony hybridization using as probes labelled restriction fragments of the YACs. Positive cosmids clones were identified and in addition, the cosmids were grouped into seven defined regions covering the Mi region.

Figure 3A:
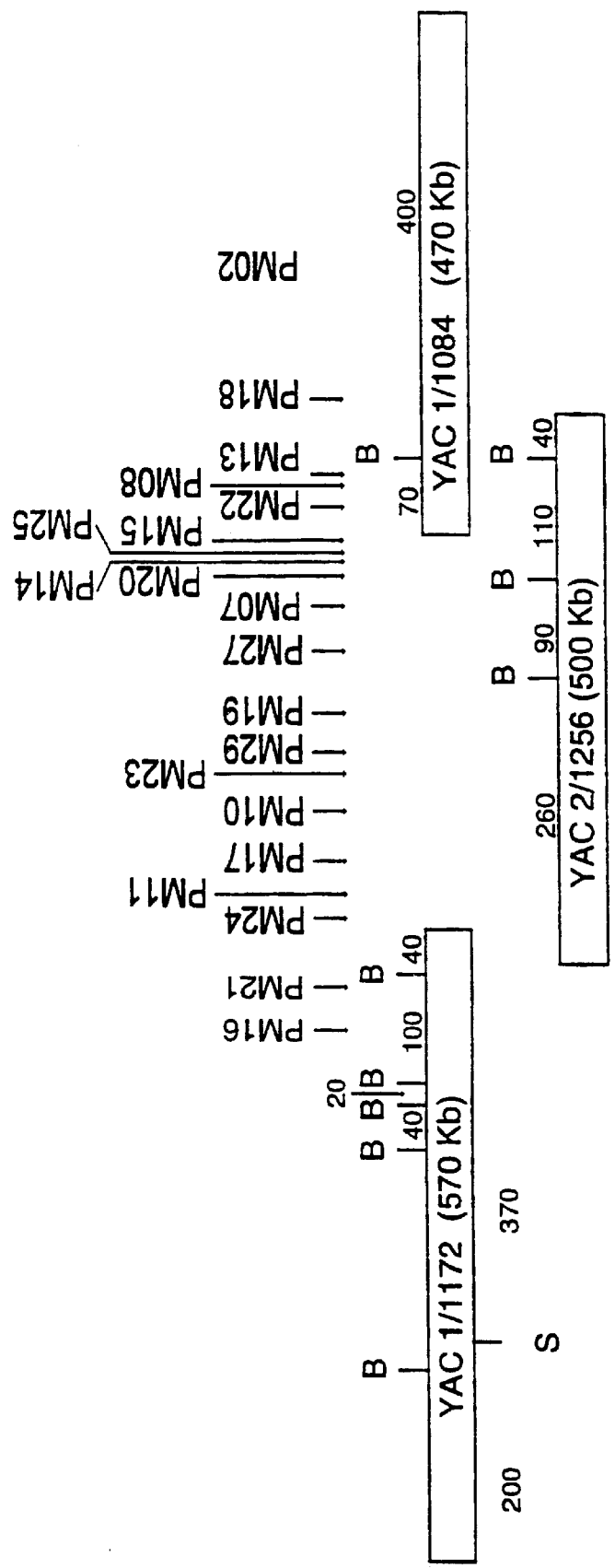
FIG. 3A shows a schematic representation of the detailed position of the AFLP markers on YAC 1/1172, YAC 2/1256 and YAC 1/1084. Positioning is based on the cosmid contig constructed for the various defined regions.

In the following step the set of cosmids of the seven defined regions were fingerprinted using restriction fragment amplification to determine their relative order. A cosmid contig covering a DNA segment of approximately 700 kb could be constructed. Subsequently, the presence of the Mi linked AFLP markers in this cosmid contig was determined. A physical map of the DNA segment comprising the Mi resistance gene with the positions of the various Mi linked AFLP markers was obtained (see FIG. 3).

A total of 96 overlapping cosmids together constituted the DNA segment comprising the Mi resistance gene. Complementation analysis to identify the Mi resistance gene with such a large set of cosmids is a very laborious task. Therefore, the position of the Mi resistance gene on the cosmid contig was determined using mutant tomato lines. These mutant lines are members from a family originating from a common ancestor and contained a wild-type (nematode resistant) Mi genotype but a mutant nematode susceptible phenotype. Upon analysis with the set of Mi linked AFLP markers on a large number of these mutant lines three Mi linked AFLP markers appeared to be absent in most mutants. These AFLP markers, therefore showed a good correlation between the AFLP Mi genotype and the Mi phenotype, in contrast to all other 17 AFLP markers. Two of these AFLP markers, PM14 and PM25 were adjacent, and the region around these markers was assumed to be the most likely position for the Mi resistance gene. A set of 6 overlapping cosmids defining a DNA segment of approximately 50 kb around AFLP markers PM14 and PM25 was selected for complementation analysis (see FIG. 4).

The final step in the identification of the Mi resistance gene via positional cloning is the complementation of the corresponding susceptible phenotype. The 6 cosmids from the candidate Mi region were introduced in Agrobacterium tumefaciens through conjugative transfer in a tri-parental mating. The presence of the cosmid in the *A. tumefaciens* strains was determined comparing various restriction enzyme patterns as well as DNA fingerprints from the *A. tumefaciens* strains with the *E.coli* strain containing the cosmid. Only those *A. tumefaciens* cultures harbouring a cosmid with the same DNA pattern as the corresponding *E. coli* culture were used to transform a susceptible tomato line. A susceptible tomato line was transformed with cosmids Mi-32, Mi-30, Mi-1. Mi-18, Mi-01 and Mi-14 using standard transformation methods.

Roots of in vitro grown transformed $R_0$ plants were tested for disease symptoms in order to identify cosmids with the resistance gene. Root explants were transferred onto solidified medium in petri dishes and inoculated with ten galls from an axenic nematode culture of the root-knot nematode *Meloidogyne incognita*. Disease symptoms are scored six weeks after inoculation. A transgenic plant is considered resistant when no galls or one gall are visible on its root culture. A transgenic plant is considered susceptible when at least two galls have been induced on its root culture. The observations of the in vitro disease assay revealed that 2 cosmids were able to complement the susceptible phenotype. The presence of the AFLP marker PM14 in the resistant $R_0$ plants indicated that the genomic insert present in cosmids Mi-11 and Mi-18 is also present in the $R_0$ plants and is involved in conferring the $R_0$ plants resistant to *Meloidogyne incognita*.

The primary regenerants ($R_0$ plants) of the transformation experiments were grown in the greenhouse for seed set to obtain $R_1$ lines which were tested for disease symptoms. The disease assay is performed on seedlings. Therefor, seeds are sown or small rooted plantlets are transferred into soil infected with *Meloidogyne incognita* and disease symptoms are scored 4 to 8 weeks after inoculation. Plants are considered to be resistant when three or less galls are visible on the roots. Plants are considered to be susceptible when more than three galls are formed on the roots. The observations of the in vivo disease assay revealed that the resistant $R_0$ plants are corresponding to cosmid Mi-11 transformants.

In order to confirm the stable integration of the Mi resistance gene into the genome of the transgenic $R_0$ plants, resistant plants of the $R_1$ lines were selfed and grown in the greenhouse for seed set to obtain $R_2$ lines. Seedlings of the $R_2$ lines were subjected to an in vivo nematode disease assay. The results obtained indicated the stable inheritance of the Mi resistance gene.

Finally, the inserts in cosmids Mi-11 and Mi-18 were further characterized. Sequencing analysis revealed a large open reading frame (ORF2) of 3621 nucleotides. The DNA sequence is listed in FIG. 5.

The DNA sequence comprising the Mi resistance gene was further subjected to transcript mapping studies in order to determine the existence of intron sequences. These transcripts mapping studies were performed according to generally known methods whereby genomic DNA sequences are compared with cDNA sequences. The comparison of cDNA sequences and genomic sequences revealed the existence of two intron sequences in the Mi resistance gene. One intron of 1306 nucleotides is located from nucleotide position 1936 to 3241 and a second intron of 75 nucleotides is located from nucleotide position 3305 to 3379, as is depicted in FIG. 5. The position of the transcription initiation site is postulated at or upstream of nucleotide 1880. The first ATG initiation codon is located at nucleotide position 3263 which is 52 nucleotides upstream of the second intron, giving a large open reading frame (ORFL) encoding a polypeptide of 1257 amino acids (FIG. 7A).

Homology searches have shown that the polypeptides according to the invention belong to the LRR class of plant resistance proteins (Staskawicz et al, 1995, Science, 268, 661–667). In addition the protein can be divided into four regions designated A to D: region A comprises a high amount of leucine residues, region B comprises a nucleotide binding site motif, region C is the LRR region comprising 13 repeats with the following consensus sequence a-a-NL-L-a-a-a/S-(Jones and Jones, 1997, Advances in Botanical Research, 24, 89–167) and region D reveals no homology to any known protein.

For the identification and isolation of homologous sequences falling within the scope of the present invention, genomic and cDNA libraries were screened with the coding sequence of the Mi resistance gene as a probe under stringent hybridization conditions. Positive clones were isolated and used for complementation analysis.

Southern blot hybridizations on the YAC contig have been performed with an internal PstI fragment of the coding sequence of the Mi resistance gene. Three additional homologous regions could be identified: two in YAC 1/1172 and one in YAC 1/1084. Each region comprises 2 to 3 Mi homologues indicative of the fact that the Mi gene family is composed of about 10 to 12 members.

Surprisingly, aphid disease assays revealed that the $R_0$ plants, transformed with cosmid Mi-11, are resistant to *Meloidogyne incognita* as well as resistant to *Macrosiphum euphorbiae*, indicating that the genome insert present in cosmid Mi-11 is involved in conferring the $R_0$ plants resistant to nematodes as well as involved in conferring the $R_0$ plants resistant to aphids. In particular, a plant which is transformed with the resistance gene according to the invention has at least a reduced susceptibility to one or more pathogens, especially to root-knot nematodes and/or aphids.

In order to confirm the inheritance of the aphid resistance, (i) the previously obtained $R_1$ tomato lines which were derived from nematode resistant cosmid Mi-11 transformants, (ii) the $R_2$ lines derived from selfed nematode resistant $R_1$ plants and (iii) $R_1BC$ lines obtained from nematode resistant $R_1$ plants backcrossed with susceptible tomato line 52201, were also tested for resistance against M.

*euphorbiae*. The results obtained indicated the inheritance of the aphid resistance.

Cosmid *Mi*-11 was used for the transformation of nematode susceptible genotypes of tobacco and potato, according to general known transformation methods. Roots of in vitro grown transformed $R_0$ plants of tobacco and potato were tested for disease symptoms as previously described herein. The observations of the disease assay on the root cultures of the transformed plants indicated that the cosmid is involved in conferring to the transformed plants a reduced susceptibility to nematodes. The resistance gene according to the invention has an effect in reducing the susceptibility of a heterologous plant species to nematodes, preferably to Meloidogyne spp., especially *Meloidogyne incognita*.

Furthermore tobacco transformants were also tested for aphid resistance, and resistant $R_0$ plants could be identified.

The resistance gene according to the invention has a dual function and has an effect in heterologous systems.

Cosmid *Mi*-11 has been deposited on Aug. 5, 1996 as plasmid pKG*Mi*-11 at Centraalbureau voor Schimmelcultures at Baarn, The Netherlands, under deposit number CBS 822.96.

Cosmid *Mi*-18 has been deposited on Aug. 5, 1996 as plasmid pKG*Mi*-18 at Centraalbureau voor Schimmelcultures at Baarn, The Netherlands, under deposit number CBS 821.96.

The following examples will provide a further illustration of the present invention which is nevertheless not limited to these examples.

EXAMPLES

Example 1

Disease Assay

An axenic culture of the root-knot nematode *Meloidogyne incognita* is maintained on sterle roots of the tomato cultsvar Moneymakern The root cultures are grown on solidified B5 medium (Gamborg et al 1968, Experimental Cell Research 50: 151–158) with 2% saccharose and without hormones.

Root explants (1–5 cm) deved from in vitro grown transgenic tomato plants are transferred onto the solidified B5 medium mentioned above to start root cultures. At the same time each root explant is inoculated with ten galls from the axenic nematode culture. The galls are placed a few centimeters from the root explant. The Petri dishes with the roots and galls are incubated in the dark at 25° C. After four to six weeks the level of infection is determined by counting the number of galls formed on the root cultures.

The evaluation for resistance/susceptibility to *M. incognita* is as follows:

A transgenic plant is considered resistant when no or less than two galls are visible on its root culture. A transgenic plant is considered susceptible when at least two galls have been induced on its root culture.

Example 2

Identification of AFLP Markers Linked to a DNA Segment Comprising the *Mi* Resistance Gene Tomato lines (*Lycopersicon Esculentum*)

A total of 9 tomato lines resistant to *Meloidogyne incognita* and 13 tomato lines susceptible to *M. incognita* were used to identify AFLP markers. Initially the AFLP screening was performed on two sets of nearly isogenic lines 83M-R (resistant) and 83M-S (susceptible), and Motelle (resistant) and Mobox (susceptible). The candidate markers resulting from this first screening were confirmed by a second screening on 7 *M. incognita* resistant and 1g1 *M. incognita* susceptible lines.

Two sets of nearly isogenic lines:

| | | |
|---|---|---|
| 1. 83M-R | resistant | De Ruiter Zonen C. V., Bergschenhoek, The Netherlands (hereinafter "De Ruiter") |
| 2. 83M-S | susceptible | De Ruiter |
| 3. Motelle | resistant | INRA, Montfavet, France |
| 4. Mobox | susceptible | INRA, Montfavet, France |

The 7 *M. incognita* resistant lines and 11 *M. incognita* susceptible lines for confirmation:

| | | |
|---|---|---|
| 5. DR30 | resistant | De Ruiter |
| 6. DR17 | resistant | De Ruiter |
| 7. E22 | resistant | Enza Zaden, de Enkhuizer Zaadhandel B. V., Enkhuizen, The Netherlands (hereinafter "Enza Zaden") |
| 8. E1 | resistant | Enza Zaden |
| 9. DR6 | resistant | De Ruiter |
| 10. DR10 | resistant | De Ruiter |
| 11. 1872 | resistant | Royal Sluis B. V., Enkhuizen, The Netherlands (hereinafter "Royal Sluis") |
| 12. Moneymaker | susceptible | Agricultural University Wageningen |
| 13. DR12 | susceptible | De Ruiter |
| 14. DR23 | susceptible | De Ruiter |
| 15. GT | susceptible | De Ruiter |
| 16. RZ3 | susceptible | Rijk Zwaan Zaadteelt en Zaadhandel B. V., De Lier, The Netherlands (hereinafter "Rijk Zwaan") |
| 17. RZ5 | susceptible | Rijk Zwaan |
| 18. E3 | susceptible | Enza Zaden |
| 19. E7 | susceptible | Enza Zaden |
| 20. E16 | susceptible | Enza Zaden |
| 21. RS1 | susceptible | Royal Sluis |
| 22. RS2 | susceptible | Royal Sluis |

Isolation and Modification of the DNA

Total tomato DNA from the 22 lines described above was isolated from young leaves as described by Bematzki and Tanksley (Theor. Appl. Genet. 72, 314–321). The typical yield was 50–100 μg DNA per gram of fresh leaf material. Template DNA for AFLP analysis with the enzyme combination PstI-MseI was prepared as described by Zabeau and Vos (European Patent Application, EP 0534858), and is described briefly below.

0.5 μg of tomato DNA was incubated for 1 hour at 37° C. with 5 units PstI and 5 units MseI in 40 μl 10 mM Tris.HAc pH 7.5, 10 mM MgAc, 50 mM KAc, 5 mM DTT, 50 ng/μl BSA. Next 10 μl of a solution containing 5 pMol PstI-adapters, 50 pMol MseI-adapters, 1 unit T4 DNA-ligase, 1 mM ATP in 10 mM Tris.HAc pH 7.5, 10 mM MgAc, 50 mM KAc, 5 mM DTT, 50 ng/μl BSA was added, and the incubation was continued for 3 hours at 37° C. The adapters are depicted below:

The structure of the PstI-adapter was (SEQ ID NOs: 3 and 4)

5'-CTCGTAGACTGCGTACATGCA-3'
3'-CATCTGACGCATGT-5'

The structure of the MseI-adapter was (SEQ ID NOs: 5 and 6)

5'-GACGATGAGTCCTGAG-3'
3'-TACTCAGGACTCAT-5'

Adapters were prepared by adding equimolar amounts of both strands; adapters were not phosphorylated. After ligation, the reaction mixture was diluted to 500 μl with 10 mM Tris.HCl, 0.1 mM EDTA pH 8.0, and stored at −20° C. The diluted reaction mixture is further referred to as template DNA.

AFLP Reactions

The primers used for the AFLP screening are depicted below:

PstI-primers 5'-GACTGCGTACATGCAGNN-3' (SEQ ID NO: 1)

MseI-primers 5'-GATGAGTCCTGAGTAANNN-3' (SEQ ID NO 2).

The N's in the primers indicate that this part of the primers was variable. In the AFLP screening all 16 possible primers were used for the PstI-primer and all 64 possible primers were used for the MseI-primer. This gave a total of 16×64 combinations of PstI- and MseI-primers, is 1024 primer combinations. All 1024 primer combinations were used in the AFLP screening for Mi linked AFLP markers. The AFLP reactions were performed in the following way:

AFLP reactions employed a radio-actively labelled PstI-primer and a non-labelled MseI-primer. The PstI-primers were end-labelled using $(\gamma^{33}P)ATP$ and T4 polynucleotide kinase. The labelling reactions were performed in 50 µl 25 mM Tris.HCl pH 7.5, 10 mM $MgCl_2$, 5 mM DTT, 0.5 mM spermidine.3HCl using 500 ng oligonucleotide primer, 100 µCi $(\gamma^{33}P)ATP$ and 10 units T4 polynucleotide kinase. For AFLP analysis 20 µl reaction mixture were prepared containing 5 ng labelled PstI-primer (0.5 µl from the labelling reaction mixture), 30 ng MseI-primer, 5 µl template-DNA, 0.4 units Taq-polymerase, 10 mM Tris.HCl pH 8.3, 1.5 mM $MgCl_2$, 50 mM KCl, 0.2 mM of all 4 dNTPs. AFLP reactions were performed using the following cycle profile: a 30 seconds DNA denaturation step at 94° C., a 30 seconds annealing step (see below), and a 1 minute extension step at 72° C. The annealing temperature in the first cycle was 65° C., was subsequently reduced each cycle by 0.7° C. for the next 12 cycles, and was continued at 56° C. for the remaining 23 cycles. All amplification reactions were performed in a PE-9600 thermocycler (Perkin Elmer Corp., Norwalk, Conn., USA).

Gel Analysis of AFLP Reaction Products

After amplification, reaction products were mixed with an equal volume (20 µl) of formamide dye (98% formamide, 10 mM EDTA pH 8.0, and bromo phenol blue and xylene cyanol as tracking dyes). The resulting mixtures were heated for 3 minutes at 90° C., and then quickly cooled on ice. 2 µl of each sample was loaded on a 5% denaturing (sequencing) polyacrylamide gel (Maxam and Gilbert, Methods in Enzymology 65, 499–560). The gel matrix was prepared using 5% acrylamide, 0.25% methylene bisacryl, 7.5 M urea in 50 mM Tris/50 mM Boric acid/1 mM EDTA. To 100 ml of gel solution 500 µl of 10% APS and 100 µl TEMED was added and gels were cast using a SequiGen 38×50 cm gel apparatus (Biorad Laboratories Inc., Hercules, Calif., USA). Sharktooth combs were used to give 97 lanes on the SequiGen gel units. 100 mM Tris/100 mM Boric acid/2 mM EDTA was used as running buffer. Electrophoresis was performed at constant power, 110 Watts, for approximately 2 hours After electrophoresis, gels were fixed for 30 minutes in 10% acetic acid dried on the glass plates and exposed to Fuji phospho image screens for 16 hours. Fingerprint patterns were visualized using a Fuji BAS-2000 phospho image analysis system (Fuji Photo Film Company Ltd, Japan).

AFLP Screening for Linked Markers

An AFLP screening was performed using all possible 1024 PstI-MseI primer combinations on the two sets of nearly isogenic lines. The aim was to identify AFLP markers present in both resistant lines and absent in both susceptible lines. AFLP gets contained the AFLP fingerprints of 24 primer combinations of the 4 isogenic lines, giving a total of 43 gels. A total of 30 AFLP markers were identified present in both resistant lines and absent in both susceptible lines. These markers are referred to as candidate Mi linked AFLP markers.

Next, AFLP reactions were performed to determine the presence of the 30 candidate markers on the 7 resistant and 11 susceptible tomato lines. Of the 30 candidate markers 20 markers appeared to be present in the 7 resistant lines and absent in the 11 susceptible lines. These 20 markers were used in further studies to map the Mi resistance gene. The primer combinations required to identify the 20 PstI-MseI markers are depicted in Table 1. In the column with the primer combinations. "PstI" refers to the sequence (SEQ ID NO: 7) 5'-GACTGCGTACATGCAG-3' AND "MseI-" refers to the sequence (SEQ ID NO: 8) 5'-GATGAGTCCTGAGTAA-3'. For example, marker PM14 can be identified using the PstI-primer having the following sequence: (SEQ ID NO: 9) 5'-GACTGCGTACATGCAGGA-3', and the MseI-primer having the following sequence: (SEQ ID NO: 10) 5'-GATGAGTCCTGAGTAATCT-3'.

TABLE 1

| marker | primer combination with selective extensions (NN/NNN) |
|---|---|
| PM02 | PstI-AT/MseI-AAA |
| PM07 | PstI-AA/MseI-TAC |
| PM08 | PstI-CT/MseI-ACT |
| PM10 | PstI-CA/MseI-TCT |
| PM11 | PstI-TA/MseI-TGA |
| PM13 | PstI-GA/MseI-ATC |
| PM14 | PstI-GA/MseI-TCT |
| PM15 | PstI-GT/MseI-GAC |
| PM16 | PstI-GT/MseI-TCT |
| PM17 | PstI-AT/MseI-AAG |
| PM18 | PstI-AT/MseI-TAG |
| PM19 | PstI-GG/MseI-ATT |
| PM20 | PstI-TG/MseI-AAT |
| PM21 | PstI-TG/MseI-TTT |
| PM22 | PstI-TG/MseI-GCT |
| PM23 | PstI-GT/MseI-GAA |
| PM24 | PstI-AA/MseI-CTG |
| PM25 | PstI-AC/MseI-GTG |
| PM27 | PstI-AA/MseI-CTA |
| PM29 | PstI-TA/MseI-GGA |

Example 3

Construction and Screening of a Tomato YAC Library

Material

The tomato line Lycopersicon esculentum E22 (Enza Zaden) homozygous for the Mi locus, was used as source DNA to construct a YAC library. Protoplasts were isolated from the leaves of in vitro shoots which were two to three weeks old as described by Van Daelen etal(Plant Mol. Biol. 12, 341–352).

Viable protoplasts (concentration of 50 million protoplasts per ml) were collected and mixed with an equal volume of agarose (1%, Seaplaque, FMC Bioproducts, Rockland, Me., USA) to form a plug. The protoplasts embedded into the plugs were lysed with lysis mix (0.5 M EDTA, 1% N-Laurylsarcosinate and 1 mg/ml proteinase K, pH=8.0). After lysis, the plugs were stored at 4° C. in storage buffer (fresh lysis mix) until used. Approximately 3 million protoplasts per plug, to obtain about 4.5 µg of chromosomal DNA were used for further studies. Plasmid pYAC4 containing an unique EcoRI cloning site was used as cloning vector and the yeast strain AB1380 was used as a host (Burke et al, Science 236, 806–812).

YAC Library Construction

High molecular weight DNA isolation, partial digestion with EcoRI in the presence of EcoRI methylase, ligation of vector arms to genomic DNA, size selection by pulsed field gel electrophoresis and transformation of the yeast host was performed as described by Burke et al, (Science 236, 806–812) and Larin et al, (Proc Natl Acad Sci USA 88, 4123–4127).

All standard manipulations were carried out as described in Molecular cloning: a laboratory manual by Sambrook et al, (Cold Spring Harbor Laboratory Press). 3840 clones with a average insert size of 520 kb, which corresponds to 2.2 genome equivalents were finally obtained and the individual clones were stored in 40 96-wells microtiter plates containing 75 µl YPD solution (1% yeast extract, 2% peptone and 2% dextrose).

Screening YAC Library

To reduce the number of samples handled, the cells of one 96-well microtiter plate were pooled (a platepool) and used for DNA isolation as described by Ross et al (Nucleic Acids Res. 19, 6053). The 2.2 genome equivalent tomato YAC library consists of 40 96-wells microtiter wells and as a result DNA of the 40 platepools were screened with the AFLP markers PM10, PM13, PM21 and PM25 using the AFLP protocol as described in Example 2. PM10, PM13, PM21 and PM25 were selected to screen the YAC platepools because these markers do not interfere with the background bands of the yeast strain AB1380. Three positive platepools out of the 40 were identified with these four AFLP markers as shown in Table 2. Subsequently, a secondary screening with the four AFLP markers (PM10, PM13, PM21 and PM25) of the 96 individual YAC clones of each plate was employed to find the correct address of the YAC clones. Three individual YAC clones were identified, designated 1/1084, 1/1172 and 2/1256 (Table 2). Subsequently, the three individual YAC clones were analyzed with the remaining AFLP markers. All of the identified markers PM02 to PM29 were present on one or more these three YAC clones (Table 3). The size of the YAC clone was determined by Pulse-field gel electrophoretic (PFGE) analysis using contour-clamped homogeneous electric field (CHEF; Chu et al Science, 235, 1582–1585) and appeared to be 470 kb (1/1084), 570 kb (1/1172), and 500 kb (2/1256) respectively.

TABLE 2

| Platepool nr | PM10 | PM13 | PM21 | PM25 | YAC detected (size in kb) |
|---|---|---|---|---|---|
| 2 | − | − | + | − | YAC 1/1172 (570 kb) |
| 16 | + | + | − | + | YAC 2/1256 (500 kb) |
| 4 | − | + | − | − | YAC 1/1084 (470 kb) |

TABLE 3

| Marker | 1/1172 | 2/1256 | 1/1084 |
|---|---|---|---|
| PM02 | − | − | + |
| PM07 | − | + | − |
| PM08 | − | + | + |
| PM10 | − | + | − |
| PM11 | − | + | − |
| PM13 | − | + | + |
| PM14 | + | + | − |
| PM15 | − | + | − |
| PM16 | + | − | − |
| PM17 | − | + | − |
| PM18 | − | + | + |
| PM19 | − | + | − |

TABLE 3-continued

| Marker | 1/1172 | 2/1256 | 1/1084 |
|---|---|---|---|
| PM20 | − | + | − |
| PM21 | + | − | − |
| PM22 | − | + | + |
| PM23 | − | + | − |
| PM24 | − | + | − |
| PM25 | − | + | − |
| PM27 | − | + | − |
| PM29 | − | + | − |

Example 4

Figure 1:
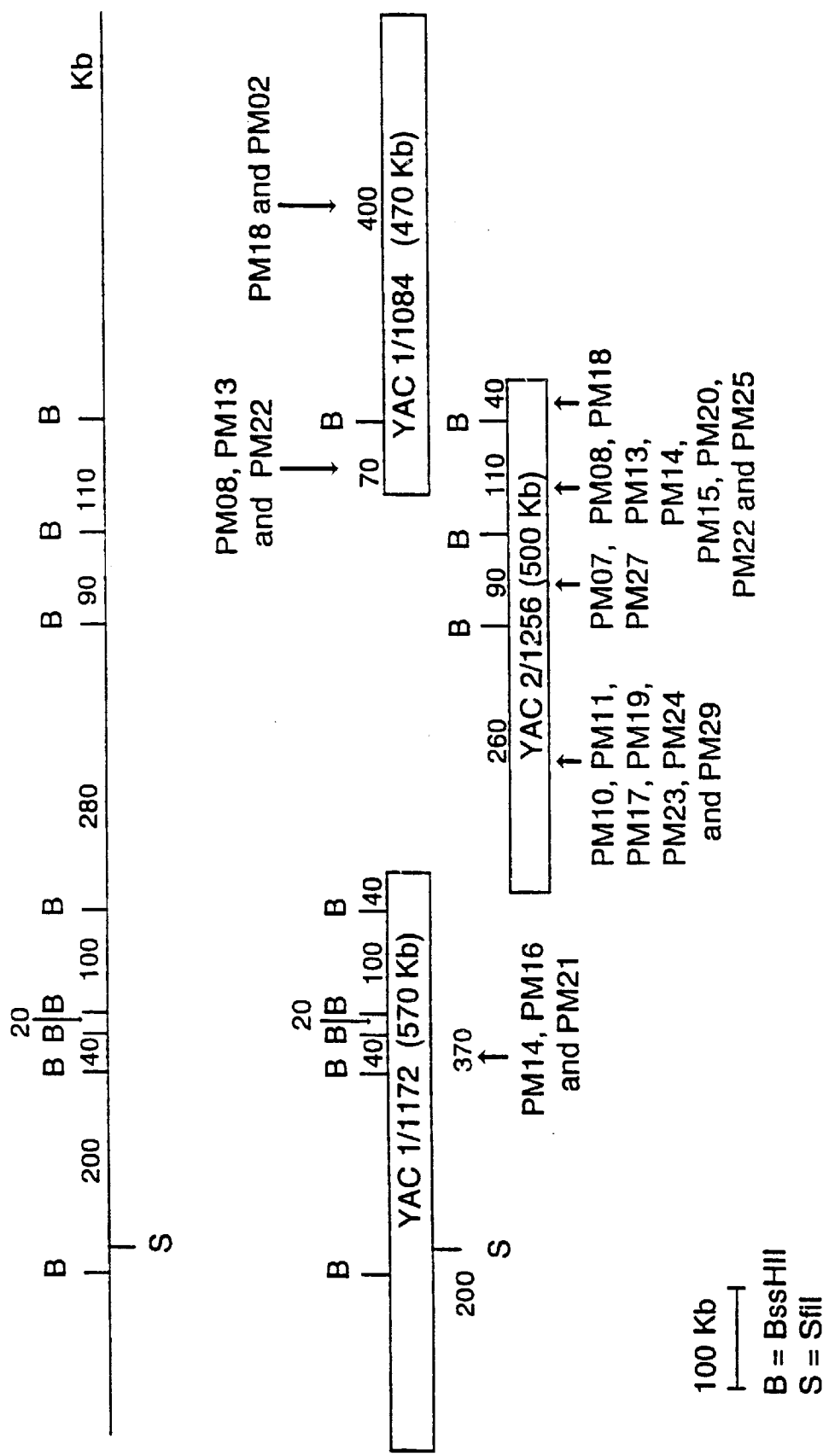
FIG. 1 shows a physical map of YAC 1/1172, YAC 2/1256 and YAC 1/1084, with a size of 570, 500 and 470 kb respectively. The position of the SfiI and BssHII restriction sites and the size of the restriction fragments are indicated. The location of the various AFLP markers on the restriction fragments are indicated.

Construction of a Long Range Physical map of the Mi YAC Contig and Location of the AFLP Markers The 3 YAC clones 1/1172, 2/1256 and 1/1084 were subjected to partial digestion with increasing concentration of the restriction enzymes SfiI and BssHII. The samples were fractionated by PFGE, transferred to a Gene Screen Plus membrane (DuPont NEN, Boston, Mass., USA) and assayed by hybridization using end-adjacent sequence probes according to the protocol for indirect end-label mapping as described by Burke et al (Science 236, 806–812). A physical map of YAC 111172, 2/1256 and 1/1084 for the enzymes SfiI and BssHII could be constructed as shown in FIG. 1. The overlap between the various YAC clones was determined by Southern blot analysis using the obtained restriction fragments as a probe on digest of the three YAC clones. A YAC contig with a size of 1.4 Mb could be constructed. In order to isolate the YAC fragments the digests were run on PFGE. Digestion of YAC 1/1172 with SfiI resulted in two fragments (200 Kb and 370 Kb). Digestion of YAC 2/1256 with BssHII resulted in four fragments (40 Kb, 90 Kb, 110 Kb and 260 Kb) whereas digestion of YAC 1/1084 with BssHII gave two fragments with a size of 70 and 400 kb. As a result the 1.4 Mb YAC contig could be dissected into 8 regions corresponding to the 8 restriction fragments obtained from the three YAC clones, covering the complete Mi region and adjacent sequences.

To position the various AFLP markers within these 8 regions on the physical map, the AFLP markers were used as hybridization probes on the partial and complete SfiI and BssHII digests of YAC clones 1/1172, 2/1256 and 1/1084. Therefore, each AFLP marker fragment was excised from the dried gel and eluted by means of diffusion in a buffer containing 0.5 M ammonium acetate, 10 mM magnesium acetate, 1 mM EDTA (pH=8.0), 0.1% SDS, re-amplified with the corresponding unlabelled AFLP primers and, subsequently labelled with $^{32}$P according to the random primer method of Feinberg and Vogelstein (Anal. Biochem. 132, 610). Each AFLP marker could be assigned to one or more of the eight regions as outlined in

TABLE 4

| YAC fragment | Mi linked AFLP markers detected by hybridization |
|---|---|
| 200 kb SfiI-fragment 1/1172 | — |
| 370 kb SfiI-fragment 1/1172 | PM14, PM16, PM21 |
| 260 kb BssHII-fragment 2/1256 | PM10, PM11, PM17, PM19, PM23, PM24, PM29 |
| 90 kb BssHII-fragment 2/1256 | PM07, PM27 |
| 110 kb BssHII-fragment 2/1256 | PM08, PM13, PM14, PM15, PM20, PM22, PM25 |

TABLE 4-continued

| YAC fragment | Mi linked AFLP markers detected by hybridization |
|---|---|
| 40 kb BssHII-fragment 2/1256 | PM18 |
| 70 kb BssHII-fragment 1/1084 | PM08, PM13, PM22 |
| 400 kb BssHII-fragment 1/1084 | PM02, PM18 |

Example 5

Construction of a Cosmid Library of YAC Clones 1/1172 and 2/1256

Material

The binary cosmid vector pJJ04541 is a derivative of pJJ1881 (Jones et al, Transgenic Research 1, 285–297) and is based on plasmid pRK290 containing the tetracyclin resistance gene for selection in *Eschenichia coli* and *Agrobacterium tumefaciens*. Into the unique EcoRI site of pRK290, T-DNA carrying sequences (LB; left border repeat, RB signifies the right border repeat) that flank the cos site of bacteriophage lambda the neomycin phosphotransferase gene (Beck et al., Gene 19, 327–336) whose expression is driven by the cauliflower mosaic virus 35S promoter sequence (Odell et al, Mol Gen Genet 223, 369–378), and the pBluescript (Stratagene, La Jolla, Calif., USA) polylinker sequence.

Figure 2:
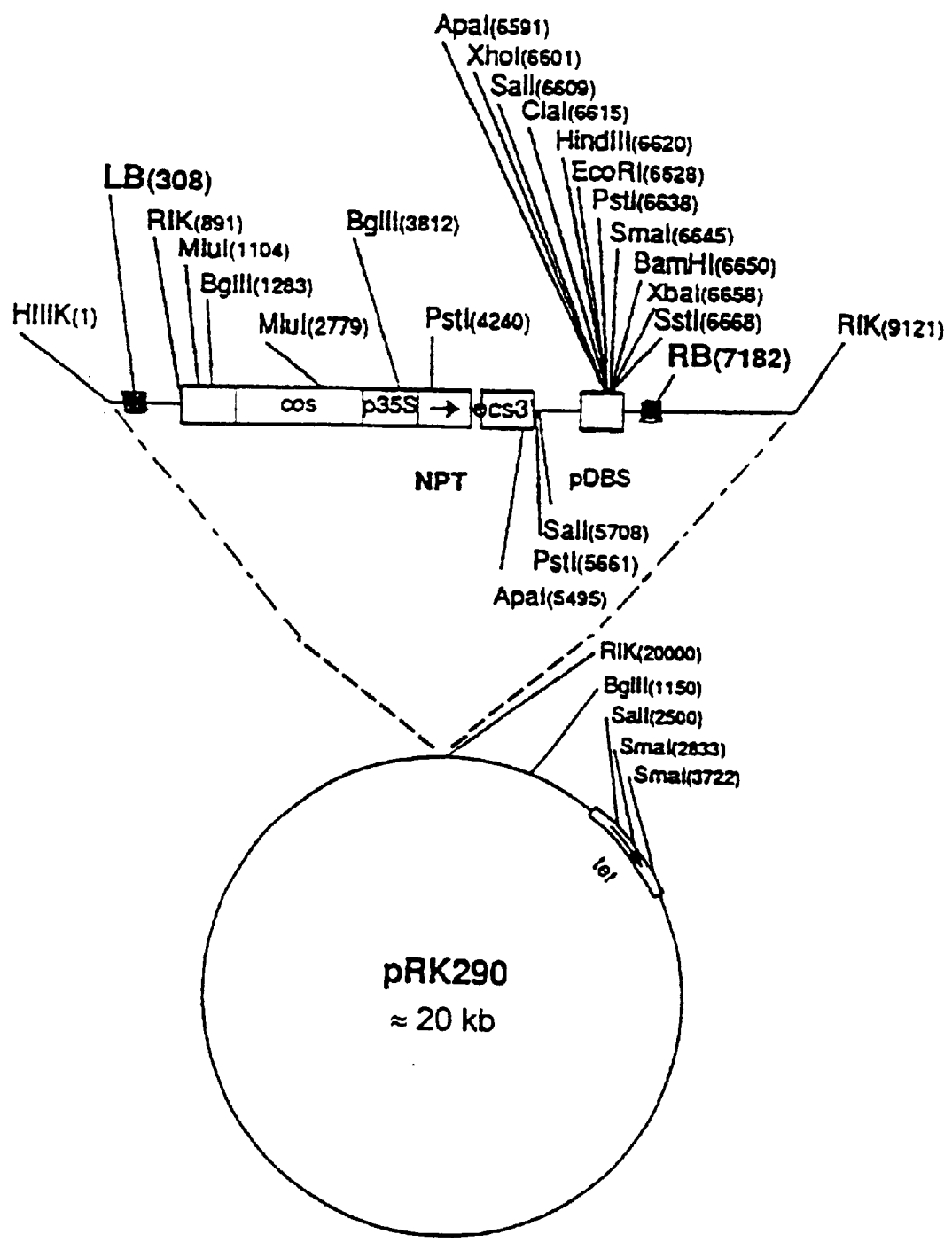
FIG. 2 shows a schematic drawing of the binary cosmid vector pJJ04541 which is used to construct a cosmid library of YAC 1/546. Plasmid pRK290 (20 kb large) (Ditta et al, 1980, Proc. Natl. Acad. Sci. USA, 77, 7347–7351) was used as starting vector. "Tet" refers to the gene conferring resistance to tetracyclin. "LB" signifies T-DNA left border repeat sequence, and "RB" signifies the right border repeat. The cauliflower mosaic virus 35S promoter sequence is indicated by "p35S", and "ocs3'" indicates the octopine synthase 3' end. "NPT" indicates neomycin phosphotransferase, and "cos" refers to the bacteriophage lambda cos site enabling in vitro packaging. "pDBS" indicates the polylinker of pBluescript (Stratagene, La Jolla, Calif., USA).

The size of pJJ04541 amounts 29 kb and is shown schematically in FIG. 2. The cloning capacity of this binary cosmid vector, using phage lambda packaging extracts is within the range of 9 to 24 kb.

Library Construction

Total DNA of the *Saccharomyces cerevisae* strain AB1380 containing YAC 1/1172 and total DNA of the *Saccharomyces cerevisae* strain AB1380 containing YAC 2/1256 was isolated using zymolyase to make protoplasts according to Green and Olsen (Proc Natl Acad Sci USA 87, 1213–1217).

An aliquot of both DNAs was analyzed on PFGE. Both DNA isolates appeared to have a size of >100 kb.

Approximately 15 μg of each DNA was partially digested with Sau3A generating molecules with an average size of 15–25 kb. Subsequently, the samples were centrifugated through a 10–35% sucrose gradient for 22 hours, 22.000 rpm at 20° C. in a Beckman SW41 rotor. 0.5 ml fractions were collected using a needle pierced through the bottom of the centrifuge tube. An aliquot of these fractions was analyzed on a 0.7% agarose gel. The fractions containing DNA molecules with a size of ≈20 kb were pooled and concentrated by ethanol precipitation.

Subsequently, the cohesive ends were partially filled-in with dATP and dGTP using the strategy of partial filling of 5'-extensions of DNA produced by type II restriction endonuclease as described by Korch (Nucleic Acids Res. 15, 3199–3220) and Loftus et al (Biotechniques 12, 172–176).

The binary cosmid vector pJJ04541 was digested completely with XhoI and the linear fragment was partially filled-in with dTTP and dCTP as described by Korch (Nucleic Acids Res. 15, 3199–3220).

The 20-kb fragments were ligated to the cosmid vector and transduced to *E. coli* strain XL1-Blue MR (Stratagene, La Jolla, Calif., USA) using phage lambda Gigapack II XL packaging extracts (Stratagene, La Jolla, Calif., USA) as recommended by the manufacturers. Selection was performed on LB (1% bacto-tryptone, 0.5% bacto-yeast extract and 1% NaCl, pH 7.5) agar plates containing 10 mg/l of tetracyclin. Two banks of approximately 250.000 cosmid clones per bank were made from 2–3 μg of size fractionated yeast DNA of YAC clones 1/1172 and 2/1256 respectively.

Subsequently, these transformants were stored into the wells of microtiter plates (96wells, 100 μl of LB medium containing 10 mg/l of tetracyclin). Replicas of the 96-well grid of cosmid clones in microtiter plates were stamped onto Gene Screen Plus membrane filters (NEN Dupont) and allowed to grow into colonies on media. Colony hybridization, as described by Sambrook et al (in: Molecular cloning: a laboratory manual, 1989, Cold Spring Harbor Laboratory Press), using $^{32}$P-labelled YAC clones 1/1172 and 2/1256 revealed positive cosmids. Of about 10,000 colonies of YAC 111172 approximately 200 positive cosmid clones were identified. Of about 20.000 colonies of YAC 2/1256 300 positive cosmid clones were identified.

Example 6

Fine Mapping of the *Mi* Resistance Gene Segment and Positioning of the AFLP Markers Dividing the Cosmids in Defined Regions In order to divide the cosmids into seven defined regions, the 200 positive cosmid clones of YAC 1/1172 and the 300 positive cosmid clones of YAC 2/1256 were hybridized with 7 of the 8 restriction fragments (YAC fragments) as outlined in Example 4 (see Table 4 and FIG. 1). Positive cosmids for each of the 7 YAC fragments were identified. In addition, cosmids could be identified which reacted positively with the overlapping restriction fragments of the two different YAC clones.

Construction of a Cosmid Contig of the *Mi* Resistance Gene Segment

In order to construct a cosmid contig of all the positive identified cosmids in the various defined regions restriction fragment amplification was used. Approximately 500 ng of each cosmid was used for template preparation and the primers in the amplification of restriction fragments were a EcoRI-primer 5'-GACTGCGTACCAATTC-3' (SEQ ID NO: 11) having no selective nucleotides and a MseI-primer 5'-GATGAGTCCTGAGTAA-3' (SEQ ID NO: 12) having no selective nucleotides according to the method as described in Example 2. The EcoRI-primer was labelled at the 5' end and all the 500 cosmids were amplified using EcoRI/MseI-primer set. The DNA fingerprints contained about 8 to 20 amplified fragments. Sets of cosmids containing amplified fragments of identical size were selected from each region and were rerun on polyacrylamide gels as described in Example 2 until a contiguous array of all the amplified fragments throughout the defined regions could be constructed. In addition, the cosmid contig of one region was aligned with the adjacent regions in order to construct a cosmid contig of the *Mi* locus. In this way a cosmid contig of 96 cosmids was constructed spanning the *Mi* locus of approximately 800 kb.

Detailed Positioning of the *Mi* Linked AFLP Markers on the Cosmid Contig

In order to position the 20 *Mi* linked AFLP markers on the cosmid contig, the 96 cosmids were digested with PstI followed by Southern blot analysis according to Southern, J. Mol. Biol. 98, 503–515.

The AFLP markers were used as hybridization probes as described in Example 4 on the Southern blot of the 96 PstI digests of the cosmids. The exact position of the *Mi* linked AFLP markers, except marker PM02, is outlined in FIG. 3A.

Example 7

Genetic Analysis of *Mi* Mutants

A family of mutant tomato lines was made available through Enza Zaden. These lines were derived from a $F_1$ hybrid heterozygous for the *Mi* resistance gene and heterozygous for the Aps-1 gene (encoding acid phosphatase-1), which is very closely linked to *Mi* (Stevens and Rick, 1986, in. The Tomato Crop, Atherton & Rudich edit., Chapman and Hail, p. 35–109). Different alleles of the Aps-1 gene can be determined by isozyme analysis (Vallejos, 1983, in: Isozymes in plant genetics and breeding, Tanksley and Orton edit., part A, Elsevier, Amsterdam, 469–515) The Aps-1$^1$ allele originates from *L. peruvianum* and has been introgressed into several nematode resistant tomato genotypes by co-segregation with the *Mi* resistance gene. A scheme of these mutant lines is depicted below.

---

$F_1$ - hybrid (heterozygous Aps-1, Mi resistant phenotype)
↓    selfed
$F_2$ - lines (segregating Aps-1 1:2:1, segregating Mi resistance 3:1)
↓    selfing of heterozygous (Aps-1) $F_2$ plants
$F_3$ - lines (segregating Aps-1 1:2:1, segregating Mi resistance 3:1)
↓    selfing of heterozygous (Aps-1) $F_3$ plants
$F_4$ - lines (segregating Aps-1 1:2:1, segregating Mi resistance 3:1)
↓    selfing of heterozygous (Aps-1) $F_4$ plants
$F_5$ - lines (segregating Aps-1 1:2:1, Mi susceptible)
↓    selfing of heterozygous (Aps-1) $F_5$ plants
$F_6$ - lines (segregating Aps-1 1:2:1, Mi susceptible)
↓    selfing of homozygous (Aps-1$^1$) $F_6$ plants
$F_7$ - lines (all Aps-1$^1$, Mi susceptible)
↓    selfing of homozygous (Aps- 1$^1$) $F_7$ plants
$F_8$ - lines (all Aps-1$^1$, Mi susceptible)

---

In the $F_1$, $F_2$, $F_3$ and F4 lines of this family the presence of the Aps-1$^1$ allele correlates with the *Mi* resistant phenotype, whereas absence of the Aps-1$^1$ allele correlates with the *Mi* susceptible phenotype. In the $F_5$ and subsequent progenies this correlation is lost: all plants are susceptible to nematodes regardless of the Aps-1alleles.

Figure 3B:
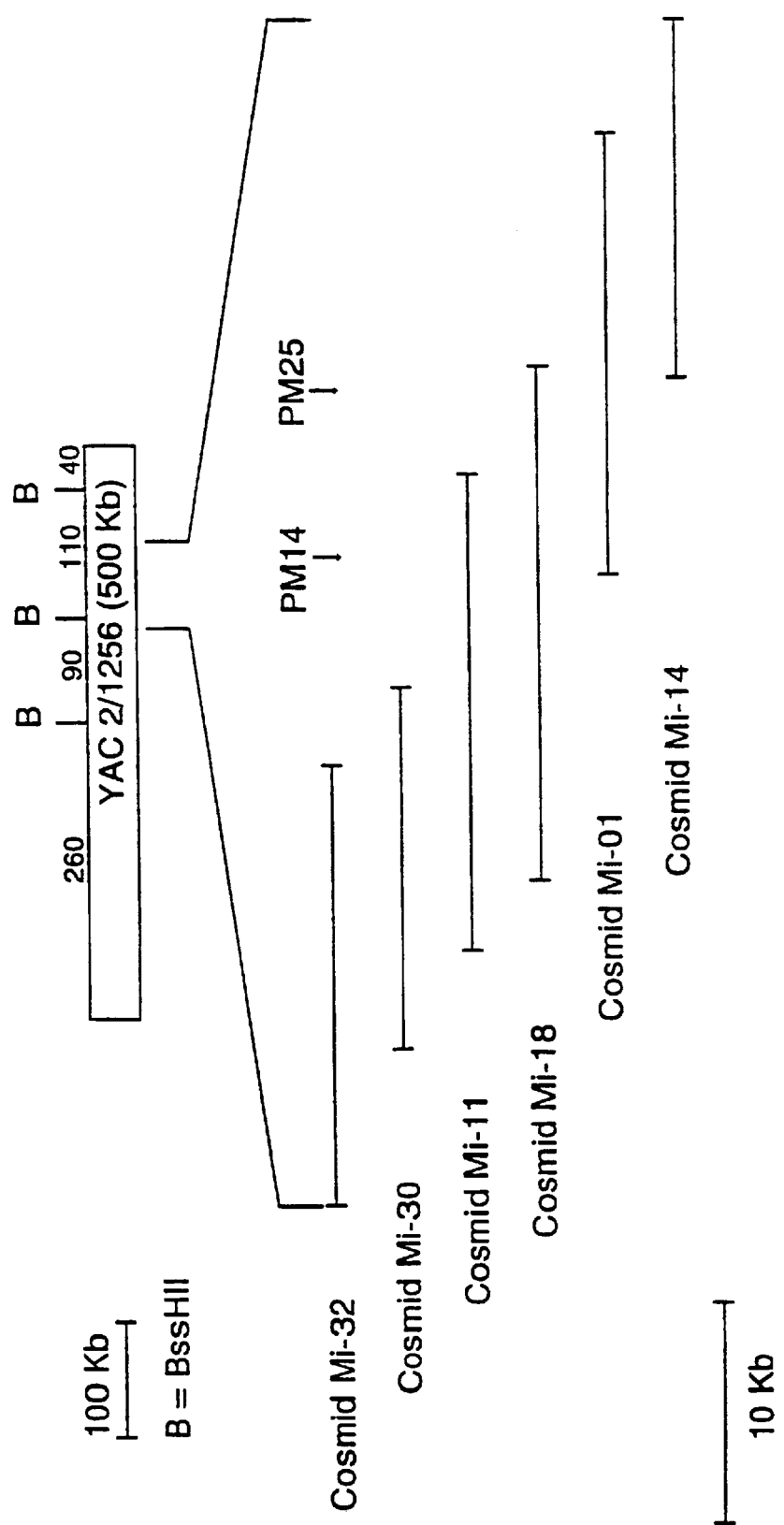
FIG. 3B shows a schematic representation of the cosmid contig of the region comprising the *Mi* resistance gene. The cosmids *Mi*-32, *Mi*-30, *Mi*-11, *Mi*-18, *Mi*-01 and *Mi*-14 are represented by horizontal lines. The location of the AFLP markers PM14 and PM25 is indicated.

Twenty individuals from each $F_2$, $F_3$, $F_4$, $F_5$, $F_6$, $F_7$ and $F_8$ generation were tested for nematode resistance, for presence of the Aps-1 allele and presence of the *Mi* linked AFLP markers. Nematode testing of seedlings was performed in soil contaminated with root galls of *M. incognita*. The nematode resistance results were as indicated in the above scheme: 3:1 segregation in $F_2$, $F_3$ and F4 plants and susceptibility in $F_5$ and progeny populations. Most of the *Mi* linked AFLP markers indicated an identical *Mi* genotype as the Aps-1 isozyme marker. However, 3 of the AFLP markers PM14, PM16 and PM25 appeared to segregate with the *Mi* phenotype: In most $F_5$, $F_6$, $F_7$ and $F_8$ plants the *Mi* susceptibility was indicated by the adsence of these markers. The AFLP markers PM14, PM16 and PM25 showed a correlation between the AFLP *Mi* genotype and *Mi* phenotype in the mutants. Markers PM14 and PM25 are adjacent on the physical map as shown in FIG. 3B, and therefore, it was postulated that the region surrounding these AFLP markers was a good candidate to comprise the *Mi* resistance gene.

Example 8

Physical map of the overlapping Cosmid Clanes Comprising the *Mi* Resistance Gene The identification of cosmids hybridizing with the *Mi* linked AFLP markers PM14 and PM25 was performed in Example 6. PM14 identifies cosmids *Mi*-11, *Mi*-18 and *Mi*-01 whereas PM25 identifies cosmids *Mi*-18 and *Mi*-01.

Figure 4:
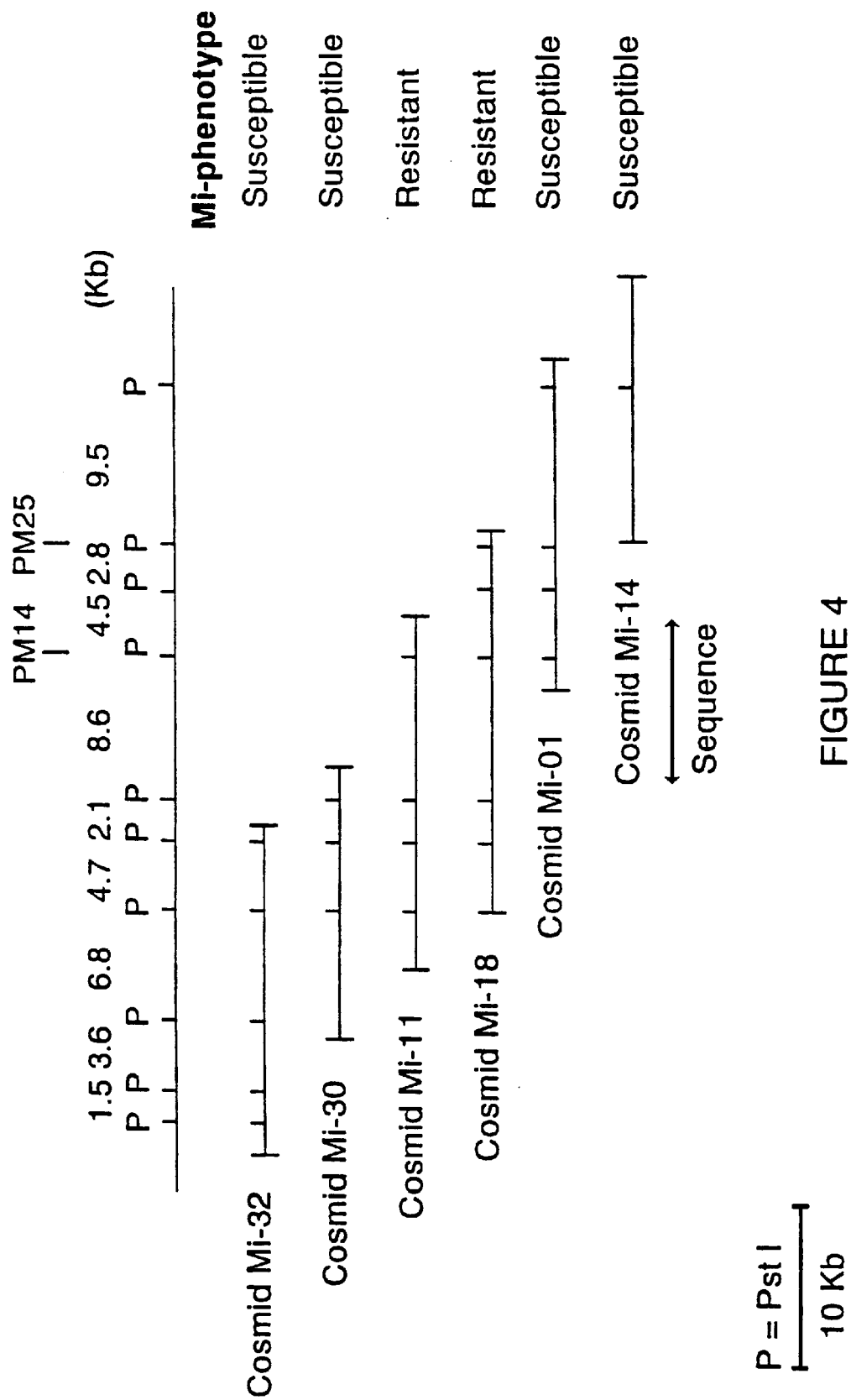
FIG. 4 shows a physical fine map of the cosmids *Mi*-32, *Mi*-30, *Mi*-11, *Mi*-18, *Mi*-01 and *Mi*-14 for the restriction enzyme PstI. The size of the PstI fragments is indicated (in kb). The *Mi* phenotype, as identified in an in vitro disease assay, of the $R_0$ plants comprising the various cosmids is indicated in the right end part of the figure. The DNA segment of which the nucleotide sequence was determined is indicated by a double line with a bidirectional arrow.

Subsequently, a small cosmid array around cosmids *Mi*-11, *Mi*-18 and *Mi*-01 was selected from the cosmid contig described in Example 6. A contig of 6 cosmids comprising the 3 identified cosmids and the adjacent cosmids, was selected. These 6 cosmids are *Mi*-32, *Mi*-30, *Mi*-11, *Mi*-18, *Mi*-01 and *Mi*-14. In order to make a physical fine map of these 6 cosmids, the DNA samples of the cosmid contig were digested with PstI followed by electrophoresis on a 0.8%-agarose gel. The physical overlap between the various cosmids could be determined. Combining these data with the data obtained about the detailed positioning of the *Mi* linked AFLP markers on the cosmid contig (see Example 6) a physical fine map with the location of PM14 and PM25 could be constructed as shown in FIG. 4. The cosmid contig around the AFLP markers PM14 and PM25 was calculated to be approximately 50 kb.

Example 9

Transformation

Transfer of Cosmids to *Agrobacterium Tumefaciens*

The cosmid clones *Mi*-32, *Mi*-30, *Mi*-11, *Mi*-i 8, *Mi*-01, *Mi*-14 and the control cosmid pJJ04541 were introduced in *Agrobacterium tumefaciens* through conjugative transfer in a tri-parental mating with helper strain HB101 (pRK2013) essentially according to Deblaere et al (Methods in Enzymology 153, 277–292). *E. coli* were grown in LB medium (1% bacto-tryptone, 0.5% bacto-yeast extract and 1% NaCl, pH 7.5) supplemented with 5 mg/l tetracyclin at 37° C. The helper strain HB101 (pRK2013) was grown under identical conditions in LB medium supplemented with 100 mg/l kanamycin sulphate.

*Agrobacterium tumefaciens* strain AGL1 (Lazo et al, Bio/Technology, 9, 963–971, 1991) was grown in LB medium supplemented with 100 mg/l carbenicillin at 28° C. Overnight cultures were diluted 1:100 in LB medium without any antibiotics and after 6 hours of growth, 0.1 ml each of the *Agrobacterium culture*, the helper strain culture and a cosmid strain culture were mixed and plated on LB agar plates without antibiotics. After overnight incubation at 28° C., the mixture was plated on LB medium agar plates containing 100 mg/l carbenicillin and 10 mg/l tetracyclin to screen for transconjugants. Plates were incubated for 34 days at 28° C. Two serial passages through selective agar plates were performed to select for single transconjugant *Agrobacterium colonies*.

Characterization of *A. tumefaciens* Transconjugants

Small-scale cultures were grown from selected colonies and grown in LB medium containing 10 mg/l tetracyclin. Plasmid DNA was isolated by alkaline lysis using the method as described by Ish-Horowicz et al (Nucl. Acids Res. 9, 2989–2997, 1981), and digested with BglII using standard techniques. In addition, restriction fragment amplification on miniprep DNA of *A. tumefaciens* was performed using the enzyme combination EcoRI/MseI and primers having no selective nucleotide as described in Example 6. Subsequently, the BglII restriction enzyme pattern as well as the DNA fingerprint of the *A. tumefaciens* transconjugant were compared with those of miniprep DNA of the *E. coli* strain containing the cosmid. Only those *A. Tumefaciens* transconjugants harbouring a cosmid with the same DNA pattern as the corresponding *E. coli* culture were used to transform a susceptible tomato line.

Transformation of a Susceptible Tomato Line

Seeds of the susceptible tomato line 52201 (Rijk Zwaan, De Lier, The Netherlands) were surface-sterilized in 2% sodium hypochlorite for 10 minutes, rinsed three times in sterile distilled water, and placed on germination medium (consisting of half-strength MS medium according to Murashige and Skoog, Physiol. Plant. 15, 473–497, with 1% (w/v) sucrose and 0.8% agar) in glass jars or polypropylene culture vessels. They were left to germinate for 8 days.

Culture conditions were 25° C., a photon flux density of 30 $\mu mol.m^{-2}S^{-1}$ and a photoperiod of 16/24 h.

Transformation of tomato was performed according to Koornneef et al (1986), In: Tomato Biotechnology, 169–178, Alan R. Liss, Inc., and is described briefly below. Eight day old cotyledon explants were precultured for 24 hours in Petri dishes containing a feeder layer of *Petunia hybrida* suspension cells plated on MS20 medium (culture medium according to Murashige and Skoog, (1962) Physiol. Plant. 15, 473–497 with 2% (w/v) sucrose and 0.8% agar) supplemented with 10.7 $\mu$M α-naphthaleneacetic acid and 4.4 $\mu$M 6-benzylaminopurine. The explants were then infected with the diluted overnight culture of *Agrobactehum tumefaciens* containing the cosmid clones *Mi*-32, *Mi*-30, *Mi*-11, *Mi*-18, *Mi*-01 and *Mi*-14 or the cosmid vector pJJ04541 for 5–10 minutes, blotted dry on sterile filter paper and cocultured for 48 hours on the original feeder layer plates. Culture conditions were as described above. Overnight cultures of *Agrobacterium tumefaciens* were diluted in liquid MS20 medium (medium according to Murashige and Skoog (1962) with 2% (w/v) sucrose, pH 5.7) to an $O.D._{.600}$ of 0.8.

Following the cocultivation, the cotyledon explants were transferred to Petri dishes with selective medium consisting of MS20 supplemented with 4.56 $\mu$M zeatin, 67.3 $\mu$M vancomycin, 418.9 $\mu$M cefotaxime and 171.6 $\mu$M kanamycin sulphate, and cultured under the culture conditions described above. The explants were subcultured every 3 weeks onto fresh medium. Emerging shoots were dissected from the underlying callus and transferred to glass jars with selective medium without zeatin to form roots. The formation of roots in a medium containing kanamycin sulphate was regarded as an indication of the transgenic nature of the shoot in question. Truly transgenic regenerants were propagated in vitro by subculturing the apical meristem and auxiliary buds into glass jars with fresh selective medium without zeatin.

Example 10

Complementation Analysis
Identification of Cosmids with the *Mi* Resistance Gene by Screening for Resistance in Roots of Transformed Plants Roots of in vitro grown transformed $R_0$ plants have been subjected to the disease assay as described in Example 1. From each transformant two root explants have been assayed. In total 72 $R_0$ plants of 7 different cosmid transformations have been tested; 6 cosmids carrying tomato insert DNA and one cosmid, pJJ04541, is without tomato insert DNA. The results are shown in Table 1. Sixty three transgenic $R_0$ plants appeared susceptible because galls had been formed on at least one of the two root cultures. Nine $R_0$ plants scored resistant, because no galls could be found on the root cultures. Seven resistant plants had been derived from transformation with cosmid *Mi*-11, while two resistant plants had been derived with cosmid *Mi*-18, that is overlapping for a great part with cosmid *Mi*-11. The cosmids *Mi*-11 and *Mi*-18 were used for further molecular analysis.

TABLE 1

| | $R_0$ plants | |
|---|---|---|
| Cosmid | Resistant | Susceptible |
| Mi-32 | 0 | 8 |
| Mi-30 | 0 | 11 |
| Mi-11 | 7 | 4 |
| Mi-18 | 2 | 8 |

TABLE 1-continued

| | $R_0$ plants | |
|---|---|---|
| Cosmid | Resistant | Susceptible |
| Mi-01 | 0 | 10 |
| Mi-14 | 0 | 15 |
| pJJ04541 | 0 | 7 |

Molecular Analysis of the Transformed Plants with a Resistant Phenotype

To demonstrate that the resistant phenotype of transgenic $R_0$ plants, which had been with the overlapping cosmids *Mi*-11 and *Mi*-18, is determined by the genomic insert present in the various cosmids, an AFLP analysis with the AFLP marker PM14 was performed. Selective restriction fragment amplification was performed with the primer combination identifying marker PM14 for the $R_0$ plants transformed with cosmids *Mi*-11 and *Mi*-18. The DNA fingerprints obtained showed the presence of the marker PM14 in the resistant plants indicating that the genomic insert present in cosmids *Mi*-11 and *Mi*-18 is also present in the $R_0$ plants and that the two identified overlapping cosmids *Mi*-11 and *Mi*-18 comprise the *Mi* resistance gene.

The inserts in cosmids *Mi*-11 and *Mi*-18 and the inserts in the adjacent cosmids *Mi*-32, *Mi*-30 on one side and cosmids *Mi*-01 and *Mi*-14 on the other side, were further characterized. The DNA region comprising the *Mi* resistance gene based on the overlap between the cosmids *Mi*-11 and *Mi*-18, was estimated at approximately 16–18 kb. Based on the susceptibility of the $R_0$ plants having the insert present in cosmid *Mi*-30, this region could be narrowed down to approximately 12 kb. A DNA segment comprising the *Mi* resistance gene, corresponding to the region flanked by the right ends of cosmids *Mi*-30 and *Mi*-11, was sequenced (see FIG. 4).

Example 11

Nucleotide Sequence and Deduced Amino Acid Sequence of the *Mi* Resistance Gene From Tomato
Subcloning of the overlapping DNA segment To determine the sequence of the overlapping DNA segment in cosmids *Mi*-11 and Mi-18 containing the *Mi* resistance gene, a set of random subclones with a insert size of approximately 2 kb were generated. 7.5 $\mu$g of CsCl purifid DNA of cosmids *Mi*-11 and *Mi*-18 was sheared for 10 seconds at 4° C. at 15% probe power (in 40 $\mu$l 10mM Tris-acetate, 10mM Mg-acetate and 50mM K-acetate) using a Misonix (Misonix Inc., Farmingdale, N.Y., USA) sonicator (type XL2020) with a water filled cup horn (type 431A). Subsequently, the DNA was heated for 10 minutes at 60° C. and cooled to room temperature. The ends of the DNA fragments were repaired by adding 10 $\mu$l of a repair mixture (10mM Tris-acetate, 10mM Mg-acetate, 50 mM K-acetate, 10U Klenow DNA polymerase, 10U $T_4$DNA polymerase and 2 mM of all 4 dNTP's) and followed by incubation for 30 minutes at 20° C. The sheared DNA was separated by electrophoresis on 1% Seakem GTG agarose gel (FMC Bio Products, Rockland, Me., USA). The fraction with a size of 1.8–2.2 kb was excised from the gel and subsequently the gel slice was digested with β-agarase I according to the protocol of the manufacturer (New England Biolabs Inc, Beverly, Mass., USA) and the DNA was precipitated.

A modified pUC19 vector (designated pStuc) was used to clone the 1.8–2.2 kb fraction. In this vector the BamHI/SalI fragment of pUC19 was replaced by a DNA fragment containing a StuI, SpeI and SalI restriction site using two oligonucleotide primers and standard cloning techniques as described by Sambrook et al. (in: Molecular cloning a laboratory manual, 1989, Cold Spring Harbor Laboratory Press). The 1.8–2.2 kb fraction was ligated at 16° C. in the a StuI digested and dephosphorylated pStuc vector. The ligation mixture was subsequently transformed to Epicurian Coli XL2-Blue MRF' ultracompetent cells (Stratagene, La Jolla, Calif., USA). Individual colonies were grown and stored in 384-wells microtiter plates (100 µl of LB medium containing 100 mg/l of carbenicillin).

To isolate clones representing the overlapping DNA region in cosmids $Mi$-11 and $Mi$-18 containing the $Mi$ resistance gene, the 8.6 and 4.5 kb PstI fragment of cosmid clone $Mi$-18 (see FIG. 4) as well as the AFLP marker PM14 were used as hybridization probes in colony hybridizations. Therefore, replicas of the 384-well grid of clones in microtiter plates were stamped onto Gene Screen Plus membrane filters (DuPont NEN, Boston, Mass., USA) and allowed to grow into colonies on media. Eighty four positive clones were used to isolate plasmid DNA using the alkaline lysis method as described by Ish-Horowicz et al. 1981, Nucl. Acids Res. 9, 2989–2997.

Sequence Analysis

The ABI PRISM dye ternminator cycle sequencing ready reaction kit was used to perform sequencing reactions in a Gene-Amp PCR system Model 9600 (Perkin-Elmer, Foster City, Calif. USA). Standard M13 forward and reverse primers were used. The reaction products were analyzed on 48 cm gels of an ABI Prism 377. The DNA sequence of 84 selected clones was determined using the standard forward and reverse sequencing primers. Sequence assembly and analysis was done with the 1994 version of the STADEN sequence analysis program (Dear and Staden, 1991, Nucl. Acids Res. 19, 3907–3911). A contiguous DNA sequence of approximately 9.9 kb nucleotides could be formed and is shown in FIG. 5. A large open reading frame of 3621 nucleotides (ORF2) encoding a truncated polypeptide of 1206 amino acids (FIG. 7B) could be deduced.

Example 12

Root-knot Nematode Infection: Soil Inoculation

Soil infected with the root-knot nematode *Meloidogyne incognita* had been prepared as follows root systems of heavily infected tomato plants with a high number of galls (or root-knots), were cut into pieces and mixed through fresh soil.

Seeds were sown or small rooted plantlets were transferred into the infected soil. The plants were grown in a greenhouse at a temperature of 25° C. After 4 to 8 weeks, the plants were carefully pulled out of the soil and the roots were rinsed in water in order to remove the adhering soil. The level of infection was determined by counting the number of galls formed.

Plants were considered to be resistant when three galls or less were visible on the roots. Plants were considered susceptible when more than three galls were formed on the root system.

Example 13

Complementation Analysis

Identification of cosmids with the $Mi$ resistance gene by screening for resistance in the selfed progenies of transformed plants The primary regenerants ($R_0$ generation) of the transformation experiments were grown in the greenhouse for seed set. For each cosmid, ten to fifteen regenerants were grown and $R_1$ seeds were harvested. $R_1$ lines of at least seven $R_0$ plants of each cosmid were tested for resistance against *Meloidogyne incognita* in order to identify cosmids with the resistance gene. Twenty to 30 seedlings or plantlets of each $R_1$ line were inoculated and evaluated as described in Example 12.

In total 63 $R_1$ lines of 7 different cosmid transformations have been tested; 6 cosmids carrying tomato insert DNA and one cosmid, pJJ04541, without tomato insert DNA. The results are shown in Table 2. Fifty-four transgenic $R_0$ plants appeared to be susceptible, because galls had been formed on the root systems of all tested Re-plants. Nine $R_0$ plants are considered resistant, because at least half of the plants of each $R_1$ line had three or less galls. One $R_1$ line was completely resistant, six $R_1$ lines segregated in a ratio of about 3:1 (resistant to susceptible plantlets), and the progenies of two $R_0$ plants segregated 1:1. All the nine resistant $R_0$ plants had been derived from transformations with cosmid $Mi$-11.

Additional genetic evidence for the presence of the $Mi$ resistance gene on cosmid $Mi$-11 was obtained in the next generation. Resistant $R_1$ plants were selfed. Fourteen of the resulting $R_2$ lines, which originated from four different $R_0$ plants, were tested for resistance against *M. incognita*. Twenty to thirty seedlings of each $R_2$ line were inoculated and evaluated as described in Example 12. The results are shown in Table 3. Five $R_2$ lines were completely resistant, indicating that the parental $R_1$ plants were homozygous for the $Mi$ resistance gene. Eight $R_2$ lines segregated in a ratio of 3.1, indicating that their parental $R_1$ plants were heterozygous for the $Mi$ resistance gene. One $R_2$ line was segregating in a ratio of about 1:1, and none of the tested lines appeared to be completely susceptible. These results prove that the selected $R_1$ plants, which are derived from several plants transformed with cosmid $Mi$-11, contain the functional $Mi$ resistance gene.

TABLE 2

Number of $R_1$-lines of independent $R_0$ plants tested

| Cosmid | Total | Segregation ratio R:S (resistant to susceptible) | | | |
|---|---|---|---|---|---|
| | | 1:0 | 3:1 | 1:1 | 0:1 |
| Mi-32 | 7 | 0 | 0 | 0 | 7 |
| Mi-30 | 9 | 0 | 0 | 0 | 9 |
| Mi-11 | 9 | 1 | 6 | 2 | 0 |
| Mi-18 | 8 | 0 | 0 | 0 | 8 |
| Mi-01 | 10 | 0 | 0 | 0 | 10 |
| Mi-14 | 9 | 0 | 0 | 0 | 9 |
| pKK04541 | 11 | 0 | 0 | 0 | 11 |

TABLE 3

Number of $R_2$-lines of independent $R_1$ plants tested

| Cosmid | Total | Segregation ration R:S (resistant to susceptible) | | | |
|---|---|---|---|---|---|
| | | 1:0 | 3:1 | 1:1 | 0:1 |
| Mi-11 | 14 | 5 | 8 | 1 | 0 |

Example 14

Potato Aphid Infection Assay

Small tomato plants (4 weeks old) were inoculated with the potato aphid (*Macrosiphum euphorbiae*) by placing five to eight female aphids on the leaves. The plants were grown in the greenhouse at a temperature of 18° to 20° C. After one to two weeks the level of resistance was determined by counting the number of newly born aphids.

Plants were considered to be resistant when no living aphids were present on the stem or leaves plants were susceptible when newly born aphids were present.

Example 15

Complementation Analysis

Identification of cosmids with the *Meu*-1 resistance gene by screening for resistance in the selfed progenies of transformed plants.

A subset of the $R_1$ lines obtained in Example 13 was tested for resistance against *Macrosiphum euphorbiae* in order to identify cosmids with the *Meu*-1 resistance gene. Ten to fifteen plantlets of each $R_1$ line were inoculated and evaluated as described in Example 14. In total 41 $R_1$ lines of 7 different cosmid transformations have been tested: 6 cosmids carrying tomato insert DNA and one cosmid, pJJ04541, without tomato insert DNA. The results are shown in Table 4. Thirty-six transgenic $R_0$ plants are considered susceptible, because dozens of aphids were proliferating on all or most plants of each $R_1$ line. Five $R_0$ plants are resistant, because at least half of the plants of each $R_1$ line were without living aphids. All these five resistant $R_0$ plants had been transformed with cosmid *Mi*-11.

The obtained results strongly indicate that the $R_0$ plants which are derived from transformations with cosmid *Mi*-11, contain a functional *Meu*-1 resistance gene.

TABLE 4

Number of $R_1$-lines of independent $R_0$ plants tested

| Cosmid | Total | Segregation ratio R:S (resistant to susceptible) | | | |
|---|---|---|---|---|---|
| | | 1:0 | 3:1 | 1:1 | 0:1 |
| Mi-32 | 4 | 0 | 0 | 0 | 4 |
| Mi-30 | 7 | 0 | 0 | 0 | 7 |
| Mi-11 | 7 | 1 | 2 | 2 | 2 |
| Mi-18 | 7 | 0 | 0 | 0 | 7 |
| Mi-01 | 6 | 0 | 0 | 0 | 6 |
| Mi-14 | 5 | 0 | 0 | 0 | 5 |
| pJJ04541 | 5 | 0 | 0 | 0 | 5 |

Additional genetic evidence for the presence of the *Meu*-1 resistance gene on cosmid *Mi*-11 was obtained in the next generation. Twenty-four $R_2$ lines that had been obtained from selfings of nematode resistant $R_1$ plants (see Example 13), which originated from nine different $R_0$ plants, were tested for resistance against *M. euphorbiae*. Eleven to fifteen seedlings of each $R_2$ line were inoculated and evaluated as described in Example 14. The results are shown in Table 5. One $R_2$ line segregated in a ratio of 3:1 and eight $R_2$ lines were segregating in a ratio of about 1:1. In these nine lines the potato aphid resistance phenotype is clearly visible. Five $R_2$ lines appeared to be completely susceptible. The remaining ten $R_2$ lines scored intermediate: they segregated in a ratio of about 1:3. These results indicate that several $R_1$ plants, which are resistant to *Meloidogyne incognita* and which are derived from $R_0$ plants transformed with cosmid *Mi*-11, have a functional *Meu*-1 resistance gene.

In addition, eight $R_1$BC lines that were obtained from nematode resistant $R_1$ plants backcrossed with susceptible tomato line 52201 were tested for resistance against *M. euphorbiae*, in order to confirm inheritance of the introgressed *Meu*-1 resistance gene. Twelve to fifteen seedlings of each $R_1$BC line were inoculated and evaluated as described in Example 14. The results are shown in Table 6.

The segregation ratios shown in Table 5 and Table 6 only serve to illustrate the inheritance of the resistance phenotype.

TABLE 5

Number of $R_2$-lines of independent $R_1$ plants tested

| Cosmid | Total | Segregation ratio R:S (resistant and susceptible) | | | | |
|---|---|---|---|---|---|---|
| | | 1:0 | 3:1 | 1:1 | 1:3 | 0:1 |
| Mi-11 | 24 | 0 | 1 | 8 | 10 | 5 |

TABLE 6

Number of $R_1$BC-lines of independent $R_1$ plants tested

| Cosmid | Total | 1:0 | 3:1 | 1:1 | 1:3 | 0:1 |
|---|---|---|---|---|---|---|
| Mi-11 | 8 | 0 | 1 | 5 | 2 | 0 |

Example 16

Transcript Mapping

Transcript mapping studies were performed to map the 5' and 3' end of the *Mi*-resistance gene and to determine whether the *Mi* resistance gene contains any introns. The polymerase chain reaction to amplify parts of the transcripts from the *Mi* resistance gene was used for this purpose.

Total RNA from leaf tissue of the resistant tomato cultivar E22 was isolated according to the hot phenol method as described by Sambrook et al (in: Molecular cloning: a laboratory manual, 1989, Cold Spring Harbor Laboratory Press) Poly A+RNA was isolated using biotinylated oligo (dT) bound to Dynabeads M-280 Streptavidin (DYNAL A.S., Oslo, Norway) according to the instructions of the manufacturer. A cDNA library was constructed using the Superscript Rnase H Reverse Transcriptase cDNA kit from Life technologies, Inc. Gaithersburg, Md., USA and the protocol supplied by the manufacturer. 5' and 3' RACE products were obtained using the Marathon cDNA amplification kit from Clontech (Paolo Alto, Calif., USA). The primers used were designed based on the genomic *Mi*-sequence, and especially on the 5' end of the coding sequence of ORF2. Subsequently, the various 5' and 3'-RACE fragments were cloned into the TA cloning vector pCRII (Invitrogen Corporation, San Diego, Calif., USA) and sequenced using standard protocols. The nucleotide sequences obtained were aligned with the 9.9 kb genomic sequence and two intron sequences could be deduced for the 5' end of the *Mi* resistance gene. One intron of 1306 nucleotides was located from nucleotide position 1936 to 3241 and the second one from nucleotide position 3305 to 3379 (FIG. 5).

The largest *Mi*-transcript detected with the Marathon cDNA amplification kit maps at nucleotide position 1880. Hence, we conclude that the *Mi* transcriptional initiation site is positioned at or upstream of nucleotide 1880. The first ATG codon that could be detected within the 5' cDNA was located at nucleotide position 3263, 52 nucleotides upstream of the second intron, and a large open reading frame (ORF1)

encoding a polypeptide of 1257 amino acids could be deduced and is shown in FIG. 7A. As a result, this second intron is located between amino acid 14 and 15 of the Mi-resistance gene product.

Example 17

PCR Analysis of MI-11 and MI-18 Transformed Plants

Data obtained from complementation analysis in roots of transformed plants (Example 10) indicated that the Mi resistance gene was located on a DNA segment overlapping between cosmids Mi-11 and Mi-18, excluding the DNA segment corresponding to cosmid Mi-30, transformants of which were all susceptible. This region was estimated to be about 12 kb. However, in complementation analysis on the selved progenies of transformed plants, only cosmid Mi-11 transformed plants scored resistant (Examples 13 and 15). To address the question why Mi-18 transformed plants scored susceptible, a PCR analysis on the presence or absence of the putative Mi-ORF in transformed Mi-11 and Mi-18 plants was performed.

The following DNA samples have been analysed:
1. YAC clone 2/1256.
2–3. Cosmid Mi-11 in E. coli and in A. tumefaciens, respectively.
4–5. Cosmid Mi-18 in E. coli and in A. tumefaciens, respectively.
6. Tomato line E22 (resistant).
7. Tomato line 52201 (susceptible).
8–12. Five plants transformed with cosmid Mi-11.
13–17. Five plants transformed with cosmid Mi-18.

The DNA was digested with PstI and PstI-adaptors were ligated. Subsequently, a PCR analysis was performed with a primer identifying the PstI site and three additional selective nucleotides or marker PM14 and various PCR primers located upstream of PM14 using the enzym rTh polymerase (Gene Amp XL PCR kit; Perkin Elmer). The products generated varied in size from 443 to 6110 bp and encompass the complete PM14 upstream region of the putative Mi-ORF (see FIG. 6).

It appeared that all templates generated PCR products of the expected size with the exception of the five plants transformed with cosmid Mi-18. Only the smallest PCR product (443 bp) was formed. These data indicate that almost the complete PM14 upstream region was not present in plants transformed with cosmid Mi-18. These deletions do not occur with cosmid Mi-18 present in E. coli or A. tumefaciens but occur only in transformed plants. Hence, we conclude that these deletions are responsible for the susceptible phenotype to Meloidogyne incognita and/or Macrosiphum euphorbiae of Mi-18 transformed plants.

Example 18

Nucleotide Sequence of Cosmid MI-11

The observation that only plants transformed with cosmid Mi-11 showed a resistant phenotype might indicate that additional open reading frames present on Mi-11 could be candidates to encode for resistance against nematodes and/or aphids. Therefore, the nucleotide sequence of the region upstream of the postulated ORF1 was determined to identify additional open reading frames.

A set of random subclones with an insert size of 2 kb were isolated using the 2.1, 4.7 and 2.9 kb PstI fragment of cosmid clone Mi-11 as hybridization probes in colony hybridization essentially as described in Example 11.

Fourty nine positive clones were used to determine the DNA sequence using the standard forward and reverse sequencing primers. Sequence assembly and analysis was performed as described in Example 11.

Three contiguous DNA stretches with sizes of 5618 bp (con25), 898 bp (con10) and 2495 bp (con62) could be deduced. The gaps between these DNA stretches and the 9870 bp DNA sequence containing the putative Mi-ORF (FIG. 6) was calculated using PCR and varied between 50–200 bp.

The three determined contigs (con25, con10 and con62) were analysed for the distribution of stop coctons in all six possible frames. No significant ORF frames with a size of or superior to 120 amino acids could be postulated. In addition, no DNA homology with the putative ORF1 was detected. Hence, the only significant ORF present on cosmid Mi-11 was ORF1 as described in FIG. 5. Based on these results, it can be concluded that the polynucleotide encoded by ORF1 confers resistance to nematodes as well as to aphids and, hence, that the Mi-resistance gene and the Meu-1 resistance gene are referring to the same coding sequence as depicted in FIG. 5.

Example 19

Transformation of Tobacco and Complementation Analyses

Transformation of Tobacco

The tobacco cultivar Petit Havana, type SR1, was transformed with cosmid Mi-11 or the cosmid vector pJJ04541 using the protocol as described by Horsch et al. (Science 227, 1229–1231, 1985).

Complementation Analysis: Screening for Nematode Resistance in Root Cultures of Transformed Tobacco Plants Roots of in vitro grown transformed $R_0$ plants of tobacco have been subjected to the disease assay as described in Example 1. From each of the 31 transformants two or more root explants have been assayed. In addition, all 17 Mi-11 transformants have been analyzed by PCR for the presence of the putative Mi ORF1 by screening for an internal fragment with a size of 823 base pairs (ranging from nucleotide position 4824 to 5646, see FIG. 5). Simple PCR primers for the fragment were deduced from the sequence as shown in FIG. 5. The primers used have the following sequences:

primer S21: 5'CCAAGGACAGAGGTCTAATCG-3' (SEQ ID NO: 13)
primer S22: 5'TTGAGGTGATGTGGTAAATGG-3' (SEQ ID NO: 14).

Primer S21 targets the sequence from nucleotide position 4824 to 4844 and primer S22 targets the sequence from nucleotide position 5626 to 5646 (see FIG. 5).

The results of the in vitro disease assay and of the PCR analysis (presence "+" or absence "−" of the internal PCR fragment) are shown in Table 7. "Mi-11" represents transformed plants comprising the putative Mi ORF1 and "Mi-11Δ" represents those transformed plants having a deletion in the putative Mi ORF1, as determined by the PCR analysis (described above). Twenty-nine $R_0$ transformants were susceptible, because galls had been formed on at least one of the tested root cultures. Generally, the rate of gall formation on tobacco roots is slightly lower than on susceptible tomato roots. Two $R_0$ plants scored resistant to Meloidogyne incognita, because no galls could be found on the root cultures. Both resistant plants were transformed with cosmid Mi-11 comprising the internal PCR fragment indicating the presence of the Mi resistance gene.

TABLE 7

| Genotype | PCR fragment | $R_0$ plants Resistant | Susceptible |
|---|---|---|---|
| Mi-11 | + | 2 | 7 |
| Mi-11Δ | − | 0 | 8 |
| pJJ04541 | − | 0 | 14 |

Complementation Analysis: Screening for Aphid Resistance in Cuttings of Transformed Tobacco Plants Rooted cuttings of transformed $R_0$ plants of tobacco were inoculated and evaluated as described in Example 14. From each of the 23 transformants two or three cuttings have been assayed for resistance against *Macrosiphum euphorbiae*. The results of the infection assay and the PCR analysis (as described above) are shown in Table 8. Twenty-one $R_0$ plants are considered susceptible, because several living aphids were counted on at least one of the tested cuttings. In general, the level of proliferation of the aphids on tobacco is low compared with the proliferation on susceptible tomato plants. Two $R_0$ plants scored resistant, because all cuttings of these plants were without living aphids. The aphid resistant plants were transformed with cosmid Mi-11, comprising the Mi resistance gene, as indicated by the presence of the internal PCR fragment.

TABLE 8

| Genotype | PCR fragment | $R_0$ plants Resistant | Susceptible |
|---|---|---|---|
| Mi-11 | + | 2 | 3 |
| Mi-11Δ | − | 0 | 6 |
| pJJ04541 | − | 0 | 12 |

Example 20

Transformation of Potato and Complementation Analyses

Transformation of Potato

The potato variety Diamant (Cebeco Zaden B.V., Vlijmen, The Netherlands) was used for transformation. Internode explants of in vitro grown plants were transformed with cosmid Mi-11 or the cosmid vector pJJ04541 using the protocol as described by Ooms et al. (Theor. Appl. Genet. 73, 744–750).

Complementation Analysis: Screening for Nematode Resistance in Root Cultures of Transformed Plants Roots of in vitro grown transformed $R_0$ plants of potato have been subjected to the disease assay as described in Example 1. From each of the 31 transformants at least two root explants have been assayed. In addition, all 26 Mi-11 transformants have been analyzed by PCR using primers S21 and S22 as described in Example 19. The results of the in vitro disease assay and of the PCR analysis (presence "+" or absence "−" of the internal PCR fragment) are shown in Table 9. "Mi-11" represents transformed plants comprising the putative Mi ORF1 and "Mi-11Δ" represents those transformed plants having a deletion in the putative Mi ORF1, as determined by the PCR analysis (described above). Twenty-eight $R_0$ transformants were susceptible, because galls had been formed on at least one of the root cultures. Generally, the rate of gall formation on potato roots is lower than on susceptible tomato roots. Three $R_0$ plants scored resistant to *Meloidogyne incognita*, because no galls could be found on the root cultures. All these resistant plants were transformed with cosmid Mi-11 comprising the internal PCR fragment indicating the presence of the Mi resistance gene.

TABLE 9

| Genotype | PCR fragment | $R_0$ plants Resistant | Susceptible |
|---|---|---|---|
| Mi-11 | + | 3 | 17 |
| Mi-11Δ | − | 0 | 6 |
| pJJ04541 | − | 0 | 5 |

Complementation Analysis: Screening for Nematode Resistance in Cuttings of Transformed Plants Rooted cuttings of Mi-11 transformed $R_0$ plants of potato have been subjected to the disease assay as described in Example 12. From each of the 19 transformants one to three cuttings have been assayed for resistance against *Meloidogyne incognita*. The results are shown in Table 10. In addition, 36 rooted cuttings of non-transformed potato plants (variety Diamant) were assayed (as susceptible controls) and were all susceptible. One $R_0$ plant scored resistant to *Meloidogyne incognita*, because no galls could be found on the root system.

TABLE 10

| Genotype | PCR fragment | $R_0$ plants Resistant | Susceptible |
|---|---|---|---|
| Mi-11 | + | 1 | 12 |
| Mi-11Δ | − | 0 | 6 |
| Non-transf. control | − | 0 | 1 |

What is claimed is:

1. An isolated nucleic acid which consists of the DNA sequence of FIG. 5 (SEQ ID NO: 15).

2. The nucleic acid of claim 1, which, when introduced in to a plant and expressed, renders said plant resistant to, at least, nematode *Meloidogyne incognita*.

3. The nucleic acid of claim 1, which, when introduced in to a plant and expressed, renders said plant resistant to, at least, aphid *Macrosiphum euphorbiae*.

4. The nucleic acid of claim 1, which, when introduced in to a plant and expressed, renders said plant resistant to, at least, aphid *Meloidogyne euphorbiae*.

5. A isolated fragment of the nucleic acid of claim 1, starting at nucleotide position 3263 and ending at nucleotide position 7111 of SEQ ID NO: 15.

6. The nucleic acid of claim 1, wherein said nucleic acid is contained in the genomic insert present in plasmid pKGmi-11 as deposited at the Centraalbureau voor Schimmelcultures on Aug. 5, 1996 and assigned the accession number CBS 822-96.

7. A recombinant DNA comprising the nucleic acid according to claim 1.

8. The recombinant DNA of claim 7, wherein said nucleic acid is under the control of a promoter which is effective to control the transcription of said DNA sequence in a plant cell.

9. A vector for transforming plant cells comprising the recombinant DNA of claim 7.

10. The plasmid pKGmi-11 deposited under CBS 822-96.

11. The plasmid pKGMi-18 deposited under CBS 821-96.

12. Bacterial cells comprising the vector according to claim 9 or the plasmid to claim 10 or 11.

13. Plant transformed with the recombinant DNA according to claim 7.

14. Plant cells transformed with the recombinant DNA according to claim 7.

15. A plant comprising the plant cells according to claim 14.

16. The plant according to claim 15, which has reduced susceptibility to root-knot nematode Meloidgyne or aphid Macrosiphum spp.

17. The plant according to claim 16, wherein said nematode is the root-knot nematode *Meloidogyne incognita*.

18. The plant according to claim 16, wherein said aphid is the aphid *Macrosiphum euphobiae*.

19. A seed comprising the recombinant DNA according to claim 7.

20. A process for obtaining plants having reduced susceptibility to a pathogen selected from a nematode Meloidogyne or an aphid Macrosiphum, said process comprising:

i) inserting into the genome of a plant cell the recombinant DNA according to claim 7 to obtain a transformed plant cell, ii) regenerating a genetically transformed plant from said transformed plant cell, and (iii) propagating said plant, thereby obtaining plants having reduced susceptibility to a pathogen selected from a nematode Meloidogyne or an aphid Macrosiphum.

21. The process according to claim 20, wherein said pathogen is the nematode *Meloidogyne incognita*.

22. The process according to claim 20, wherein said pathogen is the aphid *Macrosiphum euphorbiae*.

23. A process for protecting plants against a pathogen infection by, a nematode Meloidogyne or an aphid Macrosiphum, said process comprising i) inserting into the genome of plants susceptible to said pathogen, the recombinant DNA according to claim 7, and ii) growing said plants, wherein the resulting plants are protected against a pathogen infection by a nematode Meloidogyne or an aphid Macrosiphum.

* * * * *

UNITED STATES PATENT AND TRADEMARK OFFICE
CERTIFICATE OF CORRECTION

PATENT NO.   : 6,613,962 B1  
DATED        : September 2, 2003  
INVENTOR(S)  : Vos et al.

Page 1 of 1

It is certified that error appears in the above-identified patent and that said Letters Patent is hereby corrected as shown below:

Column 65,
Line 22, please insert -- namatode *Meloidogyne incognita* and aphid *Macrosiphum* -- in place of "*aphid Meloidogyne*"

Signed and Sealed this

Fourth Day of May, 2004

JON W. DUDAS
*Acting Director of the United States Patent and Trademark Office*